(12) United States Patent
Day et al.

(10) Patent No.: US 9,878,003 B2
(45) Date of Patent: Jan. 30, 2018

(54) METHOD OF TREATING BONE DISORDERS USING TSG-6

(71) Applicant: The University of Manchester, Manchester (GB)

(72) Inventors: Anthony Day, Manchester (GB); Caroline Milner, Manchester (GB); Sheona Patricia Drummond, Manchester (GB)

(73) Assignee: The University of Manchester, Manchester (GB)

( * ) Notice: Subject to any disclaimer, the term of this patent is extended or adjusted under 35 U.S.C. 154(b) by 75 days.

(21) Appl. No.: 14/481,841

(22) Filed: Sep. 9, 2014

(65) Prior Publication Data

US 2015/0057229 A1    Feb. 26, 2015

Related U.S. Application Data

(63) Continuation-in-part of application No. 12/281,920, filed as application No. PCT/GB2007/000772 on Mar. 6, 2007, now Pat. No. 9,066,908.

(30) Foreign Application Priority Data

Mar. 6, 2006    (GB) .................................. 0604460.6

(51) Int. Cl.
   *A61K 38/00*    (2006.01)
   *A61K 38/17*    (2006.01)
(52) U.S. Cl.
   CPC ............................... *A61K 38/1709* (2013.01)

(58) Field of Classification Search
   CPC .......................... A61K 38/1793; A61K 38/177
   See application file for complete search history.

(56) References Cited

U.S. PATENT DOCUMENTS

| | | | |
|---|---|---|---|
| 5,194,596 A | 3/1993 | Tischer et al. | |
| 5,350,836 A | 9/1994 | Kopchick et al. | |
| 6,518,401 B1 * | 2/2003 | Lee .................... | C07K 14/4718 530/300 |
| 6,806,351 B2 | 10/2004 | Ruben et al. | |
| 2006/0239965 A1 * | 10/2006 | Szoka, Jr. .............. | A61K 38/19 424/85.1 |

FOREIGN PATENT DOCUMENTS

| | | |
|---|---|---|
| EP | 0 705 842 A2 | 4/1996 |
| WO | 92/12175 A1 | 7/1992 |
| WO | 97/04075 A1 | 2/1997 |
| WO | 02/081521 A2 | 10/2002 |
| WO | 2005/060988 A1 | 7/2005 |
| WO | WO 2005060988 A1 * | 7/2005 |
| WO | 2009/154770 A2 | 12/2009 |

OTHER PUBLICATIONS

Chung-Faye et al., Mol Med Today Feb. 2000 (6):82-87.*

(Continued)

*Primary Examiner* — Cherie M Stanfield
(74) *Attorney, Agent, or Firm* — Seed IP Law Group LLP

(57) ABSTRACT

A method for inhibiting cartilage degradation comprising administering to a subject a therapeutically effective amount of a polypeptide comprising or consisting of a Link_TSG6 polypeptide is disclosed.

7 Claims, 18 Drawing Sheets

(56) References Cited

OTHER PUBLICATIONS

Verma, et al., (Nature Sep. 18, 1987 389:239-242).*
Juengst, (BMJ Jun. 28, 2003;326(7404)1410-1).*
Day et al., (Protein Express. Purif. 1996. 8:1-16).*
Roberts et al., (Eur Spine J. Feb. 2005;14(1):36-42. Epub Nov. 12, 2004).*
UniProtKB/Swiss-Prot O00300 (TR11B_HUMAN), "Tumor necrosis factor receptor superfamily member 11B," Gene Name: TNFRSF11B, last modified Mar. 2, 2010, Version 93, 10 pages.
UniProtKB/Swiss-Prot P98066 (TSG6_HUMAN), "Tumor necrosis factor-inducible gene 6 protein," Gene Name: TBFAIP6, last modified Mar. 2, 2010, Version 103, 7 pages.
Bárdos et al., "Anti-Inflammatory and Chondroprotective Effect of TSG-6 (Tumor Necrosis Factor-α-Stimulated Gene-6) in Murine Models of Experimental Arthritis," American Journal of Pathology 159(5):1711-1721, 2001.
Bayliss et al., "Up-regulation and differential expression of the hyaluronan-binding protein TSG-6 in cartilage and synovium in rheumatoid arthritis and osteoarthritis," OsteoArthritis and Cartilage 9:42-48, 2001.
Benjamin et al., "A plasticity window for blood vessel remodeling is defined by pericyte coverage of the preformed endothelial network and is regulated by PDGF-B and VEGF," Development 125:1591-1598, 1998.
Blundell et al., "The Link Module from Ovulation—and Inflammation-associated Protein TSG-6 Changes Conformation of Hyaluronan Binding," The Journal of Biological Chemistry 278(49):49261-49270, 2003.
Chung-Faye et al., "Gene therapy strategies for colon cancer," Molecular Medicine Today 6:82-87, 2000.
Crystal, "Transfer of Genes to Humans: Early Lessons and Obstacles to Success," Science 270:404-410, 1995.
Day et al., "Overexpression, Purification, and Refolding of Link Module from Human TSG-6 in Escherichia coli: Effect of Temperature, Media, and Mutagenesis on Lysine Misincorporation at Arginine AGA Codons," Protein Expression and Purification 8:1-16, 1996.
Getting et al., "The Link Module from Human TSG-6 Inhibits Neutrophil Migration in a Hyaluronan- and Inter-α-inhibitor-independent Manner," The Journal of Biological Chemistry 277(52):51068-51076, 2002.
Glant et al., "Cartilage-Specific Constitutive Expression of TSG-6 Protein (Product of Tumor Necrosis Factor α-Stimulated Gene 6) Provides a Chondroprotective, but Not Antiinflammatory Effect in Antigen-Induced Arthritis," Arthritis & Rheumatism 46(8):2207-2218, 2002.
Ikeda et al., "The Promyelotic Leukemia Zinc Finger Promotes Osteoblastic Differentiation of Human Mesenchymal Stem Cells as an Upstream Regulator of CBFA1," The Journal of Biological Chemistry 280(9):8523-8530, 2005.
Inoue et al., "Current Topics in Pharmacological Research on Bone Metabolism: Promyelotic Leukemia Zinc Finger (PLZF) and Tumor Necrosis Factor-α-Stimulated Gene 6 (TSG-6) Identified by Gene Expression Analysis Play Roles in the Pathogenesis of Ossification of the Posterior Longitudinal Ligament," J. Pharmacol. Sci. 100:205-210, 2006.
International Preliminary Report on Patentability, dated Sep. 9, 2008, for International Application No. PCT/GB2007/000772, 8 pages.
International Search Report, dated Aug. 22, 2007, for International Application No. PCT/GB2007/000772, 3 pages.
Juengst, "What next for human gene therapy?," BNJ 326:1410-1411, 2003.
Kong et al., "Activated T Cells Regulate Bone Loss and Joint Destruction in Adjuvant Arthritis Through Osteoprotegerin Ligand," Nature 402:304-309, 1999.
Kostenuik, "Osteoprotegerin and RANKL Regulate Bone Resorption, Density, Geometry and Strength," Curr. Opin. Pharmacol. 5:618-625, 2005.
Kuznetsova et al., "The N-terminal Module of Thrombospondin-1 Interacts with the Link Domain of TSG-6 and Enhances Its Covalent Association with the Heavy Chains of Inter-α-trypsin Inhibitor," The Journal of Biological Chemistry 280(35):30899-30908, 2005.
Mahoney et al., "Characterization of the Interaction between Tumor Necrosis Factor-stimulated Gene-6 and Heparin—Implications for the Inhibition of Plasmin in Extracellular Matrix Microenvironments," The Journal of Biological Chemistry 280(29):27044-27055, 2005.
Mahoney et al., "Mapping the Hyaluronan-binding Site on the Link Module from Human Tumor Necrosis Factor-stimulated Gene-6 by Site-directed Mutagenesis," The Journal of Biological Chemistry 276(25):22764-22771, 2001.
Maier et al., "TSG-6 Expression in Human Articular Chondrocytes," Arthritis & Rheumatism 39(4):552-559, 1996.
Margerie et al., "Complexity of IL-1β induced gene expression pattern in human articular chondrocytes," Osteoarthritis and Cartilage 5:129-138, 1997.
Marshall et al., "Blood-based biomarkers for detecting mild osteoarthritis in the human knee," OsteoArthritis and Cartilage 13:861-871, 2005.
Massagué, "The TGF-β Family of Growth and Differentiation Factors," Cell 49:437-438, 1987.
Milner et al., "TSG-6: a multifunctional protein associated with inflammation," Journal of Cell Science 116(10):1863-1873, 2003.
Milner et al., "TSG-6: a pluripotent inflammatory mediator?," Biochemical Society Transactions 34(3):446-450, 2006.
Mindrescu et al., "Amelioration of Collagen-Induced Arthritis in DBA/1J Mice by Recombinant TSG-6, A Tumor Necrosis Factor/Interleukin-1-Inducible Protein," Arthritis & Rheumatism 43(12):2668-2677, 2000.
Mindrescu et al., "Reduced Susceptibility to Collagen-Induced Arthritis in DBA/1J Mice Expressing the TSG-6 Transgene," Arthritis & Rheumatism 46(9):2453-2464, 2002.
Nentwich et al., "A Novel Allelic Variant of the Human TSG-6 Gene Encoding an Amino Acid Difference in the CUB Module," The Journal of Biological Chemistry 277(18):15354-15362, 2002.
Parkar et al., "Overlapping sites on the Link module of human TSG-6 mediate binding to hyaluronan and chondroitin-4-sulphate," FEBS Letters 410:413-417, 1997.
Parkar et al., "TSG-6 interacts with hyaluronan and aggrecan in a pH-dependent manner via a common functional element: implications for its regulation in inflamed cartilage," FEBS Letters 428:171-176, 1998.
Pilbeam et al., "Comparison of the Effects of Various Lengths of Synthetic Human Parathyroid Hormone-Related Peptide (hPTHrP) of Malignancy on Bone Resorption and Formation in Organ Culture," Bone 14:717-720, 1993.
Roberts et al., "TNFα-stimulated gene product (TSG-6) and its binding protein, IαI, in the human intervertebral disc: new molecules for the disc," Eur. Spine. J. 14:36-42, 2005.
Rugg et al., "Characterization of Complexes Formed between TSG-6 and Inter-α-inhibitor That Act as Intermediates in the Covalent Transfer of Heavy Chains onto Hyaluronan," The Journal of Biological Chemistry 280(27):25674-25686, 2005.
Salustri et al., "PTX3 plays a key role in the organization of the cumulus oophorus extracellular matrix and in in vivo fertilization," Development 131(7):1577-1586, 2004.
Stöve et al., "Interleukin-1β Induces Different Gene Expression of Stromelysin, Aggrecan and Tumor-Necrosis-Factor-Stimulated Gene 6 in Human Osteoarthritic Chondrocytes in vitro," Pathobiology 68:144-149, 2000.
Szántó et al., "Enhanced Neutrophil Extravasation and Rapid Progression of Proteoglycan-Induced Arthritis in TSG-6-Knockout Mice," Arthritis & Rheumatism 50(9):3012-3022, 2004.
Tait et al., "Ovarian Cancer BRCA1 Gene Therapy: Phase I and II Trial Differences in Immune Response and Vector Stability," Clinical Cancer Research 5:1708-1714, 1999.
Teitelbaum, "Bone Resorption by Osteoclasts," Science 289:1504-1508, 2000.

(56) References Cited

OTHER PUBLICATIONS

Tsukahara et al., "Tumour necrosis factor α-stimulated gene-6 inhibits osteoblastic differentiation of human mesenchymal stem cells induced by osteogenic differentiation medium and BMP-2," *Biochem. J.* 398:595-603, 2006.
Valdes et al., "Association Study of Candidate Genes for the Prevalence and Progression of Knee Osteoarthritis," *Arthritis & Rheumatism* 50(8):2497-2507, 2004.
Verma et al., "Gene therapy—promises, problems and prospects," *Nature* 389:239-242, 1997.
Vukicevic et al., "Induction of nephrogenic mesenchyme by osteogenic protein 1 (bone morphogenetic protein 7)," *Proc. Natl. Acad. Sci. USA* 93:9021-9026, 1996.
Wisniewski et al., "TNF/IL-1-Inducible Protein TSG-6 Potentiates Plasmin Inhibition by Inter-α-Inhibitor and Exerts a Strong Anti-Inflammatory Effect in Vivo," *The Journal of Immunology* 156:1609-1615, 1996.
Wisniewski et al., "TSG-6: A TNF-, IL-1-, and LPS-Inducible Secreted Glycoprotein Associated with Arthritis," *The Journal of Immunology* 151(11):6593-6601, 1993.
Baranova et al., "The inflammation-associated Protein TSG-6 Cross-links Hyaluronan via Hyaluronan-induced TSG-6 Oligomers," *J. Biol. Chem.* 286(29):25675-25686, 2011.
Dyer et al., "TSG-6 Inhibits Neutrophil Migration via Direct Interaction with the Chemokine CXCL8," *The Journal of Immunology* 192:2177-2185, 2014.

\* cited by examiner

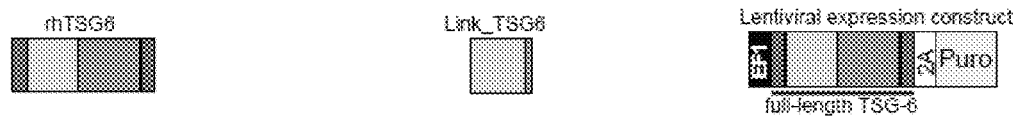
Figure 11
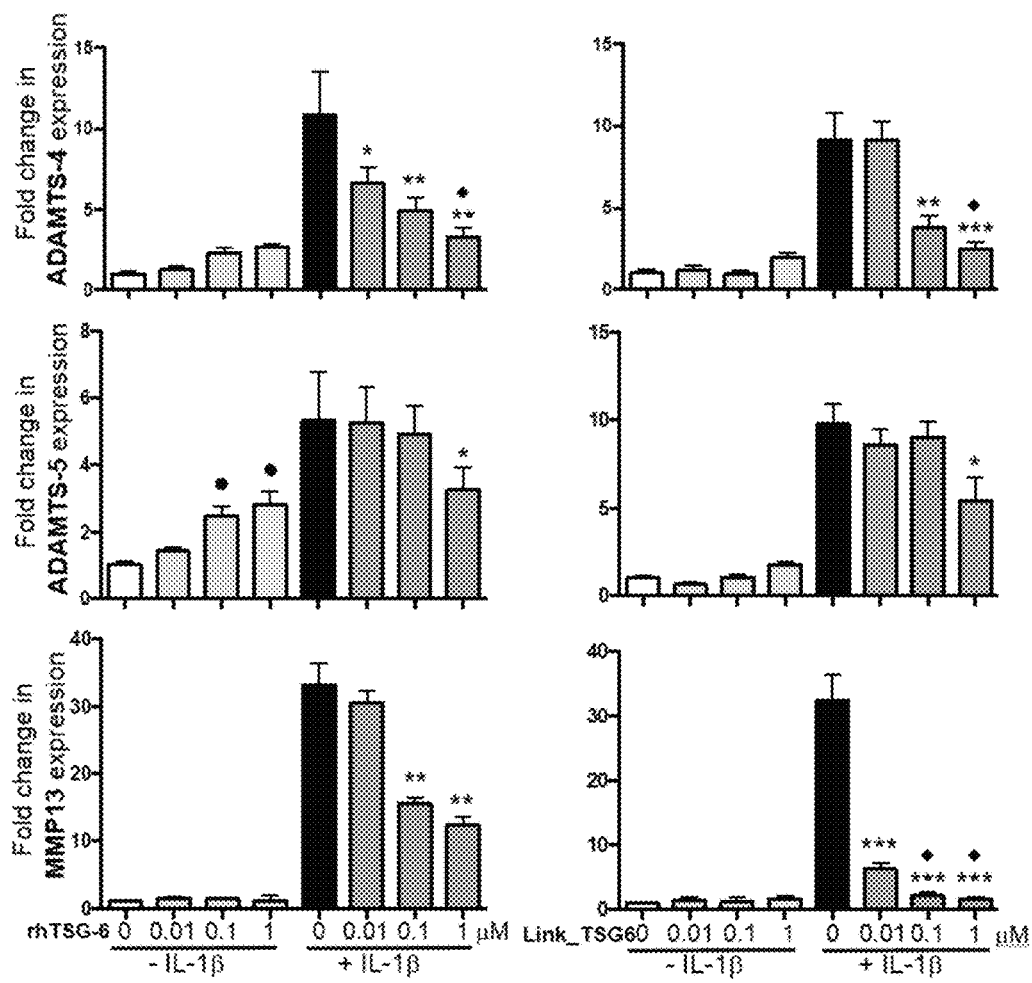
Figure 12A
Figure 12B

SEQUENCE LISTING

```
<160> NUMBER OF SEQ ID NOS: 27

<210> SEQ ID NO 1
<211> LENGTH: 1440
<212> TYPE: DNA
<213> ORGANISM: Homo sapiens
<220> FEATURE:
<221> NAME/KEY: CDS
<222> LOCATION: (77)..(910)

<400> SEQUENCE: 1
cagtcacatt tcagccactg ctctgagaat ttgtgagcag ccctaacag gctgttactt          60 cactacaact gacgat atg atc atc tta att tac tta ttt ctc ttg cta tgg       112
               Met Ile Ile Leu Ile Tyr Leu Phe Leu Leu Leu Trp
                 1               5                  10 gaa gac act caa gga tgg gga ttc aag gat gga att ttt cat aac tcc          160
Glu Asp Thr Gln Gly Trp Gly Phe Lys Asp Gly Ile Phe His Asn Ser
         15                  20                  25 ata tgg ctt gaa cga gca gcc ggt gtg tac cac aga gaa gca cgg tct          208
Ile Trp Leu Glu Arg Ala Ala Gly Val Tyr His Arg Glu Ala Arg Ser
 30                  35                  40 ggc aaa tac aag ctc acc tac gca gaa gct aag gcg gtg tgt gaa ttt          256
Gly Lys Tyr Lys Leu Thr Tyr Ala Glu Ala Lys Ala Val Cys Glu Phe
 45                  50                  55                  60 gaa ggc ggc cat ctc gca act tac aag cag cta gag gca gcc aga aaa          304
Glu Gly Gly His Leu Ala Thr Tyr Lys Gln Leu Glu Ala Ala Arg Lys
                 65                  70                  75 att gga ttt cat gtc tgt gct gct gga tgg atg gct aag ggc aga gtt          352
Ile Gly Phe His Val Cys Ala Ala Gly Trp Met Ala Lys Gly Arg Val
             80                  85                  90 gga tac ccc att gtg aag cca ggg ccc aac tgt gga ttt gga aaa act          400
Gly Tyr Pro Ile Val Lys Pro Gly Pro Asn Cys Gly Phe Gly Lys Thr
         95                 100                 105 ggc att att gat tat gga atc cgt ctc aat agg agt gaa aga tgg gat          448
Gly Ile Ile Asp Tyr Gly Ile Arg Leu Asn Arg Ser Glu Arg Trp Asp
110                 115                 120 gcc tat tgc tac aac cca cac gca aag gag tgt ggt ggc gtc ttt aca          496
Ala Tyr Cys Tyr Asn Pro His Ala Lys Glu Cys Gly Gly Val Phe Thr
125                 130                 135                 140
```

```
gat cca aag caa att ttt aaa tct cca ggc ttc cca aat gag tac gaa    544
Asp Pro Lys Gln Ile Phe Lys Ser Pro Gly Phe Pro Asn Glu Tyr Glu
            145                 150                 155 gat aac caa atc tgc tac tgg cac att aga ctc aag tat ggt cag cgt    592
Asp Asn Gln Ile Cys Tyr Trp His Ile Arg Leu Lys Tyr Gly Gln Arg
        160                 165                 170 att cac ctg agt ttt tta gat ttt gac ctt gaa gat gac cca ggt tgc    640
Ile His Leu Ser Phe Leu Asp Phe Asp Leu Glu Asp Asp Pro Gly Cys
    175                 180                 185 ttg gct gat tat gtt gaa ata tat gac agt tac gat gat gtc cat ggc    688
Leu Ala Asp Tyr Val Glu Ile Tyr Asp Ser Tyr Asp Asp Val His Gly
190                 195                 200 ttt gtg gga aga tac tgt gga gat gag ctt cca gat gac atc atc agt    736
Phe Val Gly Arg Tyr Cys Gly Asp Glu Leu Pro Asp Asp Ile Ile Ser
205                 210                 215                 220 aca gga aat gtc atg acc ttg aag ttt cta agt gat gct tca gtg aca    784
Thr Gly Asn Val Met Thr Leu Lys Phe Leu Ser Asp Ala Ser Val Thr
                225                 230                 235 gct gga ggt ttc caa atc aaa tat gtt gca atg gat cct gta tcc aaa    832
Ala Gly Gly Phe Gln Ile Lys Tyr Val Ala Met Asp Pro Val Ser Lys
            240                 245                 250 tcc agt caa gga aaa aat aca agt act act tct act gga aat aaa aac    880
Ser Ser Gln Gly Lys Asn Thr Ser Thr Thr Ser Thr Gly Asn Lys Asn
        255                 260                 265 ttt tta gct gga aga ttt agc cac tta taa aaaaaaaaaa aaggatgatc      930
Phe Leu Ala Gly Arg Phe Ser His Leu
    270                 275 aaaacacaca gtgtttatgt tggaatcttt tggaactcct ttgatctcac tgttattatt  990
aacatttatt tattattttt ctaaatgtga aagcaataca taatttaggg aaaattggaa  1050
aatataggaa actttaaacg agaaaatgaa acctctcata atcccactgc atagaaataa  1110
caagcgttaa cattttcata tttttttctt tcagtcattt ttctatttgt ggtatatgta  1170
tatatgtacc tatatgtatt tgcatttgaa attttggaat cctgctctat gtacagtttt  1230
gtattatact ttttaaatct tgaactttat aaacattttc tgaaatcatt gattattcta  1290
caaaaacatg attttaaaca gctgtaaaat attctatgat atgaatgttt tatgcattat  1350
ttaagcctgt ctctattgtt ggaatttcag gtcattttca taaatattgt tgcaataaat  1410
atccttgaac acaaaaaaaa aaaaaaaaaa                                   1440

<210> SEQ ID NO 2
<211> LENGTH: 277
<212> TYPE: PRT
<213> ORGANISM: Homo sapiens

<400> SEQUENCE: 2

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
```

```
                    85                  90                  95
Val Lys Pro Gly Pro Asn Cys Gly Phe Gly Lys Thr Gly Ile Ile Asp
                100                 105                 110

Tyr Gly Ile Arg Leu Asn Arg Ser Glu Arg Trp Asp Ala Tyr Cys Tyr
            115                 120                 125

Asn Pro His Ala Lys Glu Cys Gly Gly Val Phe Thr Asp Pro Lys Gln
        130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 3
<211> LENGTH: 260
<212> TYPE: PRT
<213> ORGANISM: Homo sapiens

<400> SEQUENCE: 3

Trp Gly Phe Lys Asp Gly Ile Phe His Asn Ser Ile Trp Leu Glu Arg
1               5                   10                  15

Ala Ala Gly Val Tyr His Arg Glu Ala Arg Ser Gly Lys Tyr Lys Leu
                20                  25                  30

Thr Tyr Ala Glu Ala Lys Ala Val Cys Glu Phe Glu Gly Gly His Leu
            35                  40                  45

Ala Thr Tyr Lys Gln Leu Glu Ala Ala Arg Lys Ile Gly Phe His Val
        50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Ile Arg Leu Asn Arg Ser Glu Arg Trp Asp Ala Tyr Cys Tyr Asn
            100                 105                 110

Pro His Ala Lys Glu Cys Gly Gly Val Phe Thr Asp Pro Lys Gln Ile
        115                 120                 125

Phe Lys Ser Pro Gly Phe Pro Asn Glu Tyr Glu Asp Asn Gln Ile Cys
    130                 135                 140

Tyr Trp His Ile Arg Leu Lys Tyr Gly Gln Arg Ile His Leu Ser Phe
145                 150                 155                 160

Leu Asp Phe Asp Leu Glu Asp Asp Pro Gly Cys Leu Ala Asp Tyr Val
                165                 170                 175
```

```
Glu Ile Tyr Asp Ser Tyr Asp Asp Val His Gly Phe Val Gly Arg Tyr
            180                 185                 190

Cys Gly Asp Glu Leu Pro Asp Asp Ile Ile Ser Thr Gly Asn Val Met
        195                 200                 205

Thr Leu Lys Phe Leu Ser Asp Ala Ser Val Thr Ala Gly Gly Phe Gln
    210                 215                 220

Ile Lys Tyr Val Ala Met Asp Pro Val Ser Lys Ser Ser Gln Gly Lys
225                 230                 235                 240

Asn Thr Ser Thr Thr Ser Thr Gly Asn Lys Asn Phe Leu Ala Gly Arg
                245                 250                 255

Phe Ser His Leu
            260

<210> SEQ ID NO 4
<211> LENGTH: 1440
<212> TYPE: DNA
<213> ORGANISM: Homo sapiens
<220> FEATURE:
<221> NAME/KEY: CDS
<222> LOCATION: (77)..(910)

<400> SEQUENCE: 4
cagtcacatt tcagccactg ctctgagaat ttgtgagcag cccctaacag gctgttactt    60
cactacaact gacgat atg atc atc tta att tac tta ttt ctc ttg cta tgg   112
                  Met Ile Ile Leu Ile Tyr Leu Phe Leu Leu Leu Trp
                   1               5                   10 gaa gac act caa gga tgg gga ttc aag gat gga att ttt cat aac tcc     160
Glu Asp Thr Gln Gly Trp Gly Phe Lys Asp Gly Ile Phe His Asn Ser
            15                  20                  25 ata tgg ctt gaa cga gca gcc ggt gtg tac cac aga gaa gca cgg tct     208
Ile Trp Leu Glu Arg Ala Ala Gly Val Tyr His Arg Glu Ala Arg Ser
        30                  35                  40 ggc aaa tac aag ctc acc tac gca gaa gct aag gcg gtg tgt gaa ttt     256
Gly Lys Tyr Lys Leu Thr Tyr Ala Glu Ala Lys Ala Val Cys Glu Phe
45                  50                  55                  60 gaa ggc ggc cat ctc gca act tac aag cag cta gag gca gcc aga aaa     304
Glu Gly Gly His Leu Ala Thr Tyr Lys Gln Leu Glu Ala Ala Arg Lys
                65                  70                  75 att gga ttt cat gtc tgt gct gct gga tgg atg gct aag ggc aga gtt     352
Ile Gly Phe His Val Cys Ala Ala Gly Trp Met Ala Lys Gly Arg Val
            80                  85                  90 gga tac ccc att gtg aag cca ggg ccc aac tgt gga ttt gga aaa act     400
Gly Tyr Pro Ile Val Lys Pro Gly Pro Asn Cys Gly Phe Gly Lys Thr
        95                  100                 105 ggc att att gat tat gga atc cgt ctc aat agg agt gaa aga tgg gat     448
Gly Ile Ile Asp Tyr Gly Ile Arg Leu Asn Arg Ser Glu Arg Trp Asp
    110                 115                 120 gcc tat tgc tac aac cca cac gca aag gag tgt ggt ggc gtc ttt aca     496
Ala Tyr Cys Tyr Asn Pro His Ala Lys Glu Cys Gly Gly Val Phe Thr
125                 130                 135                 140 gat cca aag cgg att ttt aaa tct cca ggc ttc cca aat gag tac gaa     544
Asp Pro Lys Arg Ile Phe Lys Ser Pro Gly Phe Pro Asn Glu Tyr Glu
                145                 150                 155 gat aac caa atc tgc tac tgg cac att aga ctc aag tat ggt cag cgt     592
Asp Asn Gln Ile Cys Tyr Trp His Ile Arg Leu Lys Tyr Gly Gln Arg
            160                 165                 170 att cac ctg agt ttt tta gat ttt gac ctt gaa gat gac cca ggt tgc     640
Ile His Leu Ser Phe Leu Asp Phe Asp Leu Glu Asp Asp Pro Gly Cys
        175                 180                 185
```

```
ttg gct gat tat gtt gaa ata tat gac agt tac gat gat gtc cat ggc    688
Leu Ala Asp Tyr Val Glu Ile Tyr Asp Ser Tyr Asp Asp Val His Gly
    190             195                 200 ttt gtg gga aga tac tgt gga gat gag ctt cca gat gac atc atc agt    736
Phe Val Gly Arg Tyr Cys Gly Asp Glu Leu Pro Asp Asp Ile Ile Ser
205                 210                 215                 220 aca gga aat gtc atg acc ttg aag ttt cta agt gat gct tca gtg aca    784
Thr Gly Asn Val Met Thr Leu Lys Phe Leu Ser Asp Ala Ser Val Thr
                225                 230                 235 gct gga ggt ttc caa atc aaa tat gtt gca atg gat cct gta tcc aaa    832
Ala Gly Gly Phe Gln Ile Lys Tyr Val Ala Met Asp Pro Val Ser Lys
            240                 245                 250 tcc agt caa gga aaa aat aca agt act act tct act gga aat aaa aac    880
Ser Ser Gln Gly Lys Asn Thr Ser Thr Thr Ser Thr Gly Asn Lys Asn
        255                 260                 265 ttt tta gct gga aga ttt agc cac tta taa aaaaaaaaaa aaggatgatc      930
Phe Leu Ala Gly Arg Phe Ser His Leu
    270                 275 aaaacacaca gtgtttatgt tggaatcttt tggaactcct tgatctcac tgttattatt   990 aacatttatt tattattttt ctaaatgtga aagcaataca taatttaggg aaaattggaa  1050
aatataggaa actttaaacg agaaaatgaa acctctcata atcccactgc atagaaataa  1110
caagcgttaa cattttcata ttttttctt tcagtcattt ttctatttgt ggtatatgta   1170
tatatgtacc tatatgtatt tgcatttgaa attttggaat cctgctctat gtacagtttt  1230
gtattatact ttttaaatct tgaactttat aaacattttc tgaaatcatt gattattcta  1290
caaaaacatg attttaaaca gctgtaaaat attctatgat atgaatgttt tatgcattat  1350
ttaagcctgt ctctattgtt ggaatttcag gtcattttca taaatattgt tgcaataaat  1410
atccttgaac acaaaaaaaa aaaaaaaaaa                                   1440

<210> SEQ ID NO 5
<211> LENGTH: 277
<212> TYPE: PRT
<213> ORGANISM: Homo sapiens

<400> SEQUENCE: 5

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
    130                 135                 140

Ile Phe Lys Ser Pro Gly Phe Pro Asn Glu Tyr Glu Asp Asn Gln Ile
145                 150                 155                 160
```

Cys Tyr Trp His Ile Arg Leu Lys Tyr Gly Gln Arg Ile His Leu Ser
            165                 170                 175

Phe Leu Asp Phe Asp Leu Glu Asp Asp Pro Gly Cys Leu Ala Asp Tyr
        180                 185                 190

Val Glu Ile Tyr Asp Ser Tyr Asp Asp Val His Gly Phe Val Gly Arg
            195                 200                 205

Tyr Cys Gly Asp Glu Leu Pro Asp Asp Ile Ile Ser Thr Gly Asn Val
        210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
            245                 250                 255

Lys Asn Thr Ser Thr Thr Ser Thr Gly Asn Lys Asn Phe Leu Ala Gly
        260                 265                 270

Arg Phe Ser His Leu
        275

<210> SEQ ID NO 6
<211> LENGTH: 260
<212> TYPE: PRT
<213> ORGANISM: Homo sapiens

<400> SEQUENCE: 6

Trp Gly Phe Lys Asp Gly Ile Phe His Asn Ser Ile Trp Leu Glu Arg
1               5                   10                  15

Ala Ala Gly Val Tyr His Arg Glu Ala Arg Ser Gly Lys Tyr Lys Leu
            20                  25                  30

Thr Tyr Ala Glu Ala Lys Ala Val Cys Glu Phe Glu Gly Gly His Leu
        35                  40                  45

Ala Thr Tyr Lys Gln Leu Glu Ala Ala Arg Lys Ile Gly Phe His Val
    50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
            85                  90                  95

Gly Ile Arg Leu Asn Arg Ser Glu Arg Trp Asp Ala Tyr Cys Tyr Asn
        100                 105                 110

Pro His Ala Lys Glu Cys Gly Gly Val Phe Thr Asp Pro Lys Arg Ile
    115                 120                 125

Phe Lys Ser Pro Gly Phe Pro Asn Glu Tyr Glu Asp Asn Gln Ile Cys
        130                 135                 140

Tyr Trp His Ile Arg Leu Lys Tyr Gly Gln Arg Ile His Leu Ser Phe
145                 150                 155                 160

Leu Asp Phe Asp Leu Glu Asp Asp Pro Gly Cys Leu Ala Asp Tyr Val
            165                 170                 175

Glu Ile Tyr Asp Ser Tyr Asp Asp Val His Gly Phe Val Gly Arg Tyr
        180                 185                 190

Cys Gly Asp Glu Leu Pro Asp Asp Ile Ile Ser Thr Gly Asn Val Met
    195                 200                 205

Thr Leu Lys Phe Leu Ser Asp Ala Ser Val Thr Ala Gly Gly Phe Gln
        210                 215                 220

Ile Lys Tyr Val Ala Met Asp Pro Val Ser Lys Ser Ser Gln Gly Lys
225                 230                 235                 240

Asn Thr Ser Thr Thr Ser Thr Gly Asn Lys Asn Phe Leu Ala Gly Arg

Phe Ser His Leu
        260

<210> SEQ ID NO 7
<211> LENGTH: 93
<212> TYPE: PRT
<213> ORGANISM: Homo sapiens

<400> SEQUENCE: 7

Val Tyr His Arg Glu Ala Arg Ser Gly Lys Tyr Lys Leu Thr Tyr Ala
1               5                   10                  15

Glu Ala Lys Ala Val Cys Glu Phe Glu Gly Gly His Leu Ala Thr Tyr
            20                  25                  30

Lys Gln Leu Glu Ala Ala Arg Lys Ile Gly Phe His Val Cys Ala Ala
        35                  40                  45

Gly Trp Met Ala Lys Gly Arg Val Gly Tyr Pro Ile Val Lys Pro Gly
    50                  55                  60

Pro Asn Cys Gly Phe Gly Lys Thr Gly Ile Ile Asp Tyr Gly Ile Arg
65                  70                  75                  80

Leu Asn Arg Ser Glu Arg Trp Asp Ala Tyr Cys Tyr Asn
                85                  90

<210> SEQ ID NO 8
<211> LENGTH: 319
<212> TYPE: DNA
<213> ORGANISM: Artificial sequence
<220> FEATURE:
<223> OTHER INFORMATION: Synthetic sequence: Link_TSG-6
<220> FEATURE:
<221> NAME/KEY: CDS
<222> LOCATION: (14)..(313)

<400> SEQUENCE: 8
aggagatata cat atg ggt gtg tac cac cgt gaa gca cgg tct ggc aaa         49
           Met Gly Val Tyr His Arg Glu Ala Arg Ser Gly Lys
           1               5                   10 tac aag ctc acc tac gca gaa gct aag gcg gtg tgt gaa ttt gaa ggc        97
Tyr Lys Leu Thr Tyr Ala Glu Ala Lys Ala Val Cys Glu Phe Glu Gly
        15                  20                  25 ggc cat ctc gca act tac aag cag cta gag gca gcc cgt aaa att gga       145
Gly His Leu Ala Thr Tyr Lys Gln Leu Glu Ala Ala Arg Lys Ile Gly
    30                  35                  40 ttt cat gtc tgt gct gct gga tgg atg gct aag ggc cgt gtt gga tac       193
Phe His Val Cys Ala Ala Gly Trp Met Ala Lys Gly Arg Val Gly Tyr
45                  50                  55                  60 ccc att gtg aag cca ggg ccc aac tgt gga ttt gga aaa act ggc att       241
Pro Ile Val Lys Pro Gly Pro Asn Cys Gly Phe Gly Lys Thr Gly Ile
                65                  70                  75 att gat tat gga atc cgt ctc aat agg agt gaa cgt tgg gat gcc tat       289
Ile Asp Tyr Gly Ile Arg Leu Asn Arg Ser Glu Arg Trp Asp Ala Tyr
            80                  85                  90 tgc tac aac cca cac gca aag taa gaattc                                319
Cys Tyr Asn Pro His Ala Lys
        95

<210> SEQ ID NO 9
<211> LENGTH: 99
<212> TYPE: PRT
<213> ORGANISM: Artificial sequence
<220> FEATURE:
<223> OTHER INFORMATION: Synthetic sequence: Link_TSG-6

<400> SEQUENCE: 9

Met Gly Val Tyr His Arg Glu Ala Arg Ser Gly Lys Tyr Lys Leu Thr
1               5                   10                  15

Tyr Ala Glu Ala Lys Ala Val Cys Glu Phe Glu Gly Gly His Leu Ala
            20                  25                  30

Thr Tyr Lys Gln Leu Glu Ala Ala Arg Lys Ile Gly Phe His Val Cys
        35                  40                  45

Ala Ala Gly Trp Met Ala Lys Gly Arg Val Gly Tyr Pro Ile Val Lys
    50                  55                  60

Pro Gly Pro Asn Cys Gly Phe Gly Lys Thr Gly Ile Ile Asp Tyr Gly
65                  70                  75                  80

Ile Arg Leu Asn Arg Ser Glu Arg Trp Asp Ala Tyr Cys Tyr Asn Pro
                85                  90                  95

His Ala Lys

<210> SEQ ID NO 10
<211> LENGTH: 149
<212> TYPE: PRT
<213> ORGANISM: Homo sapiens

<400> SEQUENCE: 10

Asn Pro His Ala Lys Glu Cys Gly Gly Val Phe Thr Asp Pro Lys Gln
1               5                   10                  15

Ile Phe Lys Ser Pro Gly Phe Pro Asn Glu Tyr Glu Asp Asn Gln Ile
            20                  25                  30

Cys Tyr Trp His Ile Arg Leu Lys Tyr Gly Gln Arg Ile His Leu Ser
        35                  40                  45

Phe Leu Asp Phe Asp Leu Glu Asp Asp Pro Gly Cys Leu Ala Asp Tyr
    50                  55                  60

Val Glu Ile Tyr Asp Ser Tyr Asp Asp Val His Gly Phe Val Gly Arg
65                  70                  75                  80

Tyr Cys Gly Asp Glu Leu Pro Asp Asp Ile Ile Ser Thr Gly Asn Val
                85                  90                  95

Met Thr Leu Lys Phe Leu Ser Asp Ala Ser Val Thr Ala Gly Gly Phe
            100                 105                 110

Gln Ile Lys Tyr Val Ala Met Asp Pro Val Ser Lys Ser Ser Gln Gly
        115                 120                 125

Lys Asn Thr Ser Thr Thr Ser Thr Gly Asn Lys Asn Phe Leu Ala Gly
    130                 135                 140

Arg Phe Ser His Leu
145

<210> SEQ ID NO 11
<211> LENGTH: 149
<212> TYPE: PRT
<213> ORGANISM: Homo sapiens

<400> SEQUENCE: 11

Asn Pro His Ala Lys Glu Cys Gly Gly Val Phe Thr Asp Pro Lys Arg
1               5                   10                  15

Ile Phe Lys Ser Pro Gly Phe Pro Asn Glu Tyr Glu Asp Asn Gln Ile
            20                  25                  30

Cys Tyr Trp His Ile Arg Leu Lys Tyr Gly Gln Arg Ile His Leu Ser
        35                  40                  45

Phe Leu Asp Phe Asp Leu Glu Asp Asp Pro Gly Cys Leu Ala Asp Tyr

```
            50                  55                  60
Val Glu Ile Tyr Asp Ser Tyr Asp Val His Gly Phe Val Gly Arg
 65                  70                  75                  80

Tyr Cys Gly Asp Glu Leu Pro Asp Asp Ile Ile Ser Thr Gly Asn Val
                 85                  90                  95

Met Thr Leu Lys Phe Leu Ser Asp Ala Ser Val Thr Ala Gly Gly Phe
            100                 105                 110

Gln Ile Lys Tyr Val Ala Met Asp Pro Val Ser Lys Ser Ser Gln Gly
        115                 120                 125

Lys Asn Thr Ser Thr Thr Ser Thr Gly Asn Lys Asn Phe Leu Ala Gly
    130                 135                 140

Arg Phe Ser His Leu
145

<210> SEQ ID NO 12
<211> LENGTH: 471
<212> TYPE: DNA
<213> ORGANISM: Artificial sequence
<220> FEATURE:
<223> OTHER INFORMATION: Synthetic sequence: CUB_C_TSG6
<220> FEATURE:
<221> NAME/KEY: CDS
<222> LOCATION: (14)..(466)

<400> SEQUENCE: 12
aggagatata cat atg aac cca cac gca aag gag tgt ggt ggc gtc ttt        49
               Met Asn Pro His Ala Lys Glu Cys Gly Gly Val Phe
                 1               5                  10 aca gat cca aag cga att ttt aaa tct cca ggc ttc cca aat gag tac       97
Thr Asp Pro Lys Arg Ile Phe Lys Ser Pro Gly Phe Pro Asn Glu Tyr
             15                  20                  25 gaa gat aac caa atc tgc tac tgg cac att aga ctc aag tat ggt cag      145
Glu Asp Asn Gln Ile Cys Tyr Trp His Ile Arg Leu Lys Tyr Gly Gln
         30                  35                  40 cgt att cac ctg agt ttt tta gat ttt gac ctt gaa gat gac cca ggt      193
Arg Ile His Leu Ser Phe Leu Asp Phe Asp Leu Glu Asp Asp Pro Gly
 45                  50                  55                  60 tgc ttg gct gat tat gtt gaa ata tat gac agt tac gat gat gtc cat      241
Cys Leu Ala Asp Tyr Val Glu Ile Tyr Asp Ser Tyr Asp Asp Val His
                 65                  70                  75 ggc ttt gtg gga aga tac tgt gga gat gag ctt cca gat gac atc atc      289
Gly Phe Val Gly Arg Tyr Cys Gly Asp Glu Leu Pro Asp Asp Ile Ile
             80                  85                  90 agt aca gga aat gtc atg acc ttg aag ttt cta agt gat gct tca gtg      337
Ser Thr Gly Asn Val Met Thr Leu Lys Phe Leu Ser Asp Ala Ser Val
         95                 100                 105 aca gct gga ggt ttc caa atc aaa tat gtt gca atg gat cct gta tcc      385
Thr Ala Gly Gly Phe Gln Ile Lys Tyr Val Ala Met Asp Pro Val Ser
    110                 115                 120 aaa tcc agt caa gga aaa aat aca agt act act tct act gga aat aaa      433
Lys Ser Ser Gln Gly Lys Asn Thr Ser Thr Thr Ser Thr Gly Asn Lys
125                 130                 135                 140 aac ttt tta gct gga aga ttt agc cac tta taa attcg                    471
Asn Phe Leu Ala Gly Arg Phe Ser His Leu
                145                 150

<210> SEQ ID NO 13
<211> LENGTH: 150
<212> TYPE: PRT
<213> ORGANISM: Artificial sequence
<220> FEATURE:
```

<223> OTHER INFORMATION: Synthetic sequence: CUB_C_TSG6

<400> SEQUENCE: 13

```
Met Asn Pro His Ala Lys Glu Cys Gly Gly Val Phe Thr Asp Pro Lys
1               5                   10                  15

Arg Ile Phe Lys Ser Pro Gly Phe Pro Asn Glu Tyr Glu Asp Asn Gln
            20                  25                  30

Ile Cys Tyr Trp His Ile Arg Leu Lys Tyr Gly Gln Arg Ile His Leu
        35                  40                  45

Ser Phe Leu Asp Phe Asp Leu Glu Asp Asp Pro Gly Cys Leu Ala Asp
    50                  55                  60

Tyr Val Glu Ile Tyr Asp Ser Tyr Asp Asp Val His Gly Phe Val Gly
65                  70                  75                  80

Arg Tyr Cys Gly Asp Glu Leu Pro Asp Asp Ile Ile Ser Thr Gly Asn
                85                  90                  95

Val Met Thr Leu Lys Phe Leu Ser Asp Ala Ser Val Thr Ala Gly Gly
            100                 105                 110

Phe Gln Ile Lys Tyr Val Ala Met Asp Pro Val Ser Lys Ser Ser Gln
        115                 120                 125

Gly Lys Asn Thr Ser Thr Thr Ser Thr Gly Asn Lys Asn Phe Leu Ala
    130                 135                 140

Gly Arg Phe Ser His Leu
145                 150
```

<210> SEQ ID NO 14
<211> LENGTH: 1356
<212> TYPE: DNA
<213> ORGANISM: Homo sapiens
<220> FEATURE:
<221> NAME/KEY: CDS
<222> LOCATION: (95)..(1300)

<400> SEQUENCE: 14

```
gtatatataa cgtgatgagc gtacgggtgc ggagacgcac cggagcgctc gcccagccgc      60
cgyctccaag cccctgaggt ttccggggac caca atg aac aag ttg ctg tgc tgc    115
                                      Met Asn Lys Leu Leu Cys Cys
                                      1               5 gcg ctc gtg ttt ctg gac atc tcc att aag tgg acc acc cag gaa acg      163
Ala Leu Val Phe Leu Asp Ile Ser Ile Lys Trp Thr Thr Gln Glu Thr
            10                  15                  20 ttt cct cca aag tac ctt cat tat gac gaa gaa acc tct cat cag ctg      211
Phe Pro Pro Lys Tyr Leu His Tyr Asp Glu Glu Thr Ser His Gln Leu
        25                  30                  35 ttg tgt gac aaa tgt cct cct ggt acc tac cta aaa caa cac tgt aca      259
Leu Cys Asp Lys Cys Pro Pro Gly Thr Tyr Leu Lys Gln His Cys Thr
40                  45                  50                  55 gca aag tgg aag acc gtg tgc gcc cct tgc cct gac cac tac tac aca      307
Ala Lys Trp Lys Thr Val Cys Ala Pro Cys Pro Asp His Tyr Tyr Thr
                60                  65                  70 gac agc tgg cac acc agt gac gag tgt cta tac tgc agc ccc gtg tgc      355
Asp Ser Trp His Thr Ser Asp Glu Cys Leu Tyr Cys Ser Pro Val Cys
            75                  80                  85 aag gag ctg cag tac gtc aag cag gag tgc aat cgc acc cac aac cgc      403
Lys Glu Leu Gln Tyr Val Lys Gln Glu Cys Asn Arg Thr His Asn Arg
        90                  95                  100 gtg tgc gaa tgc aag gaa ggg cgc tac ctt gag ata gag ttc tgc ttg      451
Val Cys Glu Cys Lys Glu Gly Arg Tyr Leu Glu Ile Glu Phe Cys Leu
105                 110                 115
```

| | | |
|---|---|---|
| aaa cat agg agc tgc cct cct gga ttt gga gtg gtg caa gct gga acc<br>Lys His Arg Ser Cys Pro Pro Gly Phe Gly Val Val Gln Ala Gly Thr<br>120                             125                            130                            135 | 499 | |
| cca gag cga aat aca gtt tgc aaa aga tgt cca gat ggg ttc ttc tca<br>Pro Glu Arg Asn Thr Val Cys Lys Arg Cys Pro Asp Gly Phe Phe Ser<br>                      140                           145                            150 | 547 | |
| aat gag acg tca tct aaa gca ccc tgt aga aaa cac aca aat tgc agt<br>Asn Glu Thr Ser Ser Lys Ala Pro Cys Arg Lys His Thr Asn Cys Ser<br>                155                           160                            165 | 595 | |
| gtc ttt ggt ctc ctg cta act cag aaa gga aat gca aca cac gac aac<br>Val Phe Gly Leu Leu Leu Thr Gln Lys Gly Asn Ala Thr His Asp Asn<br>        170                          175                           180 | 643 | |
| ata tgt tcc gga aac agt gaa tca act caa aaa tgt gga ata gat gtt<br>Ile Cys Ser Gly Asn Ser Glu Ser Thr Gln Lys Cys Gly Ile Asp Val<br>185                             190                            195 | 691 | |
| acc ctg tgt gag gag gca ttc ttc agg ttt gct gtt cct aca aag ttt<br>Thr Leu Cys Glu Glu Ala Phe Phe Arg Phe Ala Val Pro Thr Lys Phe<br>200                             205                            210                            215 | 739 | |
| acg cct aac tgg ctt agt gtc ttg gta gac aat ttg cct ggc acc aaa<br>Thr Pro Asn Trp Leu Ser Val Leu Val Asp Asn Leu Pro Gly Thr Lys<br>                      220                           225                            230 | 787 | |
| gta aac gca gag agt gta gag agg ata aaa cgg caa cac agc tca caa<br>Val Asn Ala Glu Ser Val Glu Arg Ile Lys Arg Gln His Ser Ser Gln<br>                235                           240                            245 | 835 | |
| gaa cag act ttc cag ctg ctg aag tta tgg aaa cat caa aac aaa gcc<br>Glu Gln Thr Phe Gln Leu Leu Lys Leu Trp Lys His Gln Asn Lys Ala<br>        250                          255                           260 | 883 | |
| caa gat ata gtc aag aag atc atc caa gat att gac ctc tgt gaa aac<br>Gln Asp Ile Val Lys Lys Ile Ile Gln Asp Ile Asp Leu Cys Glu Asn<br>265                             270                            275 | 931 | |
| agc gtg cag cgg cac att gga cat gct aac ctc acc ttc gag cag ctt<br>Ser Val Gln Arg His Ile Gly His Ala Asn Leu Thr Phe Glu Gln Leu<br>280                             285                            290                            295 | 979 | |
| cgt agc ttg atg gaa agc tta ccg gga aag aaa gtg gga gca gaa gac<br>Arg Ser Leu Met Glu Ser Leu Pro Gly Lys Lys Val Gly Ala Glu Asp<br>                      300                           305                            310 | 1027 | |
| att gaa aaa aca ata aag gca tgc aaa ccc agt gac cag atc ctg aag<br>Ile Glu Lys Thr Ile Lys Ala Cys Lys Pro Ser Asp Gln Ile Leu Lys<br>                315                           320                            325 | 1075 | |
| ctg ctc agt ttg tgg cga ata aaa aat ggc gac caa gac acc ttg aag<br>Leu Leu Ser Leu Trp Arg Ile Lys Asn Gly Asp Gln Asp Thr Leu Lys<br>        330                          335                           340 | 1123 | |
| ggc cta atg cac gca cta aag cac tca aag acg tac cac ttt ccc aaa<br>Gly Leu Met His Ala Leu Lys His Ser Lys Thr Tyr His Phe Pro Lys<br>345                             350                           355 | 1171 | |
| act gtc act cag agt cta aag aag acc atc agg ttc ctt cac agc ttc<br>Thr Val Thr Gln Ser Leu Lys Lys Thr Ile Arg Phe Leu His Ser Phe<br>360                             365                           370                            375 | 1219 | |
| aca atg tac aaa ttg tat cag aag tta ttt tta gaa atg ata ggt aac<br>Thr Met Tyr Lys Leu Tyr Gln Lys Leu Phe Leu Glu Met Ile Gly Asn<br>                      380                           385                            390 | 1267 | |
| cag gtc caa tca gta aaa ata agc tgc tta taa ctggaaatgg ccattgagct<br>Gln Val Gln Ser Val Lys Ile Ser Cys Leu<br>                395                           400 | 1320 | |
| gtttcctcac aattggcgag atcccatgga tgataa | 1356 | |

<210> SEQ ID NO 15
<211> LENGTH: 401
<212> TYPE: PRT
<213> ORGANISM: Homo sapiens

<400> SEQUENCE: 15

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Ala Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
    370                 375                 380

Phe Leu Glu Met Ile Gly Asn Gln Val Gln Ser Val Lys Ile Ser Cys
385                 390                 395                 400

Leu

<210> SEQ ID NO 16
<211> LENGTH: 20
<212> TYPE: DNA
<213> ORGANISM: Artificial sequences
<220> FEATURE:
<223> OTHER INFORMATION: Synthetic sequence: Forward primer

<400> SEQUENCE: 16
catgtgcaac gtcaaggctc                                                    20

<210> SEQ ID NO 17
<211> LENGTH: 20
<212> TYPE: DNA
<213> ORGANISM: Artificial sequences
<220> FEATURE:
<223> OTHER INFORMATION: Synthetic sequence: Reverse primer

<400> SEQUENCE: 17
caccaccaag ctgacaggat                                                    20

<210> SEQ ID NO 18
<211> LENGTH: 20
<212> TYPE: DNA
<213> ORGANISM: Artificial sequences
<220> FEATURE:
<223> OTHER INFORMATION: Synthetic sequence: Forward primer

<400> SEQUENCE: 18
gcctctccca tgacgattcc                                                    20

<210> SEQ ID NO 19
<211> LENGTH: 20
<212> TYPE: DNA
<213> ORGANISM: Artificial sequences
<220> FEATURE:
<223> OTHER INFORMATION: Synthetic sequence: Reverse primer

<400> SEQUENCE: 19
ccaggatctg ctttcgtggt                                                    20

<210> SEQ ID NO 20
<211> LENGTH: 20
<212> TYPE: DNA
<213> ORGANISM: Artificial sequences
<220> FEATURE:
<223> OTHER INFORMATION: Synthetic sequence: Forward primer

<400> SEQUENCE: 20
aggagcatgg cgacttctac                                                    20

<210> SEQ ID NO 21
<211> LENGTH: 20
<212> TYPE: DNA
<213> ORGANISM: Artificial sequences
<220> FEATURE:
<223> OTHER INFORMATION: Synthetic sequence: Reverse primer

<400> SEQUENCE: 21
caagacctaa ggagtggccg                                                    20

<210> SEQ ID NO 22
<211> LENGTH: 21
<212> TYPE: DNA
<213> ORGANISM: Artificial sequences
<220> FEATURE:

-continued

<223> OTHER INFORMATION: Synthetic sequence: Forward primer

<400> SEQUENCE: 22
catatggctt gaacgagcag c                                              21

<210> SEQ ID NO 23
<211> LENGTH: 20
<212> TYPE: DNA
<213> ORGANISM: Artificial sequences
<220> FEATURE:
<223> OTHER INFORMATION: Synthetic sequence: Reverse primer

<400> SEQUENCE: 23
ctttgcgtgt gggttgtagc                                                20

<210> SEQ ID NO 24
<211> LENGTH: 20
<212> TYPE: DNA
<213> ORGANISM: Artificial sequences
<220> FEATURE:
<223> OTHER INFORMATION: Synthetic sequence: Forward primer

<400> SEQUENCE: 24
ctcctgttcg acagtcagcc                                                20

<210> SEQ ID NO 25
<211> LENGTH: 22
<212> TYPE: DNA
<213> ORGANISM: Artificial sequences
<220> FEATURE:
<223> OTHER INFORMATION: Synthetic sequence: Reverse primer

<400> SEQUENCE: 25
cccaatacga ccaaatccgt tg                                             22

<210> SEQ ID NO 26
<211> LENGTH: 92
<212> TYPE: PRT
<213> ORGANISM: Homo sapiens

<400> SEQUENCE: 26

Val Tyr His Arg Glu Ala Arg Ser Gly Lys Tyr Lys Leu Thr Tyr Ala
1               5                   10                  15

Glu Ala Lys Ala Val Cys Glu Phe Glu Gly Gly His Leu Ala Thr Tyr
            20                  25                  30

Lys Gln Leu Glu Ala Ala Arg Lys Ile Gly Phe His Val Cys Ala Ala
        35                  40                  45

Gly Trp Met Ala Lys Gly Arg Val Gly Tyr Pro Ile Val Lys Pro Gly
    50                  55                  60

Pro Asn Cys Gly Phe Gly Lys Thr Gly Ile Ile Asp Tyr Gly Ile Arg
65                  70                  75                  80

Leu Asn Arg Ser Glu Arg Trp Asp Ala Tyr Cys Tyr
                85                  90

<210> SEQ ID NO 27
<211> LENGTH: 98
<212> TYPE: PRT
<213> ORGANISM: Artificial sequence
<220> FEATURE:
<223> OTHER INFORMATION: Synthetic sequence: Link_TSG-6

<400> SEQUENCE: 27

Gly Val Tyr His Arg Glu Ala Arg Ser Gly Lys Tyr Lys Leu Thr Tyr

```
1               5                   10                  15
Ala Glu Ala Lys Ala Val Cys Glu Phe Glu Gly Gly His Leu Ala Thr
            20                  25                  30

Tyr Lys Gln Leu Glu Ala Ala Arg Lys Ile Gly Phe His Val Cys Ala
            35                  40                  45

Ala Gly Trp Met Ala Lys Gly Arg Val Gly Tyr Pro Ile Val Lys Pro
            50                  55                  60

Gly Pro Asn Cys Gly Phe Gly Lys Thr Gly Ile Ile Asp Tyr Gly Ile
65                  70                  75                  80

Arg Leu Asn Arg Ser Glu Arg Trp Asp Ala Tyr Cys Tyr Asn Pro His
                85                  90                  95

Ala Lys
```

METHOD OF TREATING BONE DISORDERS USING TSG-6

CROSS-REFERENCE TO RELATED APPLICATIONS

This application is a Continuation-in-Part of U.S. patent application Ser. No. 12/281,920, filed Oct. 31, 2008, now pending; which application is a 371 National Phase of PCT Application No. PCT/GB07/00772, filed Mar. 6, 2007; which claims priority to United Kingdom Application No. 0604460.6, filed Mar. 6, 2006; which applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920133_401C1_SEQUENCE_LISTING.txt. The text file is 42 KB, was created on Sep. 9, 2014, and is being submitted electronically via EFS-Web.

FIELD OF THE INVENTION

The present invention relates to medical uses of Link_TSG6 polypeptides and polynucleotides and particularly, although not exclusively, to the use of a Link_TSG6 polypeptide or polynucleotide as a chondroprotective agent.

BACKGROUND OF THE INVENTION

Tumour necrosis factor (TNF)-stimulated gene 6 (TSG-6) is an inflammation-induced protein with protective roles in arthritis. TSG-6, the ~35 kDa secreted product of TNF-stimulated gene-6, is expressed in response to inflammatory mediators and growth factors, where there is believed to be little or no constitutive expression of the protein in healthy tissues (Milner & Day (2003) *J. Cell Sci.* 116, 1863-1873).

There is increasing evidence that TSG-6, whilst induced in response to inflammation, has anti-inflammatory and chondroprotective properties, making it an endogenous inhibitor of joint destruction. In this regard, TSG-6 has been found to have diverse biological activities, such as inhibition of neutrophil migration, down-regulation of plasmin activity, and the cross-linking of hyaluronan (HA) chains, which are all likely to contribute to its chondroprotective properties (Wisniewski et al. (1996) *J Immunol.* 156, 1609-1615; and Milner et al, (2006) *Biochem. Soc. Trans.* 34, 446-450).

TSG-6, which is comprised almost entirely of contiguous Link and CUB_C domains, binds to a variety of protein and glycosaminoglycan ligands (including HA, chondroitin-4-sulphate, aggrecan, inter-α-inhibitor (IαI), pentraxin-3, thrombospondin-1, fibronectin and heparin/heparan sulphate), where the majority of these interactions are mediated through its Link module domain. Mutagenesis studies have revealed that at least three non-overlapping ligand-binding surfaces are present on the Link module (Mahoney et al. (2005) *J. Biol. Chem.* 280, 27044-27055; and Kuznetsova et al. (2005) *J. Biol. Chem.* 280, 30899-30908). To date, the only ligand identified for the CUB_C domain is fibronectin (D J Mahoney & A J Day, unpublished data). In addition, this domain contains a divalent cation-binding site (Rugg et al. (2005) *J. Biol. Chem.* 280, 25674-25686).

TSG-6 has been detected in the context of inflammatory diseases such as rheumatoid arthritis (RA), where it is present in the synovial fluid, cartilage and synovia. It is likely that TSG-6 is produced locally in joint tissues, since its expression can be induced in cultured human chondrocytes by TNF, IL-1, IL-6, TGF-β and PDGF and it is constitutively expressed by synoviocytes from RA patients, where its production is further enhanced by treatment with IL-1, TNF and IL-17 (Milner et al, (2006) *Biochem. Soc. Trans.* 34, 446-450).

Importantly, a number of recent studies have revealed that TSG-6 has a protective role in experimental models of arthritis. For example, in a model of collagen-induced arthritis (CIA; an autoimmune polyarthritis with a histopathology similar to human RA), there was delayed onset of symptoms and reduction of both disease incidence and joint inflammation/destruction in TSG-6 transgenic mice or wild-type mice treated systemically with recombinant human TSG-6 (Mindrescu et al. (2000) *Arthritis Rheum.* 43, 2668-2677; and Mindrescu et al. (2002) *Arthritis Rheum.* 46, 2453-2464). In TSG-6 transgenic animals, an ameliorative effect comparable to anti-TNF-antibody treatment was seen. Furthermore, in cartilage-specific TSG-6 transgenic mice, the instigation of antigen-induced arthritis (AIA; a model of monoarticular arthritis) resulted in delayed cartilage damage compared to controls, with reduced degradation of aggrecan by MMPs and aggrecanase, and there was evidence of cartilage regeneration, 4-5 weeks after the onset of disease in these animals (Giant et al. (2002) *Arthritis Rheum.* 46, 2207-2218). Similar chondroprotective effects were seen in wild-type mice where recombinant murine TSG-6 was injected directly into the affected joint in AIA or intravenously in proteoglycan-induced arthritis (PGIA; a model of human RA) (Bardos et al. (2001) *Am. J. Pathol.* 159, 1711-1721).

The anti-inflammatory and chondroprotective effects of TSG-6 observed in these studies are likely due to more than one mechanism. Most importantly, TSG-6 is a potent inhibitor of neutrophil extravasation in vivo and has also been implicated in the inhibition of the protease network through its potentiation of the anti-plasmin activity of IαI, where plasmin is a key regulator of proteolysis during inflammation, e.g., via its activation of MMPs (Wisniewski et al. (1996) *J. Immunol.* 156, 1609-1615; and Getting et al. (2002) *J. Biol. Chem.* 277, 51068-51076). In this regard, mice lacking TSG-6 develop an accelerated and much more severe form of PGIA than controls, with rapid and extensive cartilage degradation and bone erosion (Szántá et al. (2004) *Arthritis Rheum.* 50, 3012-3022). Increased neutrophil infiltration and plasmin activity were suggested to account for these effects in the TSG-6$^{-/-}$ mice.

SUMMARY OF THE INVENTION

The present inventors have shown that TSG-6 inhibits bone resorption by osteoclasts. Osteoclasts are large, multinucleated cells that are derived from the monocyte/macrophage lineage and degrade bone matrix and mineral in the process of bone resorption. The present inventors have also shown that the absence of TSG-6 in TSG-6 knockout mice leads to increased bone resorption by osteoclasts. The present inventors have shown that TSG-6 is useful in treating and preventing a bone disease or condition associated with bone resorption by osteoclasts. The present inventors have also shown that administration of osteoprotegerin (OPG) in combination with TSG-6 results in a synergistic effect. A combination of TSG-6 and OPG inhibit bone resorption by osteoclasts to a greater extent than the sum of each factor alone.

In accordance with the present invention, there is thus provided the use of a TSG-6 polypeptide, or a polynucleotide encoding a TSG-6 polypeptide, in the manufacture of a medicament for the treatment or prevention of a bone disease or condition associated with bone resorption by osteoclasts. In a preferred embodiment, the medicament is administered in combination with a therapeutically or prophylactically effective amount of an OPG polypeptide, a polynucleotide encoding an OPG polypeptide or an OPG mimetic.

The present invention also provides a method of treating or preventing a bone disease or condition associated with bone resorption by osteoclasts in a subject in need thereof, the method comprising administering to the subject a therapeutically or prophylactically effective amount of an TSG-6 polypeptide, or a polynucleotide encoding an TSG-6 polypeptide. In a preferred embodiment, the method further comprises administering to the subject a therapeutically or prophylactically effective amount of an OPG polypeptide, a polynucleotide encoding an OPG polypeptide or an OPG mimetic.

The invention further provides:
use of:
  (a) a TSG-6 polypeptide, or a polynucleotide encoding a TSG-6 polypeptide; and
  (b) an OPG polypeptide, a polynucleotide encoding an OPG polypeptide or an OPG mimetic;
  in the manufacture of a medicament for the treatment or prevention of a disease or condition associated with bone resorption by osteoclasts;
a product containing:
  (a) a TSG-6 polypeptide, or a polynucleotide encoding a TSG-6 polypeptide; and
  (b) an OPG polypeptide, a polynucleotide encoding an OPG polypeptide or an OPG mimetic;
  for simultaneous, separate or sequential use in the treatment or prevention of a disease or condition associated with bone resorption by osteoclasts; and
use of:
  (a) a TSG-6 polypeptide, or a polynucleotide encoding a TSG-6 polypeptide; or
  (b) an OPG polypeptide, a polynucleotide encoding an OPG polypeptide or an OPG mimetic;
  in the manufacture of a medicament for the treatment or prevention by combination therapy of a disease or condition associated with bone resorption by osteoclasts, wherein (a) and (b) are administered simultaneously, separately or sequentially.

One advantage of the present invention is that the TSG-6 polypeptide or polynucleotide can have anti-inflammatory and/or chondroprotective effects in addition to inhibiting bone resorption by osteoclasts. These anti-inflammatory and/or chondroprotective effects can result from the inhibition of neutrophil migration, the down-regulation of plasmin activity and/or the TSG-6-mediated cross-linking of HA chains.

The present invention also provides a chondroprotective composition comprising a therapeutically effective amount of a polypeptide comprising or consisting of a Link_TSG6 polypeptide, or a therapeutically effective amount of a polynucleotide encoding a Link_TSG6 polypeptide. In some embodiments, a Link_TSG6 polypeptide comprises or consists of the amino acid sequence of SEQ ID NO: 9, 27, 7 or 26, or an amino acid sequence having at least 95% identity to the amino acid sequence of SEQ ID NO: 9, 27, 7 or 26. In some embodiments the polynucleotide comprises or consists of (i) the coding sequence of SEQ ID NO 8, or (ii) a coding sequence which is degenerate as a result of the genetic code to SEQ ID NO: 8, or (iii) a coding sequence having at least 95% identity to the coding sequence of SEQ ID NO: 8 or a coding sequence which is degenerate as a result of the genetic code to SEQ ID NO: 8. Also provided is a method for inhibiting joint destruction, the method comprising administering to a subject a therapeutically effective amount of a polypeptide comprising or consisting of a Link_TSG6 polypeptide, or a therapeutically effective amount of a polynucleotide encoding a Link_TSG6 polypeptide, thereby inhibiting joint destruction. Also provided is a method for inhibiting cartilage degradation, the method comprising administering to a subject a therapeutically effective amount of a polypeptide comprising or consisting of a Link_TSG6 polypeptide, or a therapeutically effective amount of a polynucleotide encoding a Link_TSG6 polypeptide, thereby inhibiting cartilage degradation.

Also provided is a method for preventing, delaying or treating damage to cartilage tissue, the method comprising administering to a subject a therapeutically effective amount of a polypeptide comprising or consisting of a Link_TSG6 polypeptide, or a therapeutically effective amount of a polynucleotide encoding a Link_TSG6 polypeptide, thereby preventing, delaying or treating further damage to cartilage tissue. In some embodiments, loss or degeneration of cartilage tissue is not associated with the loss of bone tissue.

Also provided is a method for preventing, delaying or treating loss or degeneration of cartilage tissue, the method comprising administering to a patient in need thereof a therapeutically effective amount of a polypeptide comprising or consisting of a Link_TSG6 polypeptide, or a therapeutically effective amount of a polynucleotide encoding a Link_TSG6 polypeptide, thereby preventing, delaying or treating further loss or degeneration of cartilage tissue. In some embodiments, the patient is diagnosed as having osteoarthritis. In some embodiments osteoarthritis is selected from trauma or injury induced osteoarthritis, age-related osteoarthritis and non-age related osteoarthritis.

Also provided is a method for maintaining effective cartilage tissue in the joint of a patient following injury or trauma to the joint, the method comprising administering to a patient a therapeutically effective amount of a polypeptide comprising or consisting of a Link_TSG6 polypeptide, or a therapeutically effective amount of a polynucleotide encoding a Link_TSG6 polypeptide following said injury or trauma, thereby preventing, delaying or treating the onset of loss or degeneration of cartilage tissue in said joint.

Also provided is a method for preventing, delaying or treating loss or degeneration of cartilage tissue, the method comprising administering to a subject susceptible to loss or degeneration of cartilage tissue, or already experiencing loss or degeneration of cartilage tissue, a therapeutically effective amount of a polypeptide comprising or consisting of a Link_TSG6 polypeptide, or a therapeutically effective amount of a polynucleotide encoding a Link_TSG6 polypeptide, thereby preventing, delaying or treating further loss or degeneration of cartilage tissue. In some embodiments, the subject is susceptible to loss of cartilage tissue, or is already experiencing loss of cartilage tissue, as a result of injury or trauma.

Also provided is a method for upregulating expression of TSG-6 in a subject, the method comprising administering to a subject a therapeutically effective amount of a polypeptide comprising or consisting of a Link_TSG6 polypeptide, or a therapeutically effective amount of a polynucleotide encoding a Link_TSG6 polypeptide, thereby upregulating expression of TSG-6 in said subject.

Also provided is a method for reducing or inhibiting the catabolic activity of chondrocytes in a subject, the method comprising administering to a subject a therapeutically effective amount of a polypeptide comprising or consisting of a Link_TSG6 polypeptide, or a therapeutically effective amount of a polynucleotide encoding a Link_TSG6 polypeptide, thereby reducing or inhibiting the catabolic activity of chondrocytes in said subject.

Also provided is a method for increasing or promoting the anabolic activity of chondrocytes in a subject, the method comprising administering to a subject a therapeutically effective amount of a polypeptide comprising or consisting of a Link_TSG6 polypeptide, or a therapeutically effective amount of a polynucleotide encoding a Link_TSG6 polypeptide, thereby increasing or promoting the anabolic activity of chondrocytes in said subject.

Also provided is a method for reducing or inhibiting expression of one or more cartilage degrading enzymes in a subject, the method comprising administering to a subject a therapeutically effective amount of a polypeptide comprising or consisting of a Link_TSG6 polypeptide, or a therapeutically effective amount of a polynucleotide encoding a Link_TSG6 polypeptide, thereby reducing or inhibiting expression of one or more cartilage degrading enzymes in said subject. In some embodiments, the cartilage degrading enzyme is selected from: cartilage degrading enzymes which are upregulated in response to inflammatory mediators, aggrecanases, collagenases, ADAMTS-4, ADAMTS-5, MMP3 and MMP13. In some embodiments inflammatory mediators are selected from IL-1α, IL-1β or TNFα.

In some embodiments of the methods, the subject is susceptible to loss or degeneration of cartilage tissue, or is already experiencing loss or degeneration of cartilage tissue. In some embodiments the subject is susceptible to or experiencing loss or degeneration of cartilage tissue as a result of a disease or condition, such as osteoarthritis. In some embodiments the subject is susceptible to or experiencing loss or degeneration of cartilage tissue as a result of injury or trauma.

In some embodiments of the methods, administration is by injection. In some embodiments, administration is to a site of injury or trauma, optionally by injection. In some embodiments, administration is to a site susceptible to or experiencing loss or degeneration of cartilage tissue. In some embodiments a site is susceptible to or experiencing loss or degeneration of cartilage tissue as a result of injury or trauma. Administration may be into a joint or directly to cartilage tissue.

In some embodiments of the methods of the invention, a Link_TSG6 polypeptide comprises, consists or consists essentially of the amino acid sequence of SEQ ID NO: 9, 27, 7 or 26, or an amino acid sequence having at least 95% identity to the amino acid sequence of SEQ ID NO: 9, 27, 7 or 26.

In some embodiments of the methods of the invention, the polynucleotide encoding Link_TSG6 comprises or consists of (i) the coding sequence of SEQ ID NO 8, or (ii) a coding sequence which is degenerate as a result of the genetic code to SEQ ID NO: 8, or (iii) a coding sequence having at least 95% identity to the coding sequence of SEQ ID NO: 8 or a coding sequence which is degenerate as a result of the genetic code to SEQ ID NO: 8.

BRIEF DESCRIPTION OF THE DRAWINGS

FIG. 11 shows schematics of recombinant human TSG-6 (rhTSG6), Link_TSG6 and the lentiviral expression construct used to enable constitutive over-expression of full-length TSG-6 protein by chondrocytes (with an antibiotic resistance gene (Puro) for selection of transfected cells).

FIGS. 12A-12C show that exogenous addition of rhTSG-6 or Link_TSG6 or endogenous over-expression of TSG-6 down-regulates cytokine mediated stimulation of catabolic enzyme expression. (A)-(C) Inhibition of IL-1β-stimulated ADAMTS-4, ADAMTS-5 and MMP13 expression by (12A) exogenous addition of rhTSG-6 (at 0.01, 0.1 or 1 μM), (12B) exogenous addition of Link_TSG6 (at 0.01, 0.1 or 1 μM) or (12C) constitutive over-expression of full-length TSG-6. Fold changes in expression were calculated relative to 'no addition' controls. Data are presented as mean values±S.E.M. (n=3 (exogenous protein additions) or n=2 (constitutive over-expression) independent experiments in which each condition was tested in triplicate). *p<0.05, p<0.01, *p<0.001 relative to IL-1β alone; ˙p<0.05 relative to 'no addition' control; ˙no significant difference to 'no addition' control; determined by one-way ANOVA with Tukey's and Dunnett's post hoc tests.

(B) Zoning of cartilage relative to cartilage thickness and proximity to underlying bone (deep, medial and superficial) and horizontal distance from macroscopically undamaged (UD) with the remaining cartilage divided into thirds (T1, T2 and T3). Scale Bar=4000 μm. (C) Semi-automated 'object counting' in each defined zone in a minimum of 3 sequential sections revealing TSG-6 and HA distribution predominantly at the most damaged margins and a small population of TSG-6+ and/or HA+ cells within the deep zones of macroscopically undamaged cartilage. (D) High magnification image showing TSG-6+ clusters of chondrocytes within damaged cartilage. Scale bar=200 μm.

Figure 18A:
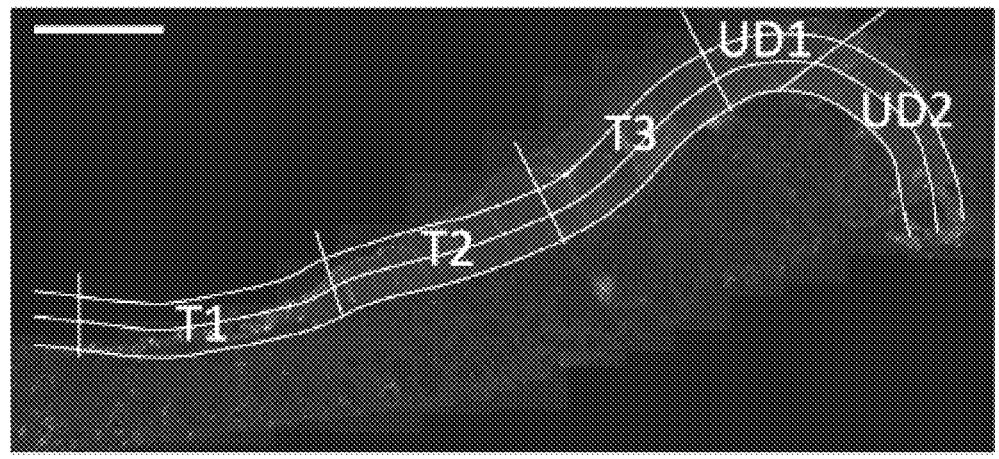
Figure 18B:
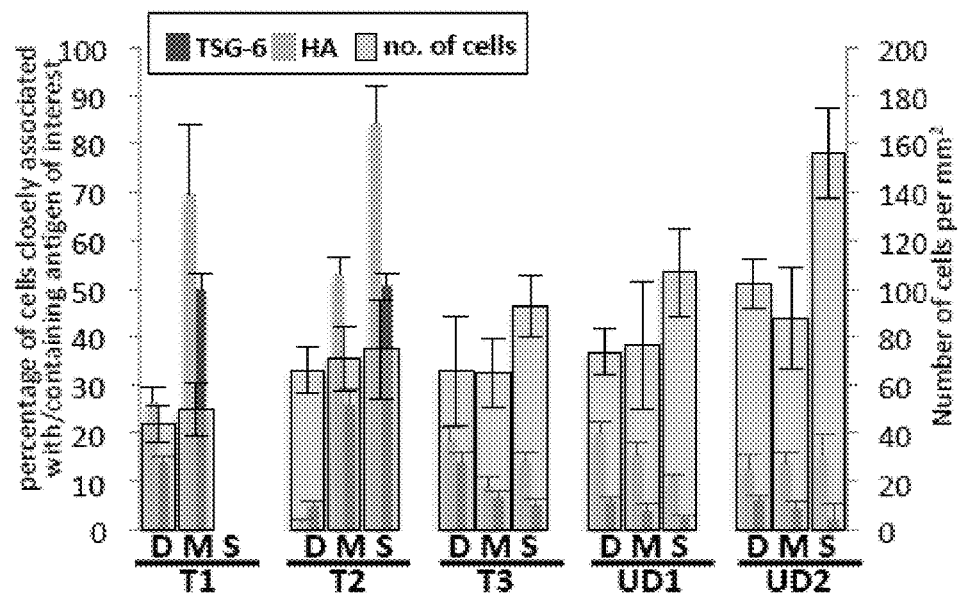

FIGS. 18A-18B show quantitative analysis of TSG-6 distribution/cell-association throughout diseased cartilage in another donor tissue sample from an osteoarthritis patient. (A) Zoning scheme for this specific donor tissue sample. Scale Bar=3000 μm. (B) Semi-automated 'object counting' in each defined zone in a minimum of 3 sequential sections revealing TSG-6 and HA distribution predominantly at the most damaged margins and a small population of TSG-6+ and/or HA+ cells within the deep zones of macroscopically undamaged cartilage. In this sample, the absence of T1 (S) is due to complete degradation and loss of cartilage in this superficial region.

Figure 19A:
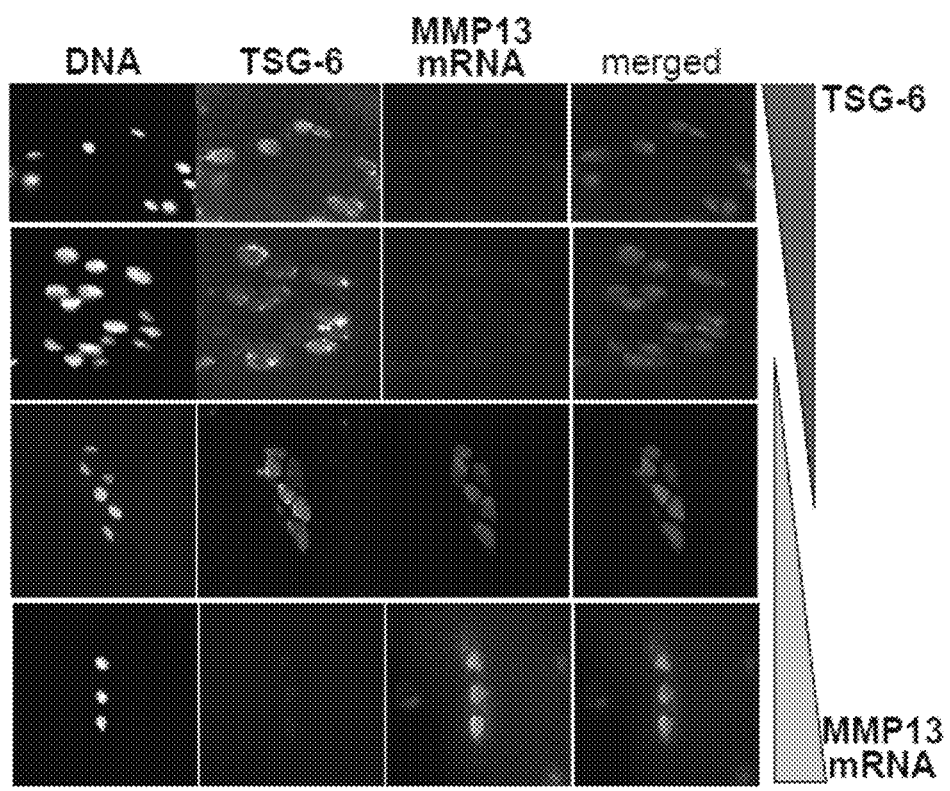
Figure 19B:
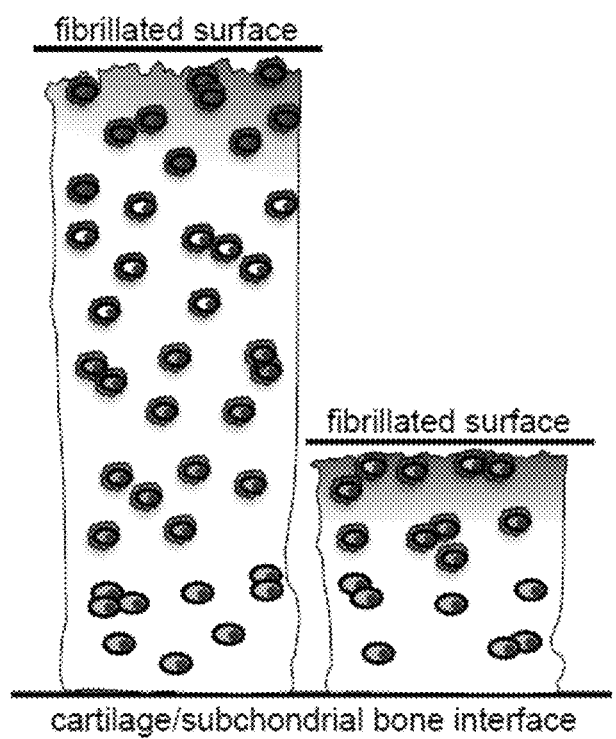

FIGS. 19A and 19B indicate that there is an inverse correlation between the presence of TSG-6 protein and the expression of MMP13 mRNA in OA cartilage (A) The localisation of TSG-6 protein (identified with RAH-1 antibody) and the expression of MMP13 mRNA (identified with DIG-labelled anti-sense RNA probes, and signal amplification using the Tyramide Signal Amplification System) were determined in human OA cartilage. Images are representative of staining observed in the 4 donor tissue samples analysed. (B) Schematic representation of TSG-6 protein and MMP13 RNA distribution/expression in damaged OA cartilage (based on data from 4 donor tissue samples). Chondrocytes within regions of the cartilage with high levels of matrix and/or cell-associated TSG-6 staining (red) have low levels of MMP13 expression (green).

BRIEF DESCRIPTION OF THE SEQUENCES

SEQ ID NO: 1 shows the nucleic acid sequence encoding the full-length Q144 allotypic variant of human TSG-6.

SEQ ID NO: 2 shows the amino acid sequence of full-length Q144 allotypic variant of human TSG-6. This allotypic variant has a glutamine residue (Q) at position 144. It is the most common allotypic variant and is found in approximately 86% of the Caucasian population (Nentwich et al. (2002) 277, 15354-15362).

SEQ ID NO: 3 (residues 18-277 of SEQ ID NO: 2) shows the amino acid sequence of the Q144 allotypic variant of human TSG-6 without the signal sequence.

SEQ ID NO: 4 shows the nucleic acid sequence encoding the full-length R144 allotypic variant of human TSG-6.

SEQ ID NO: 5 shows the amino acid sequence of full-length R144 allotypic variant of human TSG-6. This allotypic variant has an arginine residue (R) at position 144. It is the less common allotypic variant and is found in approximately 14% of the Caucasian population (Nentwich et al. (2002) 277, 15354-15362).

SEQ ID NO: 6 (residues 18-277 of SEQ ID NO: 5) shows the amino acid sequence of the R144 allotypic variant of human TSG-6 without the signal sequence.

SEQ ID NO: 7 (residues 37-129 of SEQ ID NOs: 2 and 5) shows the amino acid sequence of the Link module of human TSG-6.

SEQ ID NO: 8 shows the nucleic acid sequence encoding Link_TSG6 used in the Examples (Day et al. (1996) *Protein Expr. Pruif.* 8, 1-16).

SEQ ID NO: 9 shows the amino acid sequence of Link_TSG6 used in the Examples. Residues 3-95 of SEQ ID NO: 9 correspond to SEQ ID NO: 7 (residues 37-129 of SEQ ID NOs: 2 and 5). Residues 3-94 correspond to SEQ ID NO: 26 (residues 37-128 of SEQ ID NOs: 2 and 5). The initiating methionine (Met-1) is removed on expression of Link_TSG6 (Day et al. (1996) *Protein Expr. Pruif.* 8, 1-16).

SEQ ID NO: 10 (residues 129-277 of SEQ ID NO: 2) shows the amino acid sequence of the CUB_C domain of the Q144 allotypic variant of human TSG-6.

SEQ ID NO: 11 (residues 129-277 of SEQ ID NO: 5) shows the amino acid sequence of the CUB_C domain of the R144 allotypic variant of human TSG-6.

SEQ ID NO: 12 shows the nucleic acid sequence encoding the CUB_C_TSG6 used in the Examples.

SEQ ID NO: 13 shows the amino acid sequence of CUB_C_TSG6 used in the Examples. Residues 2-150 of SEQ ID NO: 13 correspond to SEQ ID NO: 11 (residues 129-277 of SEQ ID NO: 5). The initiating methionine (Met-1) is not removed on expression of CUB_C_TSG6 (A J Day, unpublished data).

SEQ ID NO: 14 shows the nucleic acid sequence encoding full-length human OPG.

SEQ ID NO: 15 shows the amino acid sequence of full-length human OPG.

SEQ ID NO: 16 shows the forward primer sequence for ADAMTS-4 used for gene expression analysis SEQ ID NO: 17 shows the reverse primer sequence for ADAMTS-4 used for gene expression analysis SEQ ID NO: 18 shows the forward primer sequence for ADAMTS-5 used for gene expression analysis SEQ ID NO: 19 shows the reverse primer sequence for ADAMTS-5 used for gene expression analysis SEQ ID NO: 20 shows the forward primer sequence for MMP13 used for gene expression analysis SEQ ID NO: 21 shows the reverse primer sequence for MMP13 used for gene expression analysis SEQ ID NO: 22 shows the forward primer sequence for TSG-6 used for gene expression analysis SEQ ID NO: 23 shows the reverse primer sequence for TSG-6 used for gene expression analysis SEQ ID NO: 24 shows the forward primer sequence for GAPDH used for gene expression analysis SEQ ID NO: 25 shows the reverse primer sequence for GAPDH used for gene expression analysis SEQ ID NO: 26 shows the amino acid sequence of the Link module of human TSG-6 corresponding to residues 37-128 of SEQ ID NOs: 2 and 5.

SEQ ID NO: 27 shows the amino acid sequence of Link_TSG6 on expression, corresponding to SEQ ID NO: 9 with the initiating methionine (Met-1) removed.

DETAILED DESCRIPTION OF THE INVENTION

The present invention provides a method for treating or preventing bone diseases or conditions associated with bone resorption by osteoclasts, which method comprises administering to a subject a TSG-6 polypeptide or a polynucleotide encoding a TSG-6 polypeptide. In a preferred embodiment, the method further comprises administering to the subject a therapeutically or prophylactically effective amount of an OPG polypeptide, a polynucleotide encoding an OPG polypeptide or an OPG mimetic.

The present invention also provides a method for treating or preventing diseases or conditions associated with loss of cartilage, which comprises administering to a subject a Link_TSG6 polypeptide or a polynucleotide encoding a Link_TSG6 polypeptide. In some embodiments, the method further comprises administering to the subject a therapeutically or prophylactically effective amount of an OPG polypeptide, a polynucleotide encoding an OPG polypeptide or an OPG mimetic.

The inventors have shown that Link_TSG6 is more potent than recombinant humanTSG-6 in inhibiting pro-inflammatory cytokine (IL-1α, IL-1β or TNFα)-induced expression of cartilage degrading enzymes (ADAMTS4, ADAMTS5, MMP13 and MMP3) and in inducing native TSG-6 expression. In human osteoarthritis, ADAMTS4 and ADAMTS5 are the major aggrecanase enzymes that degrade cartilage proteoglycan, whilst MMP13 is the major collagenase contributing to irreversible matrix breakdown.

This finding identifies a chondroprotective mechanism whereby 'TSG-6' acts directly on chondrocytes to suppress the effects of pro-inflammatory mediators. The inventors show Link_TSG6 to be more potent than recombinant human TSG-6 at inhibiting the production of cartilage-degrading enzymes and therefore provides the basis for greater efficacy in the prevention/treatment of cartilage loss (e.g. in the context of osteoarthritis).

TSG-6 Polypeptides

The TSG-6 polypeptide is preferably human TSG-6, or a variant or fragment of human TSG-6 which retains RANKL binding activity. The TSG-6 polypeptide may have the ability to inhibit bone resorption by osteoclasts. The TSG-6 polypeptide may have the ability to inhibit IL-1α, IL-1β or TNFα induced expression of ADAMTS-4, ADAMTS-5, MMP13 or MMP3 preferably in a dose-dependent manner. The variant can be a TSG-6 polypeptide from another organism, such as a primate, a mouse or a rat.

A TSG-6 polypeptide may comprise:

(a) the amino acid sequence of SEQ ID NO: 2 or 5;

(b) a variant thereof having at least 50% identity to the amino acid sequence of SEQ ID NO: 2 or 5 and having receptor activator of NF$_K$B ligand (RANKL) binding activity; or (c) a fragment of either (a) or (b) having RANKL binding activity.

The polypeptide may comprise, or consists of, the sequence of SEQ ID NO: 2 or 5.

The TSG-6 polypeptide can additionally lack a signal sequence. Accordingly, the TSG-6 polypeptide may comprise:

(a) the amino acid sequence of SEQ ID NO: 3 or 6;

(b) a variant thereof having at least 50% identity to the amino acid sequence of SEQ ID NO: 3 or 6 and having RANKL binding activity; or (c) a fragment of either (a) or (b) having RANKL binding activity.

The TSG-6 polypeptide may consist of the sequence shown in SEQ ID NO: 3 or 6.

The TSG-6 polypeptide can additionally lack the CUB_C domain. The CUB_C domain corresponds to residues 129-277 of SEQ ID NOs: 2 and 5.

In some embodiments, the TSG-6 polypeptide comprises only the Link module of human or mammalian TSG-6 or consists essentially of only the Link module of human or mammalian TSG-6. In some embodiments, the TSG-6 polypeptide comprises or consists essentially of the amino acid sequence according to SEQ ID NO: 9 or 27.

The Link module corresponds to residues 37-128 of SEQ ID NOs: 2 and 5 and is shown in SEQ ID NO: 26.

The Link module is responsible for the hyaluronan (HA) binding activity, chondroitin-4-sulphate binding activity, aggrecan binding activity, inter-α-inhibitor (IαI) binding activity, bikunin binding activity, versican binding activity, dermatan sulphate binding activity, pentraxin-3 binding activity, thrombospondin-1 binding activity, heparin/heparan sulphate binding activity and RANKL binding activity of TSG-6.

Link_TSG6 may be a fragment of TSG-6 exhibiting one or more of hyaluronan (HA) binding activity, chondroitin-4-sulphate binding activity, aggrecan binding activity, inter-α-inhibitor (IαI) binding activity, bikunin binding activity, versican binding activity, dermatan sulphate binding activity, pentraxin-3 binding activity, thrombospondin-1 binding activity, heparin/heparan sulphate binding activity, RANKL binding activity, bone morphogenetic protein (BMP)-2 binding activity, BMP-13 binding activity, BMP-14 binding activity, CXCL8 binding activity, and CCL5 binding activity.

The LINK domain of TSG6 may be the region of full-length TSG-6 N-terminal to the CUB_C domain.

The LINK domain may contain the amino acid sequence of SEQ ID NO:7 or 9.

Link_TSG6 is preferably a polypeptide comprising or consisting of: (i) the amino acid sequence of SEQ ID NO: 9, 27, 7 or 26, or (ii) an amino acid sequence having one of at least 80%, 85%, 90%, 91%, 92%, 93%, 94%, 95%, 96%, 97%, 98%, 99% or 100% identity to the amino acid sequence of SEQ ID NO: 9, 27, 7 or 26.

Link_TSG6 polypeptide may have the ability to inhibit IL-1α, IL-β or TNFα induced expression of ADAMTS-4, ADAMTS-5, MMP13 or MMP3, preferably in a dose-dependent manner.

A polynucleotide encoding Link_TSG6 is preferably a polynucleotide comprising or consisting of (i) the coding sequence of SEQ ID NO 8, or (ii) a coding sequence which is degenerate as a result of the genetic code to SEQ ID NO: 8, or (iii) a coding sequence having one of at least 80%, 85%, 90%, 91%, 92%, 93%, 94%, 95%, 96%, 97%, 98%, 99% or 100% identity to the coding sequence of SEQ ID NO: 8 or a coding sequence which is degenerate as a result of the genetic code to SEQ ID NO: 8.

Accordingly, a Link_TSG6 polypeptide may preferably comprise:

(a) the amino acid sequence of SEQ ID NO: 7;
(b) a variant thereof having at least 50% identity to the amino acid sequence of SEQ ID NO: 7 and having RANKL binding activity; or
(c) a fragment of either (a) or (b) having RANKL binding activity.

The Link_TSG6 polypeptide may preferably consist of, or consist essentially of, the sequence shown in SEQ ID NO: 7.

SEQ ID NO: 9 shows a recombinant polypeptide which includes the Link module of TSG-6 (Link_TSG6). Accordingly, the TSG-6 polypeptide used in the invention may preferably comprise:

(a) the amino acid sequence of SEQ ID NO: 9;
(b) a variant thereof having at least 50% identity to the amino acid sequence of SEQ ID NO: 9 and having RANKL binding activity; or
(c) a fragment of either (a) or (b) having RANKL binding activity.

The Link_TSG6 polypeptide may preferably consist of, or consist essentially of, the sequence shown in SEQ ID NO: 9.

In some embodiments a TSG-6 polypeptide can lack the Link module. The Link module corresponds to residues 37-128 of SEQ ID NOs: 2 and 5. The TSG-6 polypeptide can comprise only the CUB_C domain of human TSG-6. The CUB_C domain corresponds to residues 129-277 of SEQ ID NOs: 2 and 5 and is shown in SEQ ID NOs: 10 and 11. The CUB module is also responsible for the fibronectin binding activity of TSG-6 and RANKL binding activity of TSG-6. Accordingly, a TSG-6 polypeptide may comprise:

(a) the amino acid sequence of SEQ ID NO: 10 or 11;
(b) a variant thereof having at least 50% identity to the amino acid sequence of SEQ ID NO: 10 or 11 and having RANKL binding activity; or
(c) a fragment of either (a) or (b) having RANKL binding activity.

The TSG-6 polypeptide may consist of the sequence shown in SEQ ID NO: 10 or 11.

SEQ ID NO: 13 shows a recombinant polypeptide which includes the CUB_C domain of TSG-6 (CUB_C_TSG-6). Accordingly, a TSG-6 polypeptide may comprise:

(a) the amino acid sequence of SEQ ID NO: 13;
(b) a variant thereof having at least 50% identity to the amino acid sequence of SEQ ID NO: 13 and having RANKL binding activity; or
(c) a fragment of either (a) or (b) having RANKL binding activity.

A TSG-6 polypeptide may consist of the sequence shown in SEQ ID NO: 13.

Variant polypeptides are those for which the amino acid sequence varies from that in SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13, but which retain the function of TSG-6. Variant polypeptides may inhibit bone resorption by osteoclasts or exhibit chondroprotective activity. The variant polypeptides may bind to RANKL or inhibit IL-1α, IL-β or TNFα induced expression of ADAMTS-4, ADAMTS-5 or MMP13, preferably in a dose-dependent manner The variant polypeptides may also bind to one or more of HA, chondroitin-4-sulphate, aggrecan, inter-α-inhibitor (IαI), bikunin, versican, dermatan sulphate, pentraxin-3, thrombospondin-1, heparin/heparan sulphate and/or fibronectin, BMP-2, BMP-13, BMP-14, CXCL8, and CCL5. The variant polypeptides can also have anti-inflammatory and/or chondroprotective effects.

The binding activity of the variant polypeptides can be modified to produce different effects in a subject treated in accordance with the invention. For instance, a variant polypeptide that is unable to bind inter-α-inhibitor (IαI) may not produce anti-inflammatory effects in the subject. Alternatively, a variant polypeptide that is unable to bind to HA may not produce chondroprotective effects in the subject.

Typically, polypeptides with more than about 50%, 55% or 65% identity, preferably at least 70%, at least 80%, at least 90% and particularly preferably at least 95%, at least 97% or at least 99% identity, with the amino acid sequence of SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13 are considered variants of the TSG-6 protein. Such variants include allelic variants and the deletion, modification or addition of single amino acids or groups of amino acids within the protein sequence, as long as the peptide maintains the basic functionality of TSG-6. The identity of variants of SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13 can be measured over a region of at least 50, at least 75, at least 100, at least 150, at least 200 or at least 250 or more contiguous amino acids of the sequence shown in SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13, or more preferably over the full length of SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13.

Variants of the amino acid sequence of SEQ ID NO: 2, SEQ ID NO: 3, SEQ ID NO: 5, SEQ ID NO: 6, SEQ ID NO: 7 or SEQ ID NO: 9 preferably contain the residues shown to be essential for hyaluronan binding in Mahoney et al. (2001) *J. Biol. Chem.* 276, 22764-22771 and Blundell et al. (2003) *J. Biol. Chem.* 278, 49261-49270. Variants of the amino acid sequence of SEQ ID NO: 2 or 5 preferably contain the residues Lys-46 and/or Tyr-47 and/or Tyr-94 and/or Phe-105 and/or Tyr-113 of SEQ ID NO: 2 or 5. Most preferably, the variant of SEQ ID NO: 2 or 5 contains each of residues Lys-46, Tyr-47, Tyr-94, Phe-105 and Tyr-113 of SEQ ID NO: 2 or 5.

Variants of the amino acid sequence of SEQ ID NO: 3 or 6 preferably contain the residues Lys-29 and/or Tyr-30 and/or Tyr-77 and/or Phe-88 and/or Tyr-96 of SEQ ID NO: 3 or 6. Most preferably, the variant of SEQ ID NO: 3 or 6 contains each of residues Lys-29, Tyr-30, Tyr-77, Phe-88 and Tyr-96 of SEQ ID NO: 3 or 6.

Variants of the amino acid sequence of SEQ ID NO: 7 preferably contain the residues Lys-10 and/or Tyr-11 and/or Tyr-58 and/or Phe-69 and/or Tyr-77 of SEQ ID NO: 7. Most preferably, the variant of SEQ ID NO: 7 contains each of residues Lys-10, Tyr-11, Tyr-58, Phe-69 and Tyr-77 of SEQ ID NO: 7.

Variants of the amino acid sequence of SEQ ID NO: 9 preferably contain the residues Lys-12 and/or Tyr-13 and/or Tyr-60 and/or Phe-71 and/or Tyr-79 of SEQ ID NO: 9. Most preferably, the variant of SEQ ID NO: 9 contains each of residues Lys-12, Tyr-13, Tyr-60, Phe-71 and Tyr-79 of SEQ ID NO: 9.

Amino acid identity may be calculated using any suitable algorithm. For example the UWGCG Package provides the BESTFIT program which can be used to calculate homology (for example used on its default settings) (Devereux et al (1984) *Nucleic Acids Research* 12, 387-395). The PILEUP and BLAST algorithms can be used to calculate homology or line up sequences (such as identifying equivalent or corresponding sequences (typically on their default settings), for example as described in Altschul (1993) *J Mol Evol* 36, 290-300; Altschul, et al (1990) *J Mol Biol* 215, 403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89, 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sd. USA 90, 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The variant sequences typically differ by at least 1, 2, 5, 10, 20, 30, 50 or more mutations (which can be substitutions, deletions or insertions of amino acids). For example, from 1 to 50, 2 to 30, 3 to 20 or 5 to 10 amino acid substitutions, deletions or insertions can be made. The modified polypeptide may generally retain RANKL binding or the ability to inhibit IL-1α or IL-β induced expression of ADAMTS-4, ADAMTS-5 or MMP13, preferably in a dose-dependent manner. The substitutions are preferably conservative substitutions, for example according to the following Table. Amino acids in the same block in the second column and preferably in the same line in the third column may be substituted for each other:

| ALIPHATIC | Non-polar | G A P |
| --- | --- | --- |
| | | I L V |
| | Polar - uncharged | C S T M |
| | | N Q |
| | Polar - charged | D E |
| | | K R |
| AROMATIC | | H F W Y |

The fragment of the TSG-6 polypeptide used in the invention retains the function of TSG-6. The fragment polypeptides therefore may inhibit bone resorption by osteoclasts or exhibit chondroprotective activity. The fragment polypeptides may bind to RANKL or have the ability to inhibit IL-1α, IL-β or TNFα induced expression of ADAMTS-4, ADAMTS-5 or MMP13, preferably in a dose-dependent manner.

The fragment polypeptides typically also bind to HA, chondroitin-4-sulphate, aggrecan, inter-α-inhibitor (IαI), bikunin, versican, dermatan sulphate, pentraxin-3, thrombospondin-1, heparin/heparan sulphate and/or fibronectin, BMP-2, BMP-13, BMP-14, CXCL8, and CCL5. The fragment polypeptides can also have anti-inflammatory and/or chondroprotective effects.

The binding activity of the fragment polypeptides can be modified to produce different effects in a subject treated in accordance with the invention. For instance, a fragment polypeptide that is unable to bind inter-α-inhibitor (IαI) may not produce anti-inflammatory effects in the subject. Alternatively, a fragment polypeptide that is unable to bind to HA may not produce chondroprotective effects in the subject.

The fragment of the TSG-6 polypeptide used in the invention is typically at least 10, for example at least 15, 20, 25, 30, 40, 50, 60, 70, 80, 90 or more amino acids in length, up to 100, 150, 200 or 250 amino acids in length, as long as it retains the RANKL binding activity of TSG-6. Preferably, the fragment of the TSG-6 polypeptide includes the sequence shown in SEQ ID NO: 7. Fragments of the amino acid sequence of SEQ ID NO: 2, SEQ ID NO: 3, SEQ ID NO: 5, SEQ ID NO: 6, SEQ ID NO: 7 or SEQ ID NO: 9 preferably contain the residues shown to be essential for hyaluronan binding in Mahoney et al (2001) *J. Biol. Chem.* 276, 22764-22771 and Blundell et al (2003) *J. Biol. Chem.* 278, 49261-49270. Fragments of the amino acid sequence of SEQ ID NO: 2 or 5 preferably contain the residues Lys-46 and/or Tyr-47 and/or Tyr-94 and/or Phe-105 and/or Tyr-113 of SEQ ID NO: 2 or 5. Most preferably, the fragment of SEQ ID NO: 2 or 5 contains each of residues Lys-46, Tyr-47, Tyr-94, Phe-105 and Tyr-113 of SEQ ID NO: 2 or 5.

Fragments of the amino acid sequence of SEQ ID NO: 7 preferably contain the residues Lys-10 and/or Tyr-11 and/or Tyr-58 and/or Phe-69 and/or Tyr-77 of SEQ ID NO: 7. Most preferably, the fragment of SEQ ID NO: 7 contains each of residues Lys-10, Tyr-11, Tyr-58, Phe-69 and Tyr-77 of SEQ ID NO: 7.

Fragments of the amino acid sequence of SEQ ID NO: 9 preferably contain the residues Lys-12 and/or Tyr-13 and/or Tyr-60 and/or Phe-71 and/or Tyr-79 of SEQ ID NO: 9. Most preferably, the fragment of SEQ ID NO: 9 contains each of residues Lys-12, Tyr-13, Tyr-60, Phe-71 and Tyr-79 of SEQ ID NO: 9.

A preferred fragment for use in the invention is residues 36-133 of SEQ ID NO: 1.

The TSG-6 polypeptides used in the invention may be chemically modified, e.g. post-translationally modified. For example, they may be glycosylated, phosphorylated or comprise modified amino acid residues. They may be modified by the addition of histidine residues to assist their purification or by the addition of a signal sequence to promote insertion into the cell membrane. Such modified polypeptides fall within the scope of the term "polypeptide" used herein.

The RANKL binding activity can be determined by means of a suitable assay. For example, the RANKL binding activity of a TSG-6 polypeptide can be determined using the method described in the Examples. Suitable assays for determining the ability of a TSG-6 polypeptide to bind to HA, chondroitin-4-sulphate, aggrecan, inter-α-inhibitor (IαI), bikunin, versican, dermatan sulphate, pentraxin-3, thrombospondin-1, heparin/heparan sulphate and fibronectin are well-known in the art (Getting et al. (2002) *J. Biol. Chem.* 277, 51068-51076; Mahoney et al. (2005) *J. Biol. Chem.* 280, 27044-27055; Salustri et al. (2004) *Development* 131, 1577-1586; Parkar et al. (1997) *FEBS Lett.* 410, 413-417; Parkar et al. (1998) *FEBS Lett.* 428, 171-176; Mahoney et al. (2001) *J. Biol. Chem.* 276, 22764-22771; Nentwich et al. (2002) *J. Biol. Chem.* 211, 15354-15362; and Kuznetsova et al. (2005) *J. Biol. Chem.* 280, 30899-30908).

TSG-6 polypeptides for use in accordance with the invention may display the ability to inhibit bone resorption by osteoclasts. The osteoclast inhibitory activity can be determined by means of a suitable assay. For example, the osteoclast inhibitory activity of a TSG-6 polypeptide can be determined using any of the methods described in the Example below.

TSG-6 polypeptides for use in the invention may be in a substantially isolated form. It will be understood that the polypeptide may be mixed with carriers or diluents which will not interfere with the intended purpose of the polypeptide and still be regarded as substantially isolated. A polypeptide for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

TSG-6 polypeptides for use in the present invention may be natural or non-naturally occurring polypeptides. Polypeptides may be isolated from any suitable organism that expresses a TSG-6 polypeptide. The TSG-6 polypeptide may be isolated from a human or another suitable mammal, such as primates, rats or mice. Polypeptides for use in the invention may also be prepared as fragments of such isolated polypeptides.

Further, the TSG-6 polypeptides may also be made synthetically or by recombinant means. For example, a recombinant TSG-6 polypeptide may be produced by transfecting cells in culture with an expression vector comprising a nucleotide sequence encoding the polypeptide operably linked to suitable control sequences, culturing the cells, extracting and purifying the TSG-6 polypeptide produced by the cells. Methods for the recombinant production of polypeptides are well-known in the art (for example, Sambrook et al, 2001, Molecular Cloning: a laboratory manual, $3^{rd}$ edition, Cold Harbour Laboratory Press).

The amino acid sequence of TSG-6 polypeptides for use in the invention may be modified to include non-naturally occurring amino acids or to increase the stability of the compound. When the polypeptides are produced by synthetic means, such amino acids may be introduced during production. The polypeptides may also be modified following either synthetic or recombinant production.

TSG-6 polypeptides for use in the invention may also be produced using D-amino acids. In such cases the amino acids will be linked in reverse sequence in the C to N orientation. This is conventional in the art for producing such polypeptides.

A number of side chain modifications are known in the art and may be made to the side chains of the TSG-6 polypeptides, provided that the polypeptides retain osteoclast inhibitory activity.

TSG-6 Polynucleotides

In accordance with the invention, a polynucleotide encoding a TSG-6 polypeptide, variant or fragment may be used to treat or prevent a disease or condition associated with bone resorption by osteoclasts or for the treatment or prevention of a disease or condition associated with loss of cartilage.

In particular the polynucleotide may comprise, consist of, or consist essentially of: (a) the coding sequence of SEQ ID NO: 1, 4, 8 or 12; (b) a sequence which is degenerate as a result of the genetic code to the sequence as defined in (a); (c) a sequence having at least 60% identity to a sequence as defined in (a) or (b) and which encodes a polypeptide having RANKL binding activity; or (d) a fragment of any one of the sequences as defined in (a), (b) or (c) which encodes a polypeptide having RANKL binding activity. The polynucleotide may comprise, consist of, or consist essentially of: (a) the coding sequence of SEQ ID NO: 1, 4, 8 or 12; (b)

a sequence which is degenerate as a result of the genetic code to the sequence as defined in (a); (c) a sequence having at least 60% identity to a sequence as defined in (a) or (b) and which encodes a polypeptide having the ability to inhibit bone resorption by osteoclasts; or (d) a fragment of any one of the sequences as defined in (a), (b) or (c) which encodes a polypeptide having the ability to inhibit bone resorption by osteoclasts or exhibit chondroprotective activity.

Typically the TSG-6 polynucleotide is DNA. However, the polynucleotide may be a RNA polynucleotide. The polynucleotide may be single or double stranded, and may include within it synthetic or modified nucleotides.

A polynucleotide of the invention can typically hybridize to the coding sequence or the complement of the coding sequence of SEQ ID NO: 1, 4, 8 or 12 at a level significantly above background. Background hybridization may occur, for example, because of other DNAs present in a DNA library. The signal level generated by the interaction between a polynucleotide of the invention and the coding sequence or complement of the coding sequence of SEQ ID NO: 1, 4, 8 or 12 is typically at least 10 fold, preferably at least 100 fold, as intense as interactions between other polynucleotides and the coding sequence of SEQ ID NO: 1, 4, 8 or 12. The intensity of interaction may be measured, for example, by radiolabelling the probe, e.g. with $^{32}$P. Selective hybridisation is typically achieved using conditions of medium to high stringency. However, such hybridisation can be carried out under any suitable conditions known in the art (see Sambrook et al., 2001, Molecular Cloning: a laboratory manual, $3^{rd}$ edition, Cold Harbour Laboratory Press). For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 1, 4, 8 or 12 can be modified by nucleotide substitutions, for example from 1, 2 or 3 to 10, 25, 50, 100, 150 or 200 substitutions. The polynucleotide of SEQ ID NO: 1, 4, 8 or 12 can alternatively or additionally be modified by one or more insertions and/or deletions and/or by an extension at either or both ends. Additional sequences such as signal sequences may also be included. The modified polynucleotide encodes a polypeptide which has the ability to inhibit bone resorption by osteoclasts. The modified polynucleotide may encode a polypeptide which has RANKL binding activity. The modified polynucleotide can encode any of the variants or fragments discussed above. Degenerate substitutions can be made and/or substitutions can be made which would result in a conservative amino acid substitution when the modified sequence is translated, for example as shown in the Table above.

A nucleotide sequence which is capable of selectively hybridizing to the complement of the DNA coding sequence of SEQ ID NO: 1, 4, 8 or 12 will generally have at least 60%, at least 70%, at least 80%, at least 90%, at least 95%, at least 98% or at least 99% sequence identity to the coding sequence of SEQ ID NO: 1, 4, 8 or 12 over a region of at least 20, preferably at least 30, for instance at least 40, at least 60, more preferably at least 100 contiguous nucleotides or most preferably over the full length of SEQ ID NO: 1, 4, 8 or 12 or the length of SEQ ID NO: 1, 4, 8 or 12 encoding a polypeptide having the sequence shown in SEQ ID NO: 2, 5, 9 or 13. Sequence identity can be determined by any suitable method, for example as described above.

Any combination of the above mentioned degrees of sequence identity and minimum sizes can be used to define polynucleotides of the invention, with the more stringent combinations (i.e. higher sequence identity over longer lengths) being preferred. Thus, for example a polynucleotide which has at least 90% sequence identity over 20, preferably over 30 nucleotides forms one aspect of the invention, as does a polynucleotide which has at least 95% sequence identity over 40 nucleotides.

Polynucleotide fragments will preferably be at least 10, preferably at least 15 or at least 20, for example at least 25, at least 30 or at least 40 nucleotides in length. They will typically be up to 40, 50, 60, 70, 100 or 150 nucleotides in length. Fragments can be longer than 150 nucleotides in length, for example up to 200, 300, 400, 500, 600, 700, 800, 900 or 1000 nucleotides in length, or even up to a few nucleotides, such as five, ten or fifteen nucleotides, short of the coding sequence of SEQ ID NO: 1, 4, 8 or 12.

Polynucleotides for use in the invention can be produced recombinantly, synthetically, or by any means available to those of skill in the art. They can also be cloned by standard techniques. The polynucleotides are typically provided in isolated and/or purified form.

In general, short polynucleotides will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the TSG-6 gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the TSG-6 gene sequence described herein. Although in general the techniques mentioned herein are well known in the art, reference may be made in particular to Sambrook et al., 2001, Molecular Cloning: a laboratory manual, $3^{rd}$ edition, Cold Harbour Laboratory Press.

TSG-6 polynucleotides as described herein have utility in production of the polypeptides for use in the present invention, which may take place in vitro, in vivo or ex vivo. The polynucleotides can be used as therapeutic agents in their own right or can be involved in recombinant protein synthesis.

The polynucleotides for use in the invention are typically incorporated into a recombinant replicable vector. The vector may be used to replicate the nucleic acid in a compatible host cell. Therefore, polynucleotides for use in the invention can be made by introducing a TSG-6 polynucleotide into a replicable vector, introducing the vector into a compatible host cell and growing the host cell under conditions which bring about replication of the vector.

Preferably the vector is an expression vector comprising a nucleic acid sequence that encodes a TSG-6 polypeptide. Such expression vectors are routinely constructed in the art of molecular biology and may for example involve the use of plasmid DNA and appropriate initiators, promoters, enhancers and other elements, such as for example polyadenylation signals, which may be necessary and which are positioned in the correct orientation in order to allow for protein expression. Other suitable vectors would be apparent to persons skilled in the art. By way of further example in this regard we refer to Sambrook et al., 2001, Molecular Cloning: a laboratory manual, 3$^{rd}$ edition, Cold Harbour Laboratory Press.

Preferably, a polynucleotide for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors can be for example, plasmid, virus or phage vectors provided with an origin of replication, optionally a promoter for the expression of the said polynucleotide and optionally a regulator of the promoter. The vector is typically adapted to be used in vivo.

Promoters and other expression regulation signals can be selected to be compatible with the host cell for which expression is designed. Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

The vector can further include sequences flanking the polynucleotide giving rise to polynucleotides which comprise sequences homologous to eukaryotic genomic sequences, preferably mammalian genomic sequences. This will allow the introduction of the polynucleotides of the invention into the genome of eukaryotic cells by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

OPG Polypeptides

An OPG polypeptide may be administered in combination with a TSG-6 polypeptide. The OPG polypeptide is preferably human OPG, or a variant or fragment of human OPG which retains RANKL binding activity. The OPG polypeptide may have the ability to inhibit bone resorption by osteoclasts. The variant can be an OPG polypeptide from another organism, such as a primate, a mouse or a rat.

The OPG polypeptide preferably comprises:

(a) the amino acid sequence of SEQ ID NO: 15;

(b) a variant thereof having at least 50% identity to the amino acid sequence of SEQ ID NO: 15 and having receptor activator of RANKL binding activity; or (c) a fragment of either (a) or (b) having RANKL binding activity.

The OPG polypeptide may comprise, or consist of, the sequence of SEQ ID NO: 15.

Typically, polypeptides with more than about 50%, 55% or 65% identity, preferably at least 70%, at least 80%, at least 90% and particularly preferably at least 95%, at least 97% or at least 99% identity, with the amino acid sequence of SEQ ID NO: 15 are considered variants of the OPG protein. Such variants include allelic variants and the deletion, modification or addition of single amino acids or groups of amino acids within the protein sequence, as long as the peptide maintains the basic functionality of OPG. The identity of variants of SEQ ID NO: 15 can be measured over various regions of SEQ ID NO: 15 as discussed above for TSG-6. The variant sequences typically differ from SEQ ID NO: 15 by one or more mutations as discussed above for TSG-6.

The fragment of the OPG polypeptide used in the invention retains the function of OPG. The fragment polypeptides may therefore inhibit bone resorption by osteoclasts. The fragment polypeptides may bind to RANKL.

The binding activity of the fragment polypeptides can be modified as discussed above for TSG-6.

The fragment of the OPG polypeptide used in the invention is typically at least 10 amino acids in length as discussed above for TSG-6.

The OPG polypeptides used in the invention may be chemically modified as discussed above for TSG-6.

The RANKL binding activity and the osteoclast inhibitory activity of the OPG polypeptide can be determined as discussed above for TSG-6.

OPG polypeptides for use in the invention may be in a substantially isolated form as discussed above for TSG-6. They may be natural polypeptides or be made synthetically or by recombinant means as discussed above for TSG-6.

The amino acid sequence of OPG polypeptides for use in the invention may be modified as discussed above for TSG-6.

OPG Polynucleotides

A polynucleotide encoding an OPG polypeptide, variant or fragment may be administered in combination with TSG-6. The polynucleotide may comprise or consist of: (a) the coding sequence of SEQ ID NO: 14; (b) a sequence which is degenerate as a result of the genetic code to the sequence as defined in (a); (c) a sequence having at least 60% identity to a sequence as defined in (a) or (b) and which encodes a polypeptide having RANKL binding activity; or (d) a fragment of any one of the sequences as defined in (a), (b) or (c) which encodes a polypeptide having RANKL binding activity. The polynucleotide may comprise or consist of: (a) the coding sequence of SEQ ID NO: 14; (b) a sequence which is degenerate as a result of the genetic code to the sequence as defined in (a); (c) a sequence having at least 60% identity to a sequence as defined in (a) or (b) and which encodes a polypeptide having the ability to inhibit bone resorption by osteoclasts; or (d) a fragment of any one of the sequences as defined in (a), (b) or (c) which encodes a polypeptide having the ability to inhibit bone resorption by osteoclasts.

Typically the OPG polynucleotide is DNA. However, the polynucleotide may be a RNA polynucleotide. The polynucleotide may be single or double stranded, and may include within it synthetic or modified nucleotides.

An OPG polynucleotide can typically hybridize to the coding sequence or the complement of the coding sequence of SEQ ID NO: 14 as discussed above for TSG-6. The coding sequence of SEQ ID NO: 14 can be modified as discussed above for TSG-6.

A nucleotide sequence which is capable of selectively hybridizing to the complement of the DNA coding sequence of SEQ ID NO: 14 will generally have at least 60% identity to the coding sequence of SEQ ID NO: 14 over a region of at least 20 contiguous nucleotides or most preferably over the full length of SEQ ID NO: 14 or the length of SEQ ID NO: 14 encoding a polypeptide having the sequence shown in SEQ ID NO: 15 as discussed above for TSG-6.

Polynucleotide fragments will preferably be at least 10 nucleotides in length as discussed above for TSG-6.

OPG polynucleotides for use in the invention can be produced by any means discussed above for TSG-6. They can also be used to produce OPD polypeptides as discussed above for TSG-6.

OPG Mimetics

An OPG mimetic may be administered in combination with a TSG-6 polypeptide. An OPG mimetic may be a factor that inhibits bone resorption by osteoclasts by binding to and inhibiting RANKL.

The OPG mimetic can be a polypeptide, such as an antibody. The OPG mimetic is preferably AMG-162, which is Amgen's monoclonal antibody that binds to and inhibits RANKL. Alternatively, the OPG mimetic can be a polynucleotide which encodes a polypeptide that inhibits bone resorption by osteoclasts by binding to and inhibiting RANKL.

Diseases and Conditions

In accordance with some aspects of the invention, a TSG-6 polypeptide, or polynucleotide may be used to treat or prevent diseases or conditions associated with bone resorption by osteoclasts. Bone resorption by osteoclasts is the breakdown of bone matrix and mineral by osteoclasts cells. A disease or condition associated with bone resorption by osteoclasts is a disease or condition in which the rate of bone resorption by osteoclasts is abnormal. A disease or condition associated with bone resorption by osteoclasts is a disease or condition in which osteoclasts resorb (break down) bone at a greater rate than the rate of bone resorption (break down) observed in comparable subjects in the absence of the disease or condition. The disease or condition involves an increase in the rate of bone resorption by osteoclasts.

The disease or condition can involve a rate of bone resorption that is greater than the rate of bone formation in the same subject. The disease or condition can therefore involve a net bone loss. Alternatively, the disease or condition can involve a rate of bone resorption that is the same as or less than the rate of bone formation in the same subject. The disease or condition can involve no net bone loss. The disease or condition can involve net bone gain. The disease or condition can involve a slower rate of net bone gain compared with the rate of net bone gain observed in comparable subjects without the disease or condition.

The disease or condition may be osteoarthritis, osteoporosis, bone cancer, a bone lesion associated with metastatic cancer, Paget's disease, Gorham Stout disease, primary hyperparathyroidism, periodontal disease, a bone fracture and/or aseptic loosening of joint replacements. The bone cancer can be Ewing sarcoma, multiple myeloma, osteosarcoma (giant tumour of the bone) and/or osteoclastoma. The metastatic cancer that results in a bone lesion can be breast cancer, prostate cancer, kidney cancer, lung cancer and/or adult T-cell leukemia.

The subject is typically a mammalian subject, such as a mouse, rat or primate (e.g. a marmoset or monkey). The subject can be human or a non-human animal. Where the subject is a laboratory animal such as a mouse, rat or primate, the animal can be treated to induce a disease or condition associated with bone resorption by osteoclasts. The following Table summarizes whether an animal model for a disease or condition associated with bone resorption by osteoclasts exists or how a disease or condition associated with bone resorption by osteoclasts can be induced in an animal model.

| Disease or condition | Model/Induction |
|---|---|
| Osteoarthritis | Partial lateral meniscectomy in the knees of rabbits/mice or STR/ort mouse model |
| Osteoporosis | Ovariectomization of rodents such as rats |
| Ewing sarcoma | Injection of primary tumor cells into immune-deficient mice e.g. NOD or SCID |
| Multiple myeloma | 5T2MM mouse model |
| Osteosarcoma | Injection of TE-85 osteosarcoma cell line into tibia of athymic mice |
| Breast cancer | Implantation of mouse cancer cells 4T1/luc at the mammary fat pad, or injection of MDA-MD-231 human breast cancer cell line into nude mice |
| Kidney | Injection of RBM1 renal cancer cell line into nude mice |
| Lung | Injection of POS-1 cell line into C3H/He mice |
| Prostate | Injection of 22Rv1 prostate cancer cells into SCID mice |
| Adult T-cell leukaemia | HTLV-1 Tax transgenic mouse model |
| Primary hyperparathyroidism | PTH-targeted over-expression of cyclin D1 in transgenic mice |
| Periodontal diseases | Naturally occurring beagle dog model of periodontitis |
| Bone fracture | Wistar rat model of femoral fracture |
| Aseptic loosening of joint replacements | Weight-bearing rat pin model |

In some aspects of the present invention the disease or condition may be a disease or condition associated with one or more of joint destruction, cartilage degradation, damage to cartilage tissue and loss or degeneration of cartilage tissue. Cartilage degradation, damage or loss may involve a reduction in cartilage thickness or volume.

Joint destruction, cartilage degradation, damage to cartilage tissue and/or loss or degeneration of cartilage tissue may occur as a result of disease processes, physiological processes and/or as a result of injury or trauma. For example, joint destruction, cartilage degradation, damage to cartilage tissue and/or loss or degeneration of cartilage tissue may be initiated as a results of injury or trauma, and one or more of these processes may then proceed through disease and/or physiological processes.

The disease or condition may be arthritis, optionally trauma or injury-induced arthritis, age-related arthritis or non-age-related arthritis. The arthritis may be ostoearthritis. Osteoarthritis is a clinical syndrome of joint pain and reduced function of the joint (for example, stiffness and/or reduced range of motion). Symptoms include joint pain, stiffness and problems moving the joint. It may be characterised pathologically by localised loss of cartilage, remodeling of bone and/or inflammation. Joints most commonly affected by arthritis are knee joints, hip joints and joints in the hands and feet, but other joints can also be affected.

The disease or condition may be sports injury, rheumatoid arthritis (RA), spondyloarthritis, gout, psoriatic arthritis, ankylosing spondylitis (AS), systemic lupus erythematosus (SLE), systemic sclerosis, calcium crystal disease or Paget's disease.

The subject to be treated in accordance with the methods of the invention may be susceptible to one or more of joint destruction, cartilage degradation, damage to cartilage tissue and loss or degeneration of cartilage tissue even if these processes have not yet commenced. The subject may be susceptible as a result of having a disease or condition associated with one or more of joint destruction, cartilage degradation, damage to cartilage tissue and loss or degeneration of cartilage tissue.

Processes of Cartilage Loss, Degeneration, Degradation or Damage

Cartilage may be damaged or degraded as a result of physical processes such as injury or trauma, or mechanical wear and tear and/or biological processes such as disease and physiological processes. Physical processes and biological processes interact to bring about loss, degeneration, degradation or damage of cartilage. For example, injury or trauma or mechanical wear and tear can initiate cartilage damage and engage, for example through inflammation, biological processes that effect and accelerate loss, degeneration, degradation or damage of cartilage.

Injury or trauma may be the result of a fall or sports-related injury or trauma. Mechanical wear and tear may be associated with obesity and/or repetitive actions. For example, mechanical wear and tear may occur as a result of a particular activity or be associated with a particular occupation.

Effectors of biological processes resulting in the loss, degeneration, degradation or damage of cartilage include proteases, metalloproteases, cartilage degrading enzymes upregulated in response to inflammatory mediators, aggrecanases, collagenases, ADAMTS-4, ADAMTS-5, MMP3 and MMP13. Increased catabolic activity of chondrocytes is associated with biological processes resulting in the loss, degeneration, degradation or damage of cartilage. Metabolic activity of chondrocytes can be assayed, for example, by analysis of expression of cartilage genes such as SOX-9, COLII, AGGRECAN, COL1 and TSG-6, or incorporation of radiolabel.

Metabolic Activity of Chondrocytes

In some embodiments the polypeptide or polynucleotide of the invention is useful to effect a change in the metabolic activity of chondrocytes. In some embodiments, Link_TSG6 is capable of downregulating the expression of genes associated with catabolic activity of chondrocytes. Genes associated with catabolic activity include enzymes resulting in and/or promoting the degradation of cartilage, including cartilage degrading enzymes such as aggrecanase and collagenase. Inhibition of catabolic activity of chondrocytes can be determined by the detection of a decrease in the expression or activity of one or more genes associated with catabolic activity of chondrocytes following treatment with Link_TSG6 polypeptide or polynucleotide relative to an untreated control.

Similarly, in some embodiments Link_TSG6 is capable of upregulating the expression of genes associated with anabolic activity of chondrocytes. For example, Link_TSG6 is capable of upregulating the expression of genes associated with the production and/or maintenance of cartilage. Genes associated with anabolic activity of chondrocytes include genes involved in the production or maintenance of cartilage tissue, for example genes for production of cartilage matrix molecules, such as aggrecan. In some embodiments, Link_TSG6 is capable of upregulating the expression of genes associated with protecting cartilage from degradation. Promotion of anabolic activity of chondrocytes can be determined by the detection of an increase in the expression or activity of one or more genes associated with anabolic activity of chondrocytes following treatment with Link_TSG6 polypeptide or polynucleotide relative to an untreated control.

In some embodiments, Link_TSG6 is capable of promoting anabolic activity and inhibiting catabolic activity of chondrocytes. In some embodiments, Link_TSG6 is capable of effecting a change in the metabolic state of a chondrocyte from a catabolic state to an anabolic state. In some embodiments, a change in the metabolic activity of chondrocytes from a catabolic state to an anabolic state can be determined by detection of a relative decrease in the expression or activity of one or more genes associated with catabolic activity, and detection of an increase in the expression or activity of one or more genes associated with anabolic activity of chondrocytes following treatment with Link_TSG6 polypeptide or polynucleotide relative to an untreated control.

Determining Loss/Degeneration/Degradation/Damage of Cartilage

Loss, degeneration, degradation, damage or maintenance of cartilage can be determined by imaging cartilage and/or measuring cartilage over time. Imaging and/or measuring of cartilage may be at a site of interest, for example a site of injury or trauma, or an arthritic joint.

Cartilage loss, degeneration, degradation or damage can be determined by routine methods well known to those skilled in the art. For example, defects (i.e. damage) in cartilage or cartilage loss may be determined by magnetic resonance imaging (MRI) or by arthroscopy.

Cartilage loss, degeneration or degradation can be determined by observation of a reduced amount of cartilage in a joint or at a location relative to a previous measurement of the amount of cartilage in that joint or at that location. Alternatively, cartilage loss, degeneration or degradation can be determined by observation of a reduced amount, thickness or volume of cartilage in a joint or at a location relative to an equivalent joint or location not experiencing cartilage loss, degeneration or degradation.

Damage to cartilage observed by arthroscopy may be graded according to the International Cartilage Repair Society (ICRS) grading system, as follows:

0=(normal) healthy cartilage;
1=the cartilage has a soft spot or blisters
2=minor tears visible in the cartilage
3=lesions have deep crevices (more than 50% of the cartilage layer)
4=the cartilage tears exposes the underlying (subchondral) bone.

Cartilage of grade 2/3 defects may have a fibrillated or shredded appearance.

Damage to cartilage can also be assessed by histopathology according to the Osteoarthritis Research Society International (OARSI) grading system described in Pritzker et al., Osteoarthritis Cartilage 2006 14(1): 13-29, as follows:

| Grade (key feature) | Subgrade (optional) | Associated cristeria (tissue reaction) |
|---|---|---|
| Grade 0: surface intact, cartilage intact | — | Intact, uninvolved cartilage |
| Grade 1: surface intact | 1.0 Cells intact | Matrix: superficial zone intact, edema and/or fibrillation |
| | 1.5 Cell death | Cells: proliferation (clusters), hypertrophy |
| | — | Reaction must be more than superficial fibrillation only |

| Grade (key feature) | Subgrade (optional) | Associated cristeria (tissue reaction) |
| --- | --- | --- |
| Grade 2: surface discontinuity | 2.0 Fibrillation through superficial zone | As above |
| | 2.5 Surface abrasion with matrix loss within superficial zone | +Discontinuity at superficial zone ±Cationic stain matrix depletion (Safranin O orToluidine Blue) upper ⅓ of cartilage (mid zone) |
| | — | ±Disorientation of chondron columns |
| Grade 3: vertical fissures | 3.0 Simple fissures | As above |
| | 3.5 Branched/complex fissures | ±Cationic stain depletion (Safranin O or Toluidine Blue) into lower ⅔ of cartilage (deep zone) |
| | — | ±New collagen formation (polarized light microscopy, Picro Sirius Red stain) |
| Grade 4: erosion | 4.0 Superficial zone delamination | Cartilage matrix loss, cyst formation within cartilage matrix |
| | 4.5 Mid zone excavation | |
| Grade 5: denudation | 5.0 Bone surface intact 5.5 Reparative tissue surface present | Surface is sclerotic bone or reparative tissue including fibrocartilage |
| Grade 6: deformation | 6.0 Joint margin osteophytes | Bone remodelling. Deformation of articular surface contour (more than osteophyte formation only) |
| | 6.5 Joint margin and central osteophytes | Includes: microfracture and repair |

Expression and/or activity of enzymes associated with cartilage degradation, or of genes or enzymes known to be upregulated in response to cartilage degradation can also be used to determine loss, degeneration, degradation, damage or maintenance of cartilage. Similarly, catabolic activity of chondrocytes can be assayed to investigate loss, degeneration, degradation, damage or maintenance of cartilage.

Inhibition of joint destruction or cartilage degradation, or prevention or delay of degradation of or damage to or loss of cartilage tissue, or maintenance of effective cartilage tissue as a result of administration of a therapeutically effective amount of a polypeptide or polynucleotide of the invention can be determined by finding no or minimal loss, degeneration, degradation or damage of cartilage in a joint or at a location, relative to a previous measurement of the amount of cartilage in that joint or at that location. Alternatively, inhibition of joint destruction or cartilage degradation, or prevention or delay of degradation of or damage to or loss of cartilage tissue, or maintenance of effective cartilage tissue can be determined by finding reduced or slowed loss, degeneration, degradation or damage of cartilage in a joint or at a location relative to an untreated control joint or location.

Gene expression—e.g. of genes associated with cartilage loss, degeneration, degradation or damage, or TSG-6—can be determined by a variety of methods well known to the skilled person. For example, the level of expression of a gene can be determined in a sample, e.g. a biopsy or tissue sample, by quantitative real-time PCR.

Genes associated with cartilage loss include, but are not limited to, genes encoding proteases, metalloproteases, cartilage degrading enzymes upregulated in response to inflammatory mediators, aggrecanases, collagenases, ADAMTS-4, ADAMTS-5, MMP3 and MMP13.

The level of expression or activity of a protein or enzyme e.g. associated with cartilage loss, degeneration, degradation or damage can be determined by routine methods know to the skilled person. For example, the level of expression of a protein in a sample, e.g. a biopsy or tissue sample, can be determined by immunoblot. The level of activity of an enzyme can be determined in a sample, e.g. a biopsy or tissue sample, by using a reporter assay for the activity of that enzyme. Similarly, the metabolic activity of chondrocytes in a sample e.g. a biopsy or tissue sample can be determined.

Cartilage degradation/destruction/loss/damage and/or joint destruction can be correlated with clinical symptoms of a disease or condition associated with loss, degeneration, degradation or damage to cartilage tissue or joint destruction, and so these may also be useful for investigating or estimating cartilage degradation/destruction/loss/damage or joint destruction, metabolic activity of chondrocytes, or expression and/or activity of cartilage degrading enzymes.

Therapy and Prophylaxis

The present invention provides the use of TSG-6 polypeptides and polynucleotides to treat or prevent a disease or condition associated with bone resorption by osteoclasts or a disease or condition associated with one or more of joint destruction, cartilage degradation, damage to cartilage tissue and loss or degeneration of cartilage tissue. Treatment can be therapeutic or prophylactic.

The TSG-6 polypeptide or polynucleotide can be administered to an individual in order to prevent the onset of one or more symptoms of the disease or condition. In this embodiment, the subject can be asymptomatic. The subject can have a genetic predisposition to the disease. A prophylactically effective amount of the polypeptide or polynucleotide is administered to such an individual. A prophylactically effective amount is an amount which prevents the onset of one or more symptoms of a disease or condition.

A therapeutically effective amount of the TSG-6 polypeptide or polynucleotide is an amount effective to ameliorate one or more symptoms of a disease or condition. Preferably, the individual to be treated is human.

The TSG-6 polypeptide or polynucleotide can be administered to the subject by any suitable means. The polypeptide or polynucleotide can be administered by enteral or parenteral routes such as via oral, buccal, anal, pulmonary, intravenous, intra-arterial, intramuscular, intraperitoneal, intraarticular, topical or other appropriate administration routes.

The TSG-6 polypeptide or polynucleotide may be administered to the subject in such a way as to target therapy to a particular site. For example, the TSG-6 polypeptide may be injected locally onto the surface of bone or into a joint. The TSG-6 polypeptide may be conjugated with reagents that bind bone, osteoclasts or chondrocytes specifically. For TSG-6 polynucleotides, expression vectors encoding the TSG-6 polypeptide may be used to direct expression of TSG-6 to a particular tissue, for example by using tissue-specific promoters or RNAi.

The formulation of any of the polypeptides and polynucleotides mentioned herein will depend upon factors such as the nature of the polypeptide or polynucleotide and the condition to be treated. The polypeptide or polynucleotide may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The polypeptide or polynucleotide may also be administered as suppositories. A physician will be able to determine the required route of administration for each particular patient.

Typically the polypeptide or polynucleotide is formulated for use with a pharmaceutically acceptable carrier or diluent and this may be carried out using routine methods in the pharmaceutical art. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to a patient may be provided with an enteric coating comprising, for example, Eudragit "5", Eudragit "L", cellulose acetate, cellulose acetate phthalate or hydroxypropylmethyl cellulose.

Pharmaceutical compositions suitable for delivery by needleless injection, for example, transdermally, may also be used.

A therapeutically effective amount of polypeptide or polynucleotide is administered. The dose may be determined according to various parameters, especially according to the polypeptide or polynucleotide used; the age, weight and condition of the patient to be treated; the route of administration; and the required regimen. Again, a physician will be able to determine the required route of administration and dosage for any particular patient. A typical daily dose is from about 0.1 to 50 mg per kg, preferably from about 0.1 mg/kg to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The TSG-6 nucleotide sequences described above and expression vectors containing such sequences can also be used as pharmaceutical formulations as outlined above. Preferably, the nucleic acid, such as RNA or DNA, in particular DNA, is provided in the form of an expression vector, which may be expressed in the cells of the individual to be treated. The vaccines may comprise naked nucleotide sequences or be in combination with cationic lipids, polymers or targeting systems. The vaccines may be delivered by any available technique. For example, the nucleic acid may be introduced by needle injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to mucosal surfaces for example by intranasal, oral, intravaginal or intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg or 1 mg, preferably to 1 pg to 10 µg nucleic acid for particle mediated gene delivery and 10 µg to 1 mg for other routes.

The present invention also provides a method of treating, ex vivo, blood taken from a patient suffering from a disease or condition associated with bone resorption by osteoclasts, or a disease or condition associated with one or more of joint destruction, cartilage degradation, damage to cartilage tissue and loss or degeneration of cartilage tissue, comprising contacting the blood with a TSG-6 polypeptide. TSG-6 may thus be used for extracorporeal treatment of blood. The TSG-6 may be used to treat one or more components of blood, such as plasma or serum. The ex vivo method described herein may be practised on blood that has already been removed from the body of a patient. The blood or blood product may optionally be returned to the patient after being contacted with a TSG-6 polypeptide.

A chondroprotective composition is a therapeutic or prophylactic composition which is useful to prevent, delay or treat joint destruction. Chondroprotective agents include, but are not limited to, agents capable of stimulating synthesis of collagen, proteoglycans or hyaluronan, agents capable of inhibiting cartilage degradation and agents capable of inhibiting fibrin formation.

Administration of the polypeptide or polynucleotide of the invention may be locally to a site of interest, for example a site where injury or trauma has occurred, and/or a site known to be susceptible to or experiencing loss or degeneration of cartilage tissue.

Administration of the polypeptide or polynucleotide of the invention may be commenced immediately after injury or trauma, for example within 30 minutes, within 1 hour, within 2 hours, within 6 hours, within 12 hours, within 28 hours, within 48 hours, within 72 hours, within 1 week, within 2 weeks, within 3 weeks, within 1 month, within 2 months, or within 6 months of injury or trauma.

Administration of the polypeptide or polynucleotide of the invention can be continued for a defined period of time, for example at least 1 week, at least 2 weeks, at least 3 weeks, at least 1 month, at least 2 months, at least 3 months, at least 4 months, at least 6 months, at least 8 months, at least 10 months, at least 1 year, at least 18 months, at least 2 years, at least 3 years, at least 4 years, at least 5 years, at least 6 years, at least 7 years, at least 8 years, at least 9 years, at least 10 years. For example, administration may be continued for a period of between 1 week and 10 years, between 1 week and 9 years, between 1 week and 8 years, between 1 week and 7 years, between 1 week and 6 years, between 1 week and 5 years, between 1 week and 4 years, between 1 week and 3 years, between 1 week and 2 years, between 1 week and 18 months, between 1 week and 1 year, between 1 week and 6 months, between 1 week and 3 months, between 1 week and 2 months, between 1 week and 1 month, or between 1 week and 2 weeks from first administration.

During the course of administration of the polypeptide or polynucleotide of the invention, frequency of administration can be defined. For example, administration may be daily, every other day, three times per week, twice weekly, weekly, fortnightly, monthly, once every 6 weeks, once every two months, once every 3 months, once every 4 months, once every 5 months, once every 6 months, once every 8 months, once every 9 months, once every 10 months, or once every year.

The dose, schedule, mode or time course of administration of the polypeptide or polynucleotide of the invention can be modified according to response to therapy. For example, dose and/or the frequency of administration and/or time course of administration may be increased if response to therapy is suboptimal. Conversely, dose and/or the frequency of administration and/or time course of administration can be reduced if response to therapy is better than expected.

Response to therapy can be the determination of prevention, delay or treatment of loss, degeneration, degradation or damage to cartilage tissue or joint destruction, and/or reduction or inhibition of metabolic activity of chondrocytes, and/or reduction or inhibition of expression and/or activity of cartilage degrading enzymes.

Response to therapy can be measured using any parameter associated with loss, degeneration, degradation or damage to cartilage tissue or joint destruction and/or reduction or inhibition of metabolic activity of chondrocytes, and/or reduction or inhibition of expression and/or activity of cartilage degrading enzymes. For example, response to therapy can be determined by one or more of: imaging or measuring of cartilage or cartilage defects, measuring expression and/or activity of enzymes associated with cartilage degradation (e.g. aggrecanases and/or collagenases) or of genes or enzymes known to be upregulated in response to cartilage degradation, measuring metabolic activity of chondrocytes, or evaluation of clinical symptoms of a disease or condition associated with loss, degeneration, degradation or damage to cartilage tissue or joint destruction.

Patient Selection

In accordance with the methods of the invention, the methods may additionally comprise the step of selecting a subject for treatment with a therapeutically effective amount of a polypeptide comprising or consisting of Link_TSG6 or a therapeutically effective amount of a polynucleotide encoding Link_TSG6.

The methods may comprise evaluating a subject for evidence of, or susceptibility to, joint destruction, cartilage degradation, damage to cartilage tissue, loss or degeneration of cartilage tissue, trauma or injury to a joint, wherein a subject identified as having or being susceptible to joint destruction, cartilage degradation, damage to cartilage tissue, loss or degeneration of cartilage tissue, trauma or injury to a joint is selected for treatment.

The methods may comprise evaluating of subject for the clinical symptoms of, or susceptibility to, osteoarthritis, wherein a subject identified as having or being susceptible to osteoarthritis is selected for treatment. Osteoarthritis may be trauma or injury induced osteoarthritis, age-related osteoarthritis or non-age related osteoarthritis.

The methods may comprise determining the level of metabolic activity of chondrocytes, or the level of expression of one or more cartilage degrading enzymes or TSG-6 in a subject, wherein a subject identified as having increased metabolic activity of chondrocytes compared to a reference metabolic activity of chondrocytes, or increased expression of one or more cartilage degrading enzymes compared to a reference level of expression of one or more cartilage degrading enzymes or decreased expression of TSG-6 compared to a reference level of TSG-6 expression is selected for treatment. The reference level of metabolic activity of chondrocytes and/or reference level expression of one or more cartilage degrading enzymes and/or reference level of TSG-6 expression may be those levels associated with a healthy state. For example, the reference levels may be levels of activity/expression in a healthy subject.

The evaluating and/or determining steps may be performed on a subject. The methods may comprise measuring cartilage, for example by MRI or arthroscopy, or measuring the range of motion of a joint or stiffness of a joint.

The methods may comprise grading cartilage defects according to the ICRS or OARSI grading system. The subject may be evaluated by arthroscopy for defects which are graded according to the ICRS grading system, and based on the grading selecting a subject for administration of a therapeutically effective amount of a polypeptide comprising or consisting of Link_TSG6 or a therapeutically effective amount of a polynucleotide encoding Link_TSG6. For example, a subject having a defect having a grading of 0 or more, 1 or more, 2 or more, 3 or more or 4 on the ICRS grading system may be selected.

The evaluating and/or determining steps may be performed on a sample obtained from the subject. Accordingly, in some embodiments the methods comprise obtaining a sample from a subject, performing one or more measurements on the sample, and based on the result of the one or more measurements selecting a subject for administration of a therapeutically effective amount of a polypeptide comprising or consisting of Link_TSG6 or a therapeutically effective amount of a polynucleotide encoding Link_TSG6. The methods may comprise measuring cartilage, chondrocyte metabolic activity or enzyme or TSG-6 expression or activity in the sample obtained from the subject.

In some embodiments, the sample may be obtained by arthroplastic surgery. The sample may be evaluated by histopathology for defects which are graded according to the OARSI grading system, and based on the grading selecting a subject for administration of a therapeutically effective amount of a polypeptide comprising or consisting of Link__TSG6 or a therapeutically effective amount of a polynucleotide encoding Link_TSG6. For example, a subject having a defect having a grading of 0 or more, 1 or more, 2 or more, 3 or more, 4 or more, 5 or more or 6 on the OARSI grading system may be selected.

Evaluation of a subject for: evidence of, or susceptibility to, joint destruction, cartilage degradation, damage to cartilage tissue, loss or degeneration of cartilage tissue, trauma or injury to a joint; the clinical symptoms of, or susceptibility to, osteoarthritis; or the level of metabolic activity of chondrocytes, or the level of expression of one or more cartilage degrading enzymes or TSG-6, may be determined at any point before, during or after administration of a therapeutically effective amount of a polypeptide comprising or consisting of Link_TSG6 or a therapeutically effective amount of a polynucleotide encoding Link_TSG6. In some embodiments, the methods of the invention comprise commencing administration, evaluating a subject as above and based on the evaluation continuing, altering or discontinuing further administration. In some embodiments, altering administration comprises increasing or decreasing the dose and/or the frequency and/or the time course of administration.

Combination Therapy

The TSG-6 polypeptide or polynucleotide can be administered alone or in combination with other pharmaceutically active agents, in one embodiment, the TSG-6 polypeptide or polynucleotide is not administered in combination with long petraxin 3 (PTX3). In the same embodiment, the medicament manufactured in accordance with the invention does not comprise PTX3.

In some embodiments, the method further comprises administering to the subject a therapeutically or prophylactically effective amount of an OPG polypeptide, a polynucleotide encoding an OPG polypeptide or an OPG mimetic. In the same embodiment, the medicament is administered in combination with a therapeutically or prophylactically effective amount of an OPG polypeptide, a polynucleotide encoding an OPG polypeptide or an OPG mimetic.

The TSG-6 and OPG act synergistically. In other words, administering TSG-6 and OPG in combination has a greater effect on inhibiting bone resorption by osteoclasts than the sum of the effect of each alone.

A therapeutically effective amount of the OPG polypeptide, polynucleotide or an OPG mimetic is an amount effective to ameliorate one or more symptoms of a disease or condition. A prophylactically effective amount is an amount which prevents the onset of one or more symptoms of a disease or condition.

The TSG-6 and OPG can be administered simultaneously, separately or sequentially. If administered simultaneously, the TSG-6 and OPG can be present in the same medicament or different medicaments. If administered separately or sequentially, the TSG-6 and OPG can be administered in any order.

Typically, a TSG-6 polypeptide and an OPG polypeptide are administered together or a TSG-6 polynucleotide and an OPG polynucleotide are administered together. However, in some embodiments, the TSG-6 may be a polypeptide, while the OPG is a polynucleotide and vice versa.

The OPG polypeptide, the OPG polynucleotide or the OPG mimetic can be administered to the subject by any means, in any formulation and at any dose discussed above for TSG-6.

The polypeptide or polynucleotide of the invention may be administered simultaneously, separately or sequentially with a therapeutic or prophylactic intervention to prevent, delay or treat loss, degeneration, degradation, or damage to cartilage, or joint destruction, or to reduce or inhibit metabolic activity of chondrocytes, or to reduce or inhibit expression and/or activity of cartilage degrading enzymes. For example, administration may be simultaneously, separately or sequentially to surgery to replace damaged cartilage with healthy cartilage.

The following Examples illustrate the invention:

EXAMPLES

The following studies show that TSG-6 is a novel inhibitor of bone resorption and chondroprotective agent.

Example 1—Inhibition of Osteoclasts by TSG-6

Figure 1:
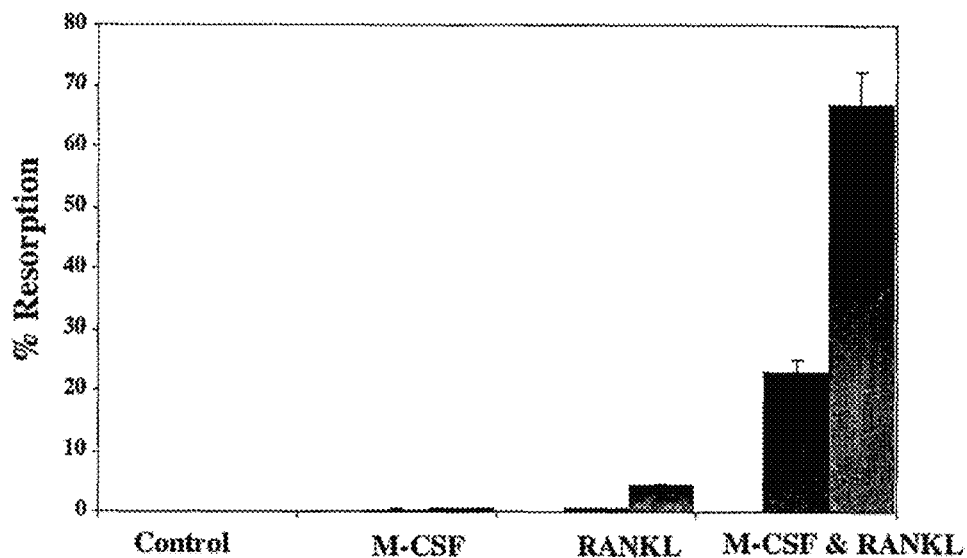
FIG. 1 shows the effect of TSG-6 on osteoclastogenesis. sRANKL/M-CSF-mediated human osteoclast formation was determined in the absence (lighter bars on the right hand side) and presence (darker bars on the left hand side) of recombinant human TSG-6 (25 ng/ml (0.8 nM)). Data (n=8 dentine slices) are expressed as mean values±S.E. of 2 independent experiments, of 4 replicates each.
Figure 2:
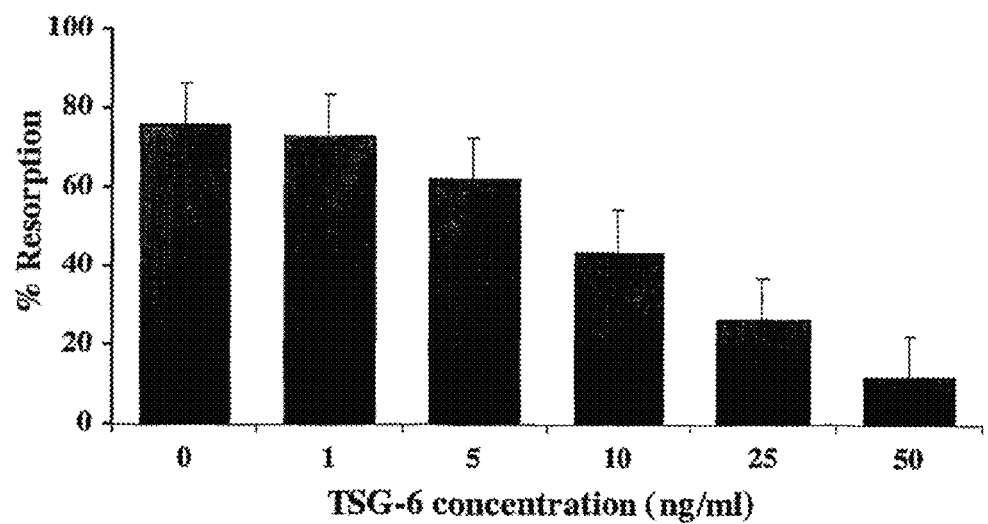
FIG. 2 shows the inhibitory effect of TSG-6 on lacunar resorption over a range of TSG-6 concentrations. Data (n=8 dentine slices) are expressed as mean values±S.E. of 2 independent experiments, of 4 replicates each.

The Q144 allotype of the full-length human TSG-6 protein (as shown in SEQ ID NO: 1) was expressed in *Drosophila* S2 cells as described in Nentwich et al. (2002) *J. Biol. Chem.* 277, 15354-15362. The effect of this recombinant protein on the differentiation of osteoclasts in vitro was determined. Human monocytes differentiated into osteoclasts and developed a bone-resorbing phenotype over a period of 21 days. Osteoclast activity was measured by determining the extent of lacunar resorption on dentine slices. Human monocytes were cultured in the presence of sRANKL (soluble receptor activator of NFKB ligand; 30 ng/ml) and/or M-CSF (25 ng/ml) and bone resorptive activity was measured in the presence or absence of recombinant TSG-6. The addition of TSG-6 to this culture system mediated a substantial reduction in dentine erosion (FIG. 1) and this effect is dose-dependent (FIG. 2). TSG-6 therefore inhibits bone resorption by osteoclasts.

Example 2—Osteoclast Activity in TSG-6 Knockout Mice

Figure 3:
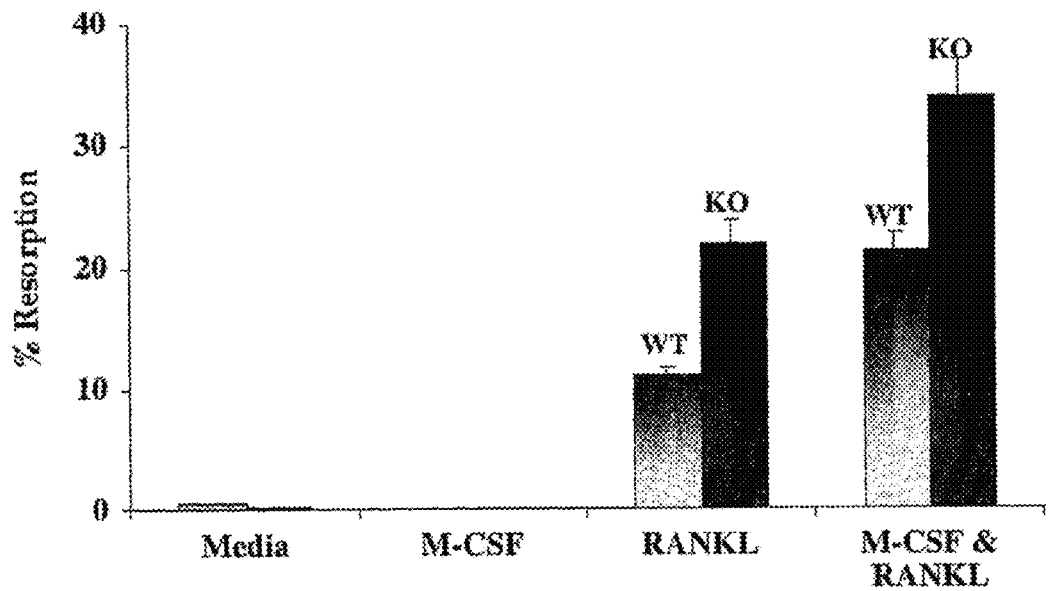
FIG. 3 shows a comparison of the bone resorptive activities of osteoclasts derived from bone marrow of wild-type (WT, left hand side bars) and TSG-6$^{-/-}$ mice (KO, right hand side bars). Data (n=4 dentine slices) are expressed as mean values±S.E. of 2 independent experiments, of 4 replicates.

The same experiment as in Example 1 was also carried out using osteoclast precursors from the long bones of TSG-6$^{-/-}$ mice. When cultured in the presence of sRANKL or M-CSF and sRANKL, the osteoclasts displayed markedly increased lacunar resorption in vitro as compared to cells from wild-type control animals (FIG. 3). These results are consistent with the more severe symptoms (e.g. bone erosion) seen in TSG-6-deficient animals following induction of PGIA. These studies indicate that TSG-6 is an important, novel inhibitor of osteoclastogenesis and/or osteoclast activation.

Example 3—TSG-6 Binding to RANKL

RANKL and its receptor RANK are key regulators of bone remodelling and have been specifically implicated in the bone loss that occurs in RA. RANKL is a membrane bound TNF-superfamily ligand that is produced by osteoblasts and other stromal cells, while RANK, a transmembrane signalling molecule, is expressed on the surfaces of mononuclear osteoclast precursors. RANKL binds to RANK, in response to calciotropic factors such as $PGE_2$, IL-1 and TNF, where this interaction not only induces osteoclast differentiation, but also stimulates the bone resorbing activity of mature osteoclasts (reviewed in Tanake et al. (2005) *Immunol. Rev.* 208, 30-49). Indeed, RANKL (in combination with M-CSF) is the major factor that regulates osteoclast differentiation (Quinn et al (1998) *Endocrinology* 139, 4424-4427).

At present, osteoprotegerin (OPG), a soluble decoy receptor to RANKL, is the only known inhibitor of the RANKL/RANK interaction that can effectively inhibit osteoclast maturation and activation in vitro (Simonet et al. (1997) *Cell* 89, 309-319), and a mimic of OPG activity (AMG 162) is currently in clinical trials for the treatment of osteoporosis.

RANKL is also expressed on the surfaces of synovial effector T cells from RA patients and studies on rats with AIA (which has many features in common with human RA) showed RANKL to be the key mediator of joint damage and bone erosion due to osteoclast accumulation, where treatment with OPG provided protection against these effects (Kong et al. (1999) *Nature* 402, 304-309).

Given the effects of TSG-6 on bone resorption described in Examples 1 and 2 above, the interaction of TSG-6 directly with RANKL was investigated. Recombinant full-length TSG-6 was expressed as described in Example 1. The isolated Link module domain (Link_TSG-6; SEQ ID NO: 9) was expressed in *E. coli* as described in Day et al. (1996) *Protein Express. Purif.* 8, 1-16. The CUB_C domain (CUB_C_TSG6; SEQ ID NO: 13) was expressed in *E. coli* (D J Mahoney and A J Day, unpublished). Full-length TSG-6, Link_TSG6 or CUB_C_TSG6 were coated onto microtitre plates at a range of concentrations and the binding of sRANKL (5 pmol/well) was determined using a RANKL-specific antibody.

Figure 4:
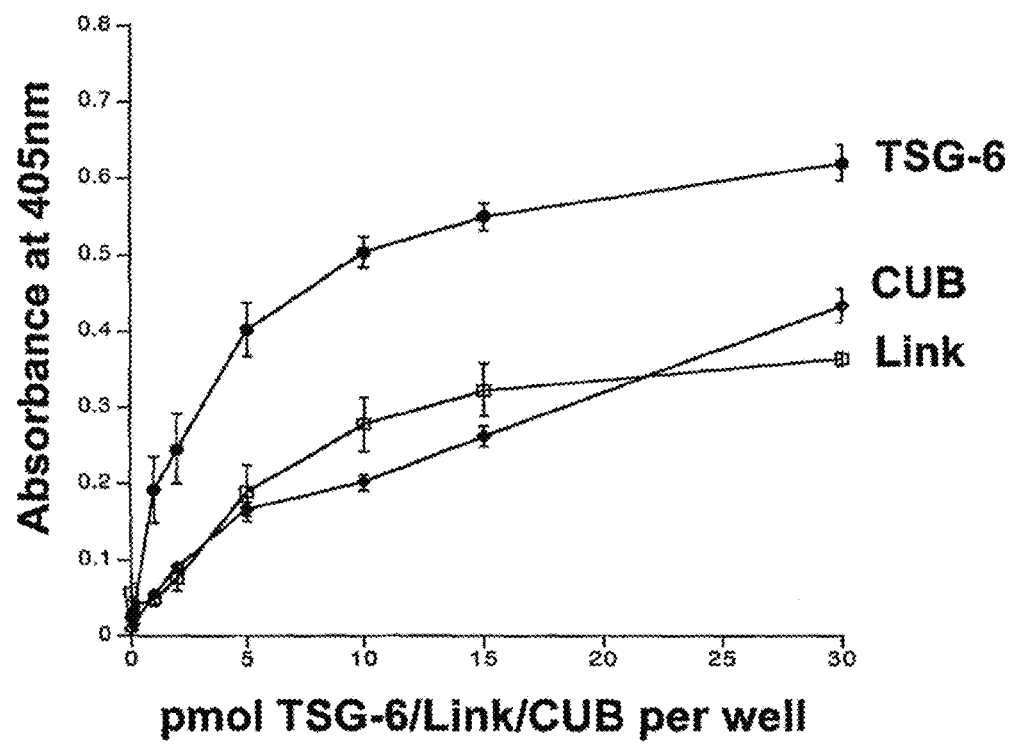
FIG. 4 shows the interaction of TSG-6 with sRANKL. Full-length TSG-6, Link_TSG6 or CUB_C_TSG6 were coated onto microtitre plates at a range of concentrations and the binding of sRANKL (5 pmol/well) was determined using a RANKL-specific antibody. All data are plotted as mean absorbance (405 nm) values (n=8)±S.E.

Results of plate-binding assays indicate that full-length TSG-6, its isolated Link module domain (Link_TSG6; SEQ ID NO: 9) and isolated CUB_C domain (CUB_C_TSG6; SEQ ID NO: 13) all bind to sRANKL but that the full-length TSG-6 has a higher binding affinity than the isolated domains (FIG. 4). This data suggests that TSG-6 might inhibit RANKL-induced osteoclastogenesis/osteoclast activation by its direct binding to RANKL, potentially in a similar manner to OPG.

Example 4—Synergy Between TSG-6 and OPG

Our data (not shown) indicates that TSG-6 in combination with OPG (a known inhibitor of RANKL) has a synergistic effect on the inhibition of osteoclast formation as determined by the number of tartrate-resistant acid phosphatase (TRAP+) multinucleated osteoclasts formed in culture (i.e., there is more inhibition of osteoclast formation in the presence of both TSG-6 and OPG compared to experiments where the individual proteins are present). One possible mechanism that could explain the synergistic action of TSG-6 and OPG is that both these proteins can bind simultaneously to RANKL forming a stable ternary complex.

Example 5—Link and CUB_C Domains of TSG-6 Inhibit Osteoclastogenesis

Moreover, our data (not shown) also shows that the isolated Link and CUB_C domains are inhibitors of osteoclastogenesis, albeit with less activity than the full-length protein. This indicates that these fragments of TSG-6 could be used as the basis for design of inhibitors of bone resorption.

Example 6—Levels of TSG-6 and OPG in Synovial Fluid

Figure 5:
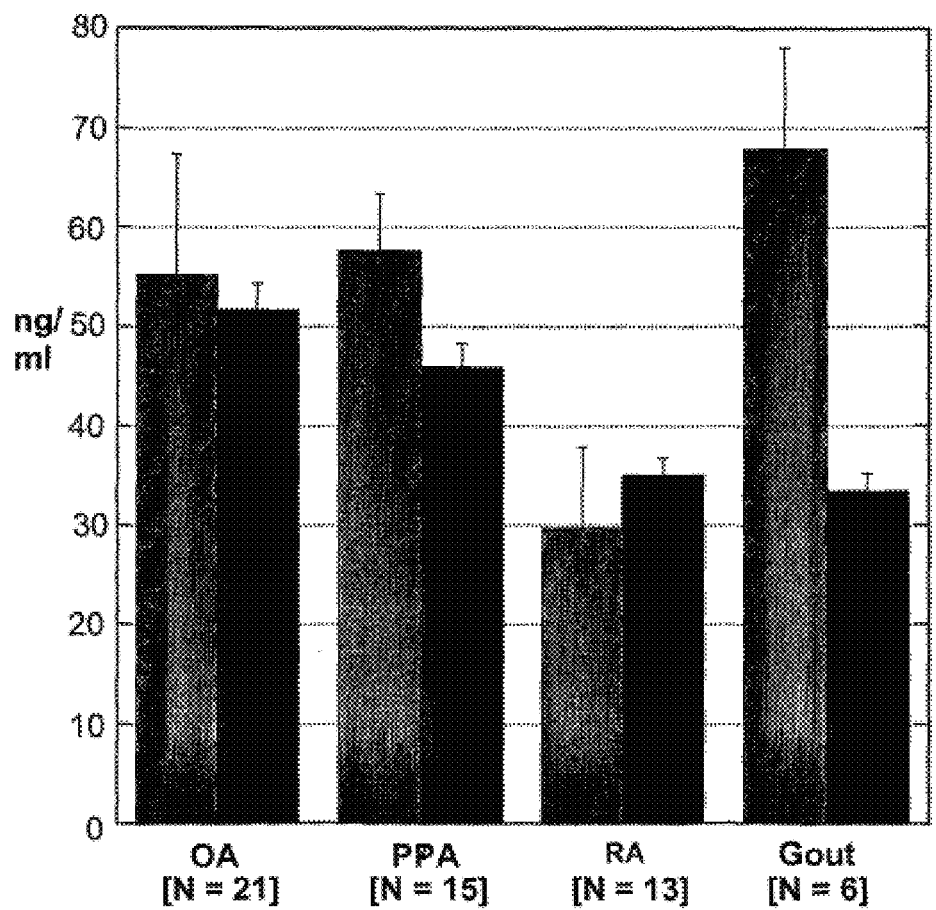
FIG. 5 shows quantification of TSG-6 and OPG in the synovial fluid from patients with various bone disorders. Protein levels in various bone disorders were determined using "in-house designed" ELISA assays. The levels of TSG-6 are shown in the lighter bars on the left hand side. The levels of OPG are shown in the darker bars on the right hand side. This Figure indicates variation in the levels of TSG-6 and OPG depending on the severity and stage of the bone diseases osteoarthritis (OA), pyrophosphate arthropathy (PPA), rheumatoid arthritis (RA) and gout. Each sample was assessed in triplicate and the number of synovial fluid samples for each condition is given (N number). The values are expressed as the mean±standard error of the mean for each group.
Figure 6:
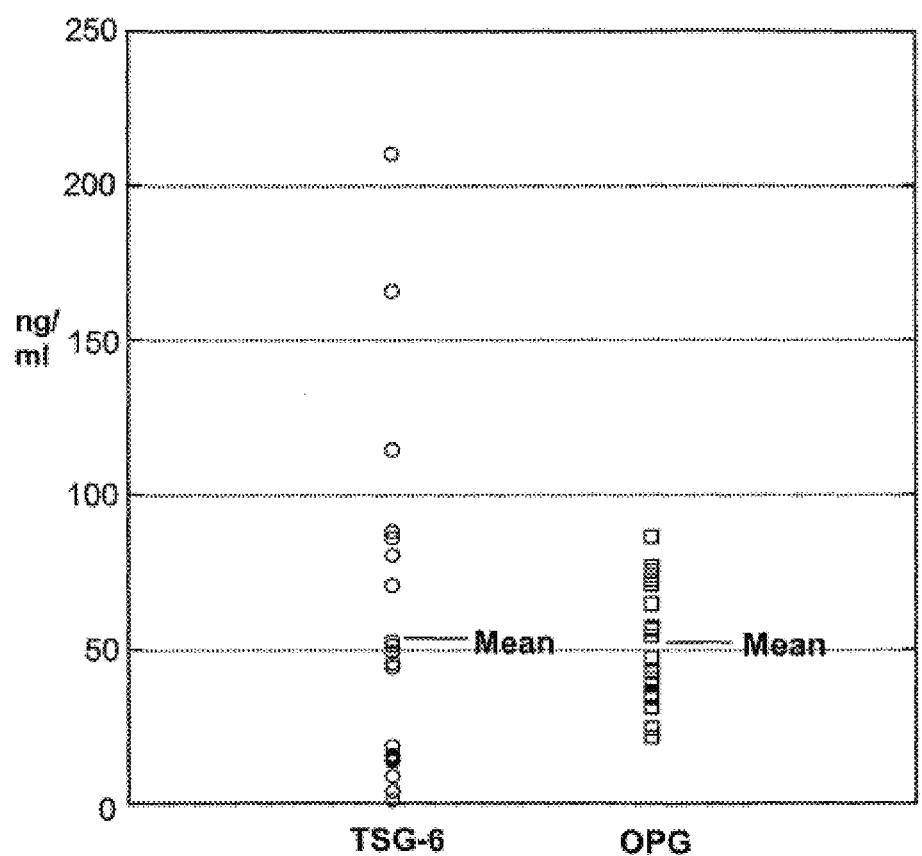
FIG. 6 shows a comparison between TSG-6 and OPG levels in the synovial fluid samples of osteoarthritis (OA) patients (n=20). This data demonstrates that variability in levels of TSG-6, as compared to OPG levels, could contribute to the extent and severity of disease.

We have measured high levels of TSG-6 (ranging from 0-200 ng/ml) in synovial fluid of patients with various bone disorders [e.g. osteoarthritis (OA), rheumatoid arthritis (RA), gout & pyrophosphate arthropathy (PPA); see FIG. 5). ELISA analyses of TSG-6 and OPG levels in OA synovial samples have shown that there is more patient-to-patient variation in the levels of TSG-6 protein compared to OPG (see FIG. 6). This suggests that absence/low levels of TSG-6 could contribute to the extent and severity of osteolytic diseases.

Figure 7:
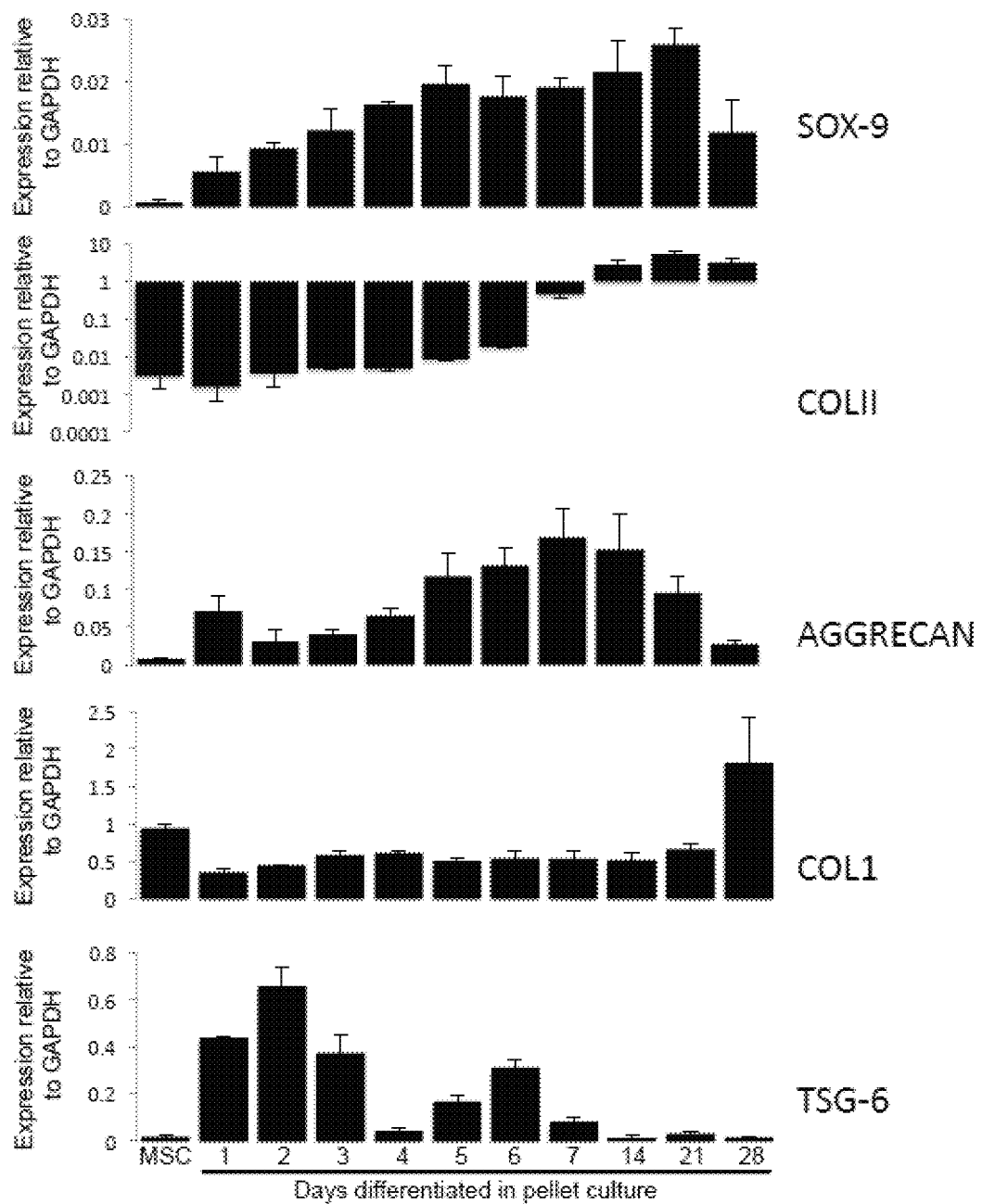
FIG. 7 shows expression analysis of cartilage-specific genes (SOX-9, COLII, Aggrecan) or genes expressed at low levels in cartilage (COL1 and TSG-6) during cartilage formation in 3D pellet culture in vitro. Expression levels are relative to GAPDH calculated using the $2^{-deltaCt}$ method. MSC=human mesenchymal stem cells in monolayer culture. Error bars=S.E.M. (n=2 independent experiments in which each time-point was performed in triplicate, and is representative of analyses performed on 4 human donor cell lines).

Example 7—Validation of Chondrocytes Generated by Differentiation of hMSC in 3D Culture Pellets of human mesenchymal stem cells (hMSCs) were maintained in chondrogenic media and gene expression profiles were assessed by quantitative PCR in order to confirm a chondrocyte-like phenotype (FIG. 7). Expression of SOX-9, which encodes a transcription factor that promotes chondrocyte differentiation and survival, was significantly up-regulated when cells were maintained in 3D pellets as compared to MSCs in monolayer cultures. The genes encoding type II collagen (COL2A1) and aggrecan, i.e. major structural components of the cartilage extracellular matrix (ECM), were also up-regulated in chondrocyte pellets. By contrast, as expected, the expression of COL1A1 (encoding type I collagen) was down-regulated (except at the 28-day time point). TSG-6 showed elevated expression with a cyclical profile during the first week of culturing in 3D pellets, but expression levels were close to those of monolayer cultures after 14, 21 and 28 days in the pellet system. In the examples illustrated in FIGS. 8, 9,10,12,14 and 15, pellet cultures were maintained for 14 days prior to stimulation with cytokines, where the gene expression profile of chondrocyte-like cells at this time point is characteristic of articular chondrocytes in vivo (FIG. 7).

The following primers were used for gene expression analysis:

| Gene | Primer | Sequence | Amplicon size |
|---|---|---|---|
| ADAMTS-4 | Forward | 5'-CATGTGCAACGTCAAGGCTC-3' | 223 bp |
|  | Reverse | 5'-CACCACCAAGCTGACAGGAT-3' |  |
| ADAMTS-5 | Forward | 5'-GCCTCTCCCATGACGATTCC-3' | 195 bp |
|  | Reverse | 5'-CCAGGATCTGCTTTCGTGGT-3' |  |
| MMP13 | Forward | 5'-AGGAGCATGGCGACTTCTAC-3' | 183 bp |
|  | Reverse | 5'-CAAGACCTAAGGAGTGGCCG-3' |  |
| TSG-6 | Forward | 5'-CATATGGCTTGAACGAGCAGC-3' | 316 bp |
|  | Reverse | 5'-CTTTGCGTGTGGGTTGTAGC-3' |  |
| GAPDH | Forward | 5'-CTCCTGTTCGACAGTCAGCC-3' | 110 bp |
|  | Reverse | 5'-CCCAATACGACCAAATCCGTTG-3' |  |

Example 8—TSG-6 Expression in Response to Inflammatory Mediators

Figure 8A:
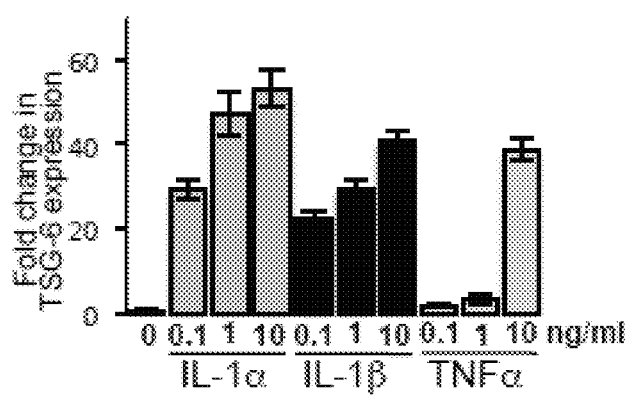
FIGS. 8A and 8B show treatment of 14 day pellet cultures with inflammatory cytokines for 24 h. (A) Dose-dependent cytokine-induced expression of TSG-6 mRNA. Fold change in expression calculated relative to no-addition control. Graph is pooled data from two independent experiments with each condition performed in triplicate and is representative of data collected with four discrete human donor cell lines (B) TSG-6 protein was detected in the media of pellet cultures treated with 1 ng/ml of IL-1α, IL-1β or TNFα.
Figure 8B:
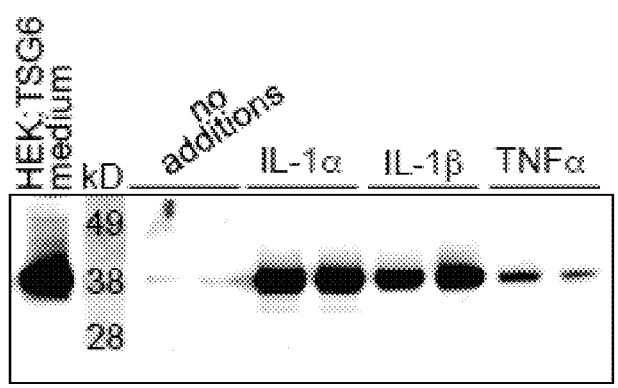

The effect of inflammatory mediators on TSG-6 expression was investigated in vitro using 3D pellet cultures, which were incubated in the presence of IL-1α, IL-1β or TNFα for 24 hours. Dose-dependent increases in TSG-6 mRNA expression were seen in response to all three cytokines (FIG. 8A), with IL-1α having the most potent effect (45- to 55-fold up-regulation). Western blot analysis of concentrated culture media revealed that elevated TSG-6 transcription was associated with increased secretion of TSG-6 protein by cells treated with IL-1α, IL-1β or TNFα (1 ng/ml; FIG. 8B).

Figure 9:
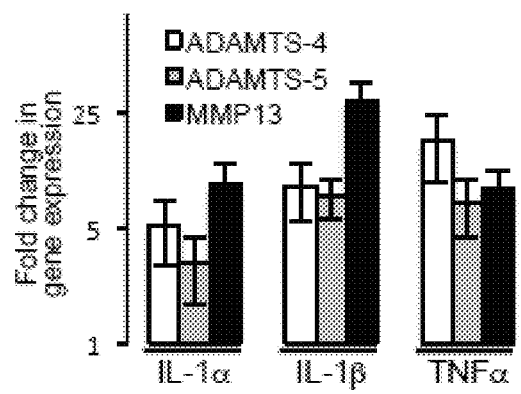
FIG. 9 shows treatment of 14 day pellet cultures with inflammatory cytokines. Expression of ADAMTS-4, ADAMTS-5 or MMP13 mRNA when incubated with 1 ng/ml IL1α, 10 ng/ml IL-1β or 10 ng/ml TNFα was determined. Fold change in expression was calculated relative to no-cytokine control. Data are expressed as mean values±S.E.M. for experiments using cells from 4 different donors.
Figure 10A:
FIGS. 10A and 10B show generation of 14 day pellet cultures in the absence of cytokine treatment. (A) ECM components of pellet cultures were identified with Safranin-O, Alcian Blue pH 1.0 and Alcian Blue pH 2.5 (left-right). (B) Fluorescence images showing staining of DNA (DAPI), hyaluronan (HA) and TSG-6 (left-right). Scale Bar=100 μm.
Figure 10B:
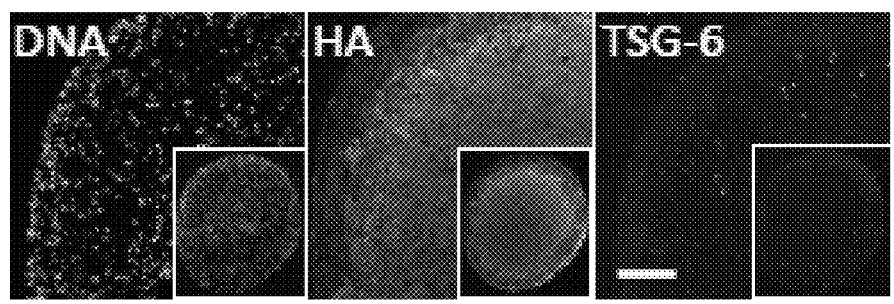

Example 9—Expression of Cartilage Degrading Enzymes by Chondrocytes in Response to Inflammatory Mediators To further validate its use for the study of cytokine-induced cartilage-degradation, the expression of proteolytic enzymes by chondrocytes was analysed in the 3D pellet culture system. MMP13, which cleaves type II collagen, and the aggrecanases ADAMTS-4 and (to a lesser extent) ADAMTS-5 are largely responsible for the loss of cartilage integrity during OA. Incubation of pellet cultures with IL-1α, IL-1β or TNFα 24 h resulted in substantial (4- to 25-fold) up-regulation of MMP13, ADAMTS-4 and ADAMTS-5 mRNA expression, where these effects were seen consistently for chondrocytes derived from the bone marrow aspirates of four different donors (FIG. 9). Furthermore, chondrocytes cultured in 3D pellets were found to secrete a cartilage-like ECM containing proteoglycans and sulphated glycosaminoglycans (GAGs), with hyaluronan as a major component (FIGS. 10A and 10B). It was observed that, in the absence of pro-inflammatory cytokines, TSG-6 was present at very low levels associated with only a small proportion of chondrocyte-like cells (FIG. 10B). Thus, the pellet culture system described here represents a good model of cartilage, where chondrocytes respond to pro-inflammatory cytokines by producing catabolic enzymes implicated in OA pathology and where these cytokines also promote elevated expression of TSG-6.

Example 10—Effect of TSG-6 on Cytokine-Induced Production of Cartilage Degrading Enzymes by Chondrocytes Two complementary approaches were used to determine the effects of TSG-6 on the cytokine-induced expression of ADAMTS-4 and ADAMTS-5 and MMP13 by chondrocytes. Firstly, exogenous addition of recombinant proteins, either full-length human TSG-6 or its isolated Link module domain (rhTSG-6 and Link_TSG6, respectively; FIG. 11), to pellet cultures was tested; cells were incubated for 24 hours in the absence or presence of IL-1β and without or with rhTSG6 or Link_TSG6. In the absence of IL-1β, rhTSG-6 caused a small up-regulation in the expression of the ADAMTS-4 and ADAMTS-5 genes, which in the latter case was significant at the 0.1 and 1 µM protein concentrations (FIG. 12A). By contrast, Link_TSG6 had no effect on ADAMTS-4, ADAMTS-5 or MMP13 expression at any of the concentrations tested. However, when added to chondrocytes in the presence of 10 ng/ml IL-1β both rhTSG-6 and Link_TSG6 inhibited the expression of all three catabolic enzymes in a dose-dependent manner (FIG. 12B). The effects on ADAMTS-5 expression were quite modest, but both rhTSG-6 and Link_TSG6 were potent inhibitors of ADAMTS-4 and MMP13 expression. Link_TSG6 was substantially more potent than the full-length protein as an inhibitor of IL-1β-induced MMP13 expression, where concentrations of ≥0.1 µM caused a return to basal levels (i.e. without IL-1β) of MMP13.

Figure 12C:
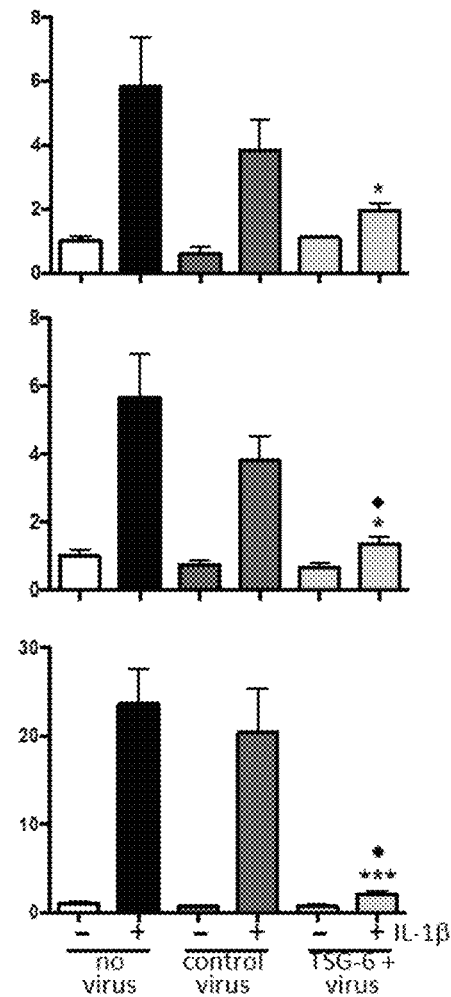

A second approach utilised lentivirus to introduce a construct into the genomic DNA of MSCs thereby enabling the constitutive over-expression of full-length TSG-6 (FIG. 12C); these cells were then differentiated into chondrocytes in 3D pellets. Chondrocytes derived from MSCs infected with 'control viral particles' (i.e. containing an expression cassette lacking the TSG-6 coding sequence) showed ADAMTS-4, ADAMTS-5 and MMP13 mRNA expression profiles very similar to those of uninfected cells, i.e. with substantial increases in expression in response to IL-1β (FIG. 12C). In contrast, chondrocytes that were constitutively over-expressing TSG-6 had greatly reduced sensitivity to IL-1β, with essentially no cytokine-induced up-regulation of MMP13 expression and significantly reduced expression of ADAMTS-4 and ADAMTS-5.

Figure 13:
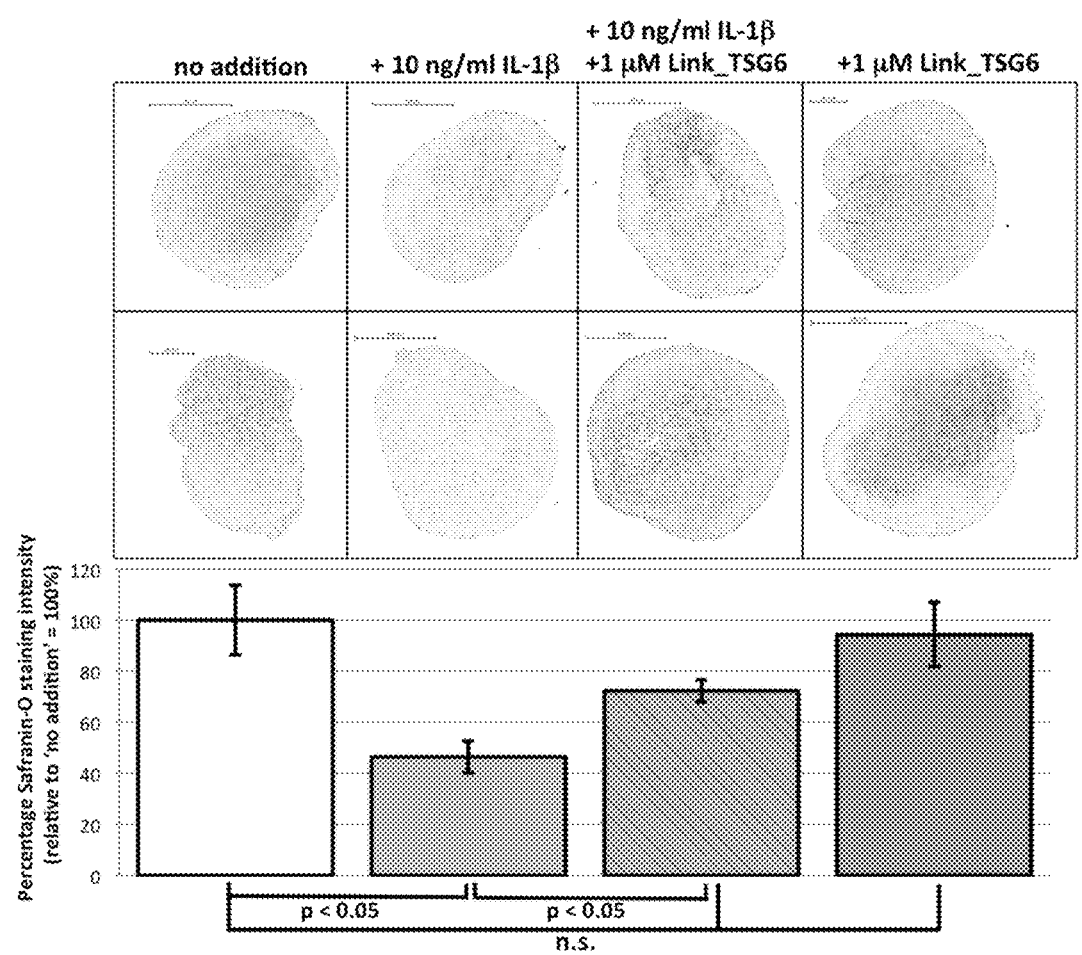
FIG. 13 shows that Link_TSG6 inhibits IL-1β-induced cartilage matrix degradation. Human chondrocytes generated from bone-marrow-derived stem cells (BMSC) were grown in 3D pellet cultures for 28 days. Following stimulation with 10 ng/ml IL-1β for 3 days, in the absence or presence of Link_TSG6, the pellets were stained with Safranin-O to determine glycosaminoglycan (GAG) content. Preliminary data from a single experiment show that Link_TSG6 can inhibit IL-1β induced breakdown of cartilage extracellular matrix.

Consistent with its inhibition of IL-1β-induced catabolic enzyme expression, Link_TSG6 (1 µM) was found to reduce the extent of GAG loss from chondrocyte pellets (as determined by Safranin-O staining; FIG. 13) when these were incubated for 3 days with 10 ng/ml IL-1β.

Recombinant proteins and lentivirus were employed to assess the effect of TSG-6 on IL-1α- and TNFα-stimulated expression of ADAMTS-4, ADAMTS-5 and MMP13 (FIG. 14).

Figure 14A:
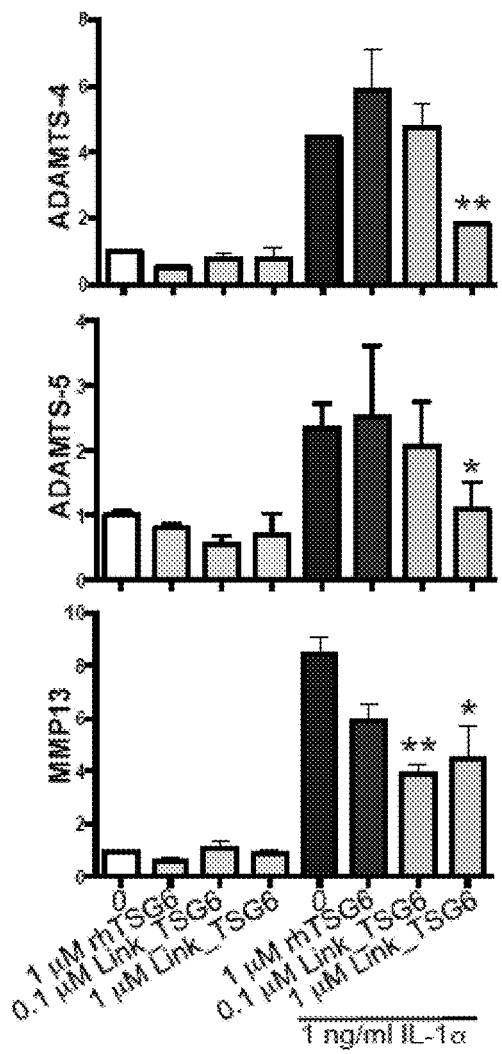
FIGS. 14A-14D show inhibition of IL-1α- or TNFα-induced ADAMTS-4, ADAMTS-5 and MMP13 expression. (A) and (B) are representative of experiments performed on 3 distinct human donor cell lines in which each experimental condition was performed in triplicate. (C) and (D) show pooled data from two independent experiments in which each experimental condition was performed in triplicate. Data are presented as mean values±S.E.M. *P<0.05  P<0.01 * P<0.005; one way ANOVA with Dunnett's multiple comparisons test relative to controls with +IL-1α or +TNFα alone. All y-axes indicate 'Fold change in gene expression relative to no addition control'.

In the presence of IL-1α exogenous addition of 1 µM rhTSG6 had no significant effect on the expression of ADAMTS-4, ADAMTS-5 or MMP13, whereas Link_TSG6 exerted a significant down-regulation of all the genes analysed (FIG. 14A).

Figure 14B:
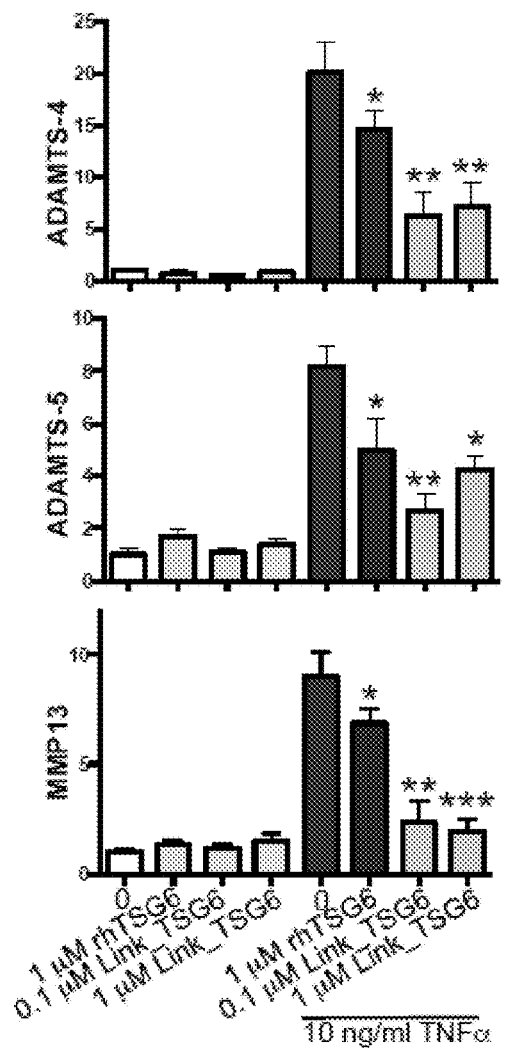

Exogenous addition of rhTSG6 and Link_TSG6 significantly down-regulated TNFα-mediated expression of both ADAMTS genes and MMP13 and again this down-regulation was greater upon incubation with Link_TSG6 (FIG. 14B).

Figure 14C:
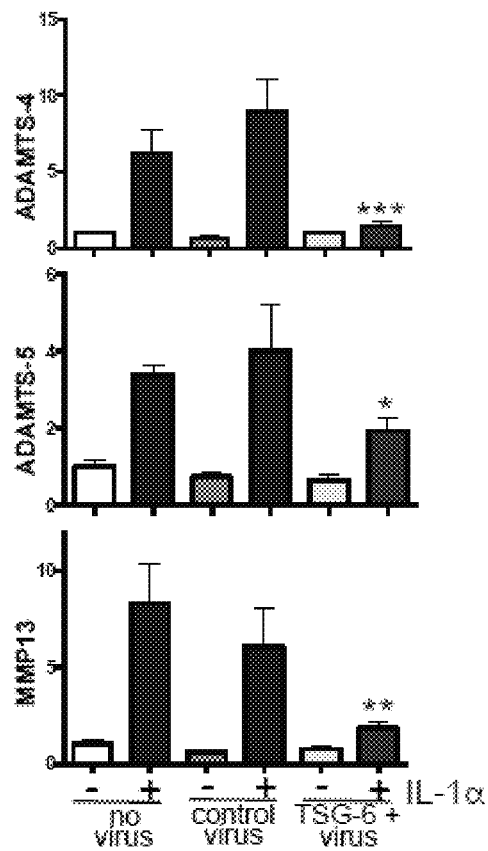
Figure 14D:
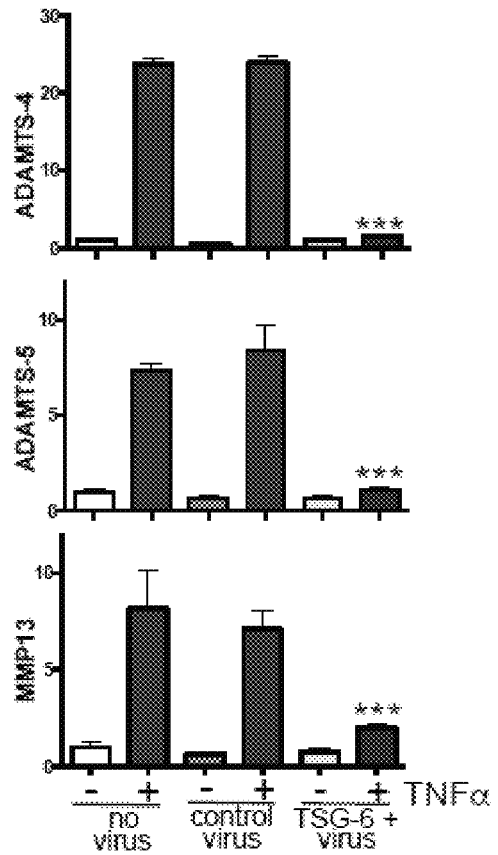

Lentivirus-mediated constitutive over-expression of full-length TSG-6 potently inhibited upregulation of ADAMTS-4, ADAMTS-5 and MMP13 genes response to either IL-1α or TNFα (FIGS. 14C and 14D).

These data show that TSG-6 may act directly on chondrocytes to counter the pro-catabolic effects of inflammatory cytokines and significantly suppress the up-regulation of the cartilage proteinases by IL-1/TNFα. Moreover, they identify recombinant human TSG-6 and Link_TSG6 as inhibitors of aggrecanase (e.g. ADAMTS-4, ADAMTS-5) and collagenase (e.g. MMP13) expression, with Link_TSG6 having more potent effects than the full-length protein in most cases.

Example 11—Effect of Exogenous TSG-6 on TSG-6 Expression

The effect of exogenous TSG-6 proteins on expression of TSG-6 was investigated by gene expression analysis after 24 hour incubation of pellet cultures with rhTSG6 or Link_TSG6.

Figure 15:
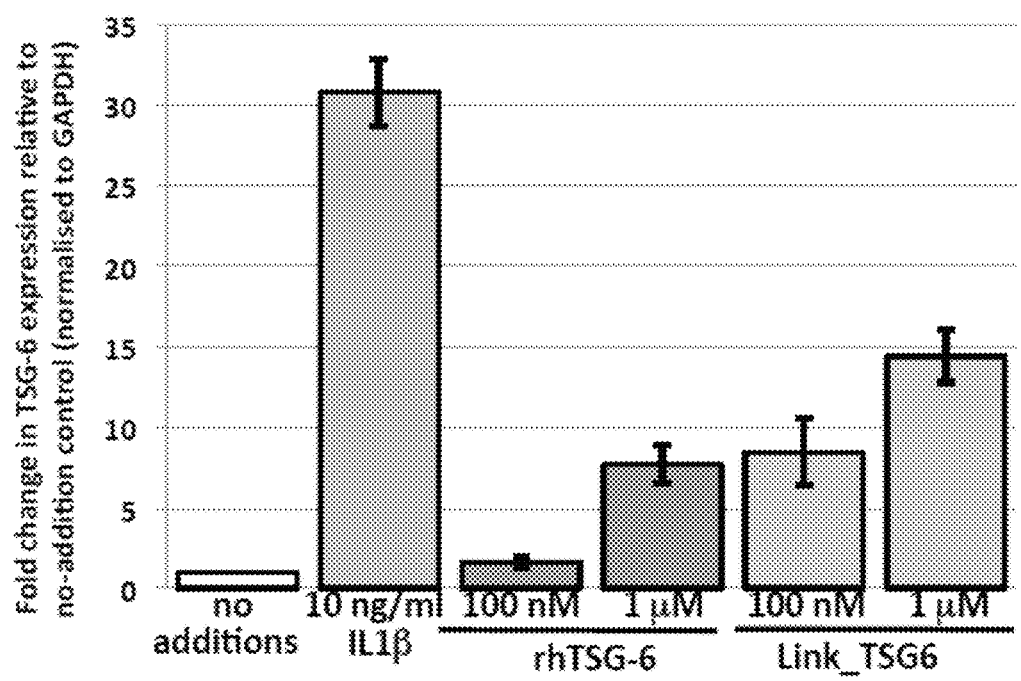
FIG. 15 shows exogenous addition of TSG-6 induces endogenous TSG-6 expression with Link_TSG6 being a more potent inducer of TSG-6 expression. Y-axis indicates fold change in TSG-6 expression relative to no-addition control. Data are presented as mean values±s.e.m. from three independent experiments in which each treatment was performed in triplicate. *P<0.05 * P<0.001 ** P<0.0001 calculated by one way ANOVA with Dunnett's multiple comparisons test relative to no addition control.

TSG-6 expression was found to be upregulated by addition of exogenous rhTSG-6 and Link_TSG6 in a dose-dependent manner. Surprisingly, Link_TSG6 was found to be more potent at inducing gene expression of TSG-6 than full-length recombinant human TSG-6 (FIG. 15).

TSG-6 may therefore be part of a positive feedback loop promoting TSG-6 expression, possibly to increase cellular defence against local cytokine-mediated inflammation.

These data suggest that TSG-6 produced by chondrocytes in response to inflammatory stimuli may act as an autocrine inhibitor of chondrocyte catabolic activity and thereby regulate cartilage breakdown.

Example 12—Expression of TSG-6 by Chondrocytes in Osteoarthritis

Figure 16:
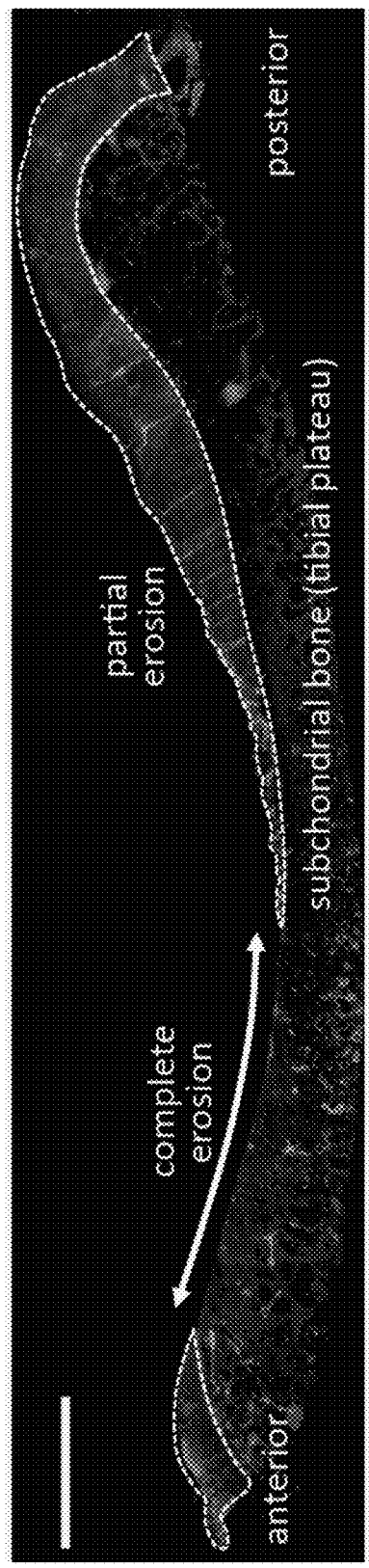
FIG. 16 shows characteristic pattern of cartilage erosion and fibrillation at the tibial plateau in human osteoarthritis of the knee. Fluorescence image with annotation indicating section orientation and cartilage morphology.

Having shown that TSG-6 potently reduces cartilage breakdown via down-regulation of catabolic enzyme expression in vitro localisation and distribution of TSG-6 within human OA cartilage and associated chondrocytes was investigated. Presence of TSG-6 was determined by immunofluorescence analyses of human tibial plateau cartilage from donors diagnosed with anteromedial gonarthrosis (AMG) undergoing partial knee re-sectioning. The characteristic pattern of cartilage destruction in OA allowed us to generate full-length cartilage sections with loss of cartilage, revealing the underlying subchondral bone towards the anterior of the section, progressing through fibrillated, eroded cartilage towards full-thickness cartilage and often osteophyte formation at the very posterior of the section (FIGS. 16-18). These full-length sections were processed for both Safranin-O and immunofluorescence imaging.

Figure 17A:
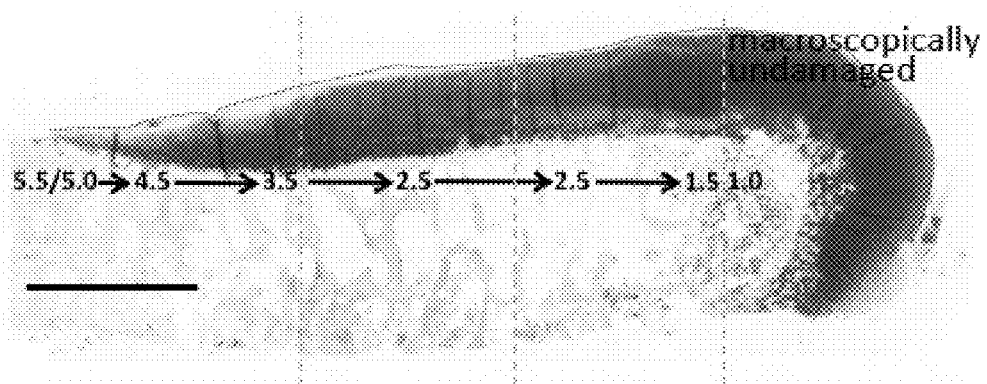
FIGS. 17A-17D show grading scheme for zoning of human osteoarthritis cartilage of the tibial plateau and quantitative analysis of TSG-6 distribution/cell-association throughout diseased cartilage. (A) Safranin-O staining of cartilage from macroscopically undamaged cartilage (with an OARSI grading score of ≤1) at the posterior of the section through progressively more damaged and fibrillated cartilage and finally the exposed subchondrial bone surface. Scale Bar=4000 μm.
Figure 17B:
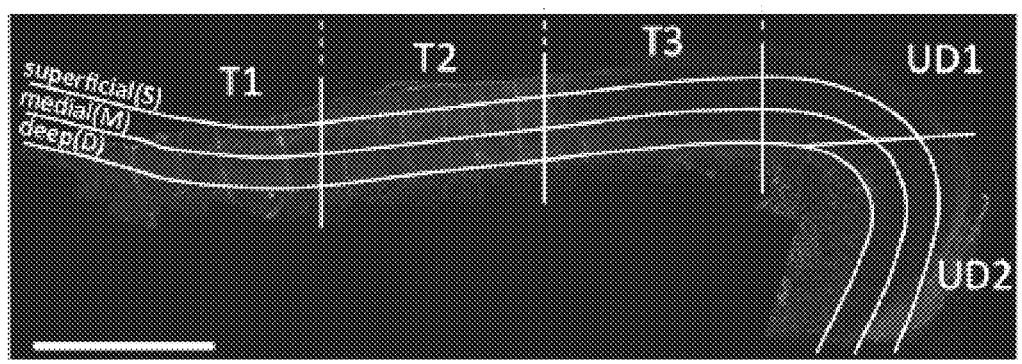

Sections were stained with Safranin-O and graded using the Osteoarthritis Research Society International (OARSI) grading scale and the region of full-thickness cartilage with a score of ≤1.0 was denoted as macroscopically un-damaged (UD; FIG. 17A-17B) and this was further sub-divided into UD1 and UD2, where UD1 was cartilage parallel to the bone/cartilage interface and UD2 was largely perpendicular to the bone surface. The remaining cartilage located anteriorly to the UD sub-sections was divided into thirds (T1, T2 and T3) and then all cartilage zones were further divided longitudinally into thirds termed 'deep' (D), 'medial' (M) and 'superficial' (S) with 'deep' cartilage juxtaposed to the underlying sub-chondral bone (FIG. 17B).

Quantitative semi-automated fluorescence analyses were performed on each defined zone of cartilage within a minimum of 3 consecutive sections from each donor. Briefly, the total numbers of cells per mm$^2$ (as determined by staining with DAPI) were counted in the superficial, mid and deep zones of each region, and the percentage of TSG-6-positive cells was quantified for each region using automated 'object counting'.

Figure 17C:
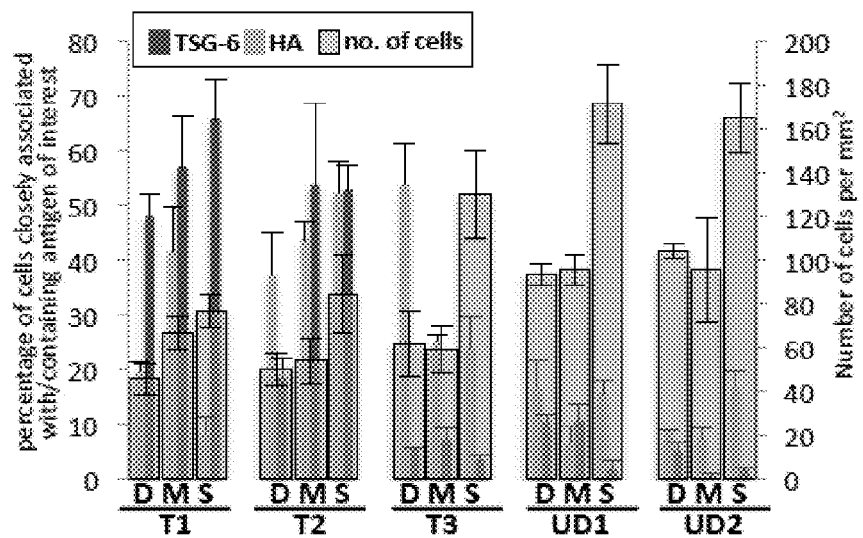
Figure 17D:
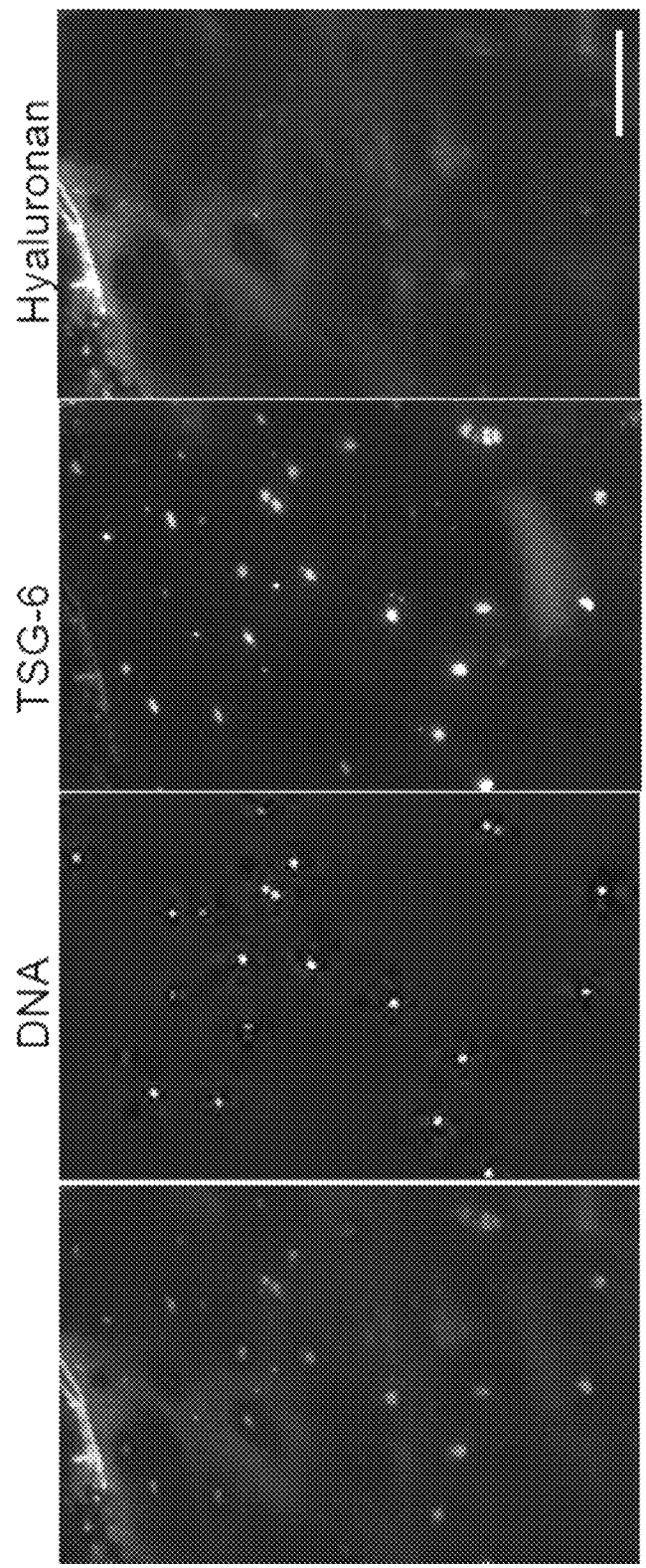

These methods revealed that the degree of loss of cartilage (T1>T2>T3) correlated with the percentage of cells staining positive for TSG-6 (i.e. T1 (~50-70%)>T2 (~20-50%)>T3 (≤~10%); FIG. 17C). That is, TSG-6 was found predominately in chondrogenic clusters at the damaged superficial margins of the cartilage. TSG-6 expression was also observed in ~10% of chondrocytes in the deep and mid zones of the undamaged cartilage adjacent to T3 (UD1; FIG. 17C).

TSG-6 was consistently associated with regions of significant cartilage loss (i.e. all zones within T1 and superficial and medial zones of T2; FIGS. 17C and 18B). In addition, TSG-6 was also associated with a small number of cells within the macroscopically undamaged regions of cartilage (UD1 and UD2). Again, this was consistent across all OA diagnosed donor cartilage analysed.

TSG-6 was present predominantly in, or close to, clusters of chondrocytes (FIG. 17D) within the most damaged regions of human articular cartilage of the tibial plateau. These cell clusters are characteristic of pathological cell proliferation associated with osteoarthritis.

Fluorescence multiplexing analyses were used to determine if the localization of TSG-6 protein correlated with expression of MMP13 mRNA transcripts in human OA chondrocytes. TSG-6 protein was identified with the RAH-1 antibody and MMP13 mRNA was detected using anti-sense dioxygenin-labelled RNA probes with subsequent Tyramide signal amplification (TSA; Perkin Elmer, USA). This revealed an inverse correlation between TSG-6 protein localization and MMP13 mRNA (FIGS. 19A and 19B). This is consistent with the data (FIGS. 12 and 13) showing that TSG-6 down-regulates cytokine-induced expression of MMP13 by chondrocytes.

The following numbered paragraphs contain statements of broad combinations of the inventive technical features herein disclosed:

A. Use of a TSG-6 polypeptide, or a polynucleotide encoding a TSG-6 polypeptide, in the manufacture of a medicament for the treatment or prevention of a disease or condition associated with bone resorption by osteoclasts.

B. Use according to paragraph A, wherein said TSG-6 polypeptide comprises:
  (a) the amino acid sequence of SEQ ID NO: 2 or 5;
  (b) a variant thereof having at least 50% identity to the amino acid sequence of SEQ ID NO: 2 or 5 and receptor activator of NF$_k$B ligand (RANKL) binding activity; or
  (c) a fragment of either (a) or (b) having RANKL binding activity.

C. Use according to paragraph B, wherein said polypeptide consists of the sequence shown in SEQ ID NO: 2 or 5.

D. Use according to paragraph A, wherein said polynucleotide comprises:
  (a) the coding sequence of SEQ ID NO: 1, 4, 8 or 12;
  (b) a sequence which is degenerate as a result of the genetic code to the sequence as defined in (a);
  (c) a sequence having at least 60% identity to a sequence as defined in (a) or (b) and which encodes a polypeptide having RANKL binding activity; or
  (d) a fragment of any one of the sequences as defined in (a), (b) or (c) which encodes a polypeptide having RANKL binding activity.

E. Use according to paragraph D, wherein said polynucleotide consists of the nucleic acid sequence shown in SEQ ID NO: 1, 4, 8 or 12.

F. Use according to any one of paragraphs A to E, wherein the medicament is administered in combination with a therapeutically or prophylactically effective amount of an osteoprotegerin (OPG) polypeptide, a polynucleotide encoding an OPG polypeptide or an OPG mimetic.

G. Use according to paragraph F, wherein the OPG polypeptide comprises:
  (a) the amino acid sequence of SEQ ID NO: 15;
  (b) a variant thereof having at least 50% identity to the amino acid sequence of SEQ ID NO: 15 and having RANKL binding activity; or
  (c) a fragment of either (a) or (b) having RANKL binding activity. Preferably, the OPG polypeptide comprises, or consists of, the sequence of SEQ ID NO: 15.

H. Use according to paragraph F, wherein the OPG polynucleotide comprises:
  (a) the coding sequence of SEQ ID NO: 14;
  (b) a sequence which is degenerate as a result of the genetic code to the sequence as defined in (a);

(c) a sequence having at least 60% identity to a sequence as defined in (a) or (b) and which encodes a polypeptide having RANKL binding activity; or (d) a fragment of any one of the sequences as defined in (a), (b) or (c) which encodes a polypeptide having RANKL binding activity.

I. Use according to any one of paragraphs A to H, wherein the disease or condition is osteoarthritis, osteoporosis, bone cancer, a bone lesion associated with metastatic cancer, Paget's disease, Gorham Stout disease, primary hyperparathyroidism, periodontal disease, a bone fracture and/or aseptic loosening of joint replacements.

J. A method of treating or preventing a bone disease or condition associated with bone resorption by osteoclasts in a subject in need thereof, the method comprising administering to the subject a therapeutically or prophylactically effective amount of an TSG-6 polypeptide, or a polynucleotide encoding an TSG-6 polypeptide.

K. Use of:
(a) a TSG-6 polypeptide, or a polynucleotide encoding a TSG-6 polypeptide; and
(b) an OPG polypeptide, a polynucleotide encoding an OPG polypeptide or an OPG mimetic;

in the manufacture of a medicament for the treatment or prevention of a disease or condition associated with bone resorption by osteoclasts.

L. A product containing:
(a) a TSG-6 polypeptide, or a polynucleotide encoding a TSG-6 polypeptide; and
(b) an OPG polypeptide, a polynucleotide encoding an OPG polypeptide or an OPG mimetic;

for simultaneous, separate or sequential use in the treatment or prevention of a disease or condition associated with bone resorption by osteoclasts.

M. Use of:
(a) a TSG-6 polypeptide, or a polynucleotide encoding a TSG-6 polypeptide; or
(b) an OPG polypeptide, a polynucleotide encoding an OPG polypeptide or an OPG mimetic;

in the manufacture of a medicament for the treatment or prevention by combination therapy of a disease or condition associated with bone resorption by osteoclasts, wherein (a) and (b) are administered simultaneously, separately or sequentially.

The invention claimed is:

1. A method for inhibiting cartilage degradation in a subject, the method comprising administering to a subject in need of treatment a therapeutically effective amount of a Link_TSG6 polypeptide, thereby inhibiting cartilage degradation, wherein the Link_TSG6 polypeptide is a fragment of the human TSG6 polypeptide that consists of (i) the amino acid sequence of SEQ ID NO: 9, 27, 7 or 26, or (ii) an amino acid sequence having at least 95% identity to the amino acid sequence of SEQ ID NO: 9, 27, 7 or 26 and being capable of inhibiting IL-1α, IL-β or TNFα induced expression of ADAMTS-4 ADAMTS-5 or MMP13.

2. The method according to claim 1, wherein the cartilage degradation is associated with osteoarthritis in the subject.

3. The method according to claim 1 wherein the subject has osteoarthritis.

4. The method of claim 1 wherein the subject has osteoarthritis selected from the group consisting of: trauma or injury induced osteoarthritis, age-related osteoarthritis and non-age related osteoarthritis.

5. A method for maintaining effective cartilage tissue in the joint of a patient following injury or trauma to the joint, the method comprising administering to a patient a therapeutically effective amount of a Link_TSG6 polypeptide, following said injury or trauma, thereby preventing, delaying or treating the onset of loss or degeneration of cartilage tissue in said joint, wherein the Link_TSG6 polypeptide is a fragment of the human TSG6 polypeptide that consists of (i) the amino acid sequence of SEQ ID NO: 9, 27, 7 or 26, or (ii) an amino acid sequence having at least 95% identity to the amino acid sequence of SEQ ID NO: 9, 27, 7 or 26 and being capable of inhibiting IL-1α, IL-β or TNFα induced expression of ADAMTS-4 ADAMTS-5 or MMP13.

6. The method of claim 5 wherein said polypeptide is administered within 1 week or less of the injury or trauma.

7. The method of claim 5 wherein said polypeptide is administered within 1 month or less of the injury or trauma.

* * * * *